United States Patent
Inoue et al.

(10) Patent No.: US 7,214,824 B2
(45) Date of Patent: May 8, 2007

(54) SUBSTITUTED N-SULFONYLAMINOBENZYL-2-PHENOXYACETAMIDE COMPOUNDS AS VR1 RECEPTOR AGONISTS

(75) Inventors: Tadashi Inoue, Aichi-ken (JP); Satoshi Nagayama, Aichi-ken (JP); Kazunari Nakao, Aichi-ken (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/270,780

(22) Filed: Nov. 9, 2005

(65) Prior Publication Data

US 2006/0100460 A1    May 11, 2006

Related U.S. Application Data

(60) Provisional application No. 60/626,559, filed on Nov. 10, 2004.

(51) Int. Cl.
C07C 303/00 (2006.01)
C07C 307/00 (2006.01)
C07C 309/00 (2006.01)
C07C 311/00 (2006.01)

(52) U.S. Cl. .................... 564/94; 546/229
(58) Field of Classification Search ............ 564/94; 546/229
See application file for complete search history.

(56) References Cited

FOREIGN PATENT DOCUMENTS

| WO | WO 2002/16318 A1 | 2/2002 |
|---|---|---|
| WO | WO 2002/16319 A1 | 2/2002 |
| WO | WO 2004/035533 A1 * | 4/2004 |
| WO | WO 2005/003084 A1 | 1/2005 |
| WO | WO 2005003084 * | 1/2005 |

OTHER PUBLICATIONS

J. Hogue, et al., "Pathophysiology and First-line Treatment of Osteoarthritis", The Annal of Pharmacotherapy, Apr. 2002, pp. 679-686, vol. 36.
D. Grennan, et al., "Rheumatoid Arthritis", Textbook of Pain, 1994, pp. 397-407.
R. Meyer, et al., "Peripheral Neural Mechanisms of Nociception", Textbook of Pain, 1994, pp. 13-44.
J. Levine, et al., "Inflammatory Pain", Textbook of Pain, 1994 pp. 45-56.
M. Millan, et al., "The Induction of Pain: An Inegrative Review", Progress in Neurobiology, 1999, pp. 1-164, vol. 57.
C Woolf, et al., "Implications of Recent Advances in the Understanding of Pain Pathophysiology for the Assessment of Pain in Patients", Pain Supplement 1999, pp. S141-S147, vol. 6.
C. Woolf, et al., "Neuropathic Pain: Aetiology, Symptoms, Mechanisms, and Management", The Lancet, Jun. 5, 1999, vol. 353.
C Woolf, et al., "Neuronal Plasticity: Increasing the Gain in Pain", Science, Jun. 9, 2000, pp. 1765-1768, vol. 288.

* cited by examiner

Primary Examiner—Thurman K. Page
Assistant Examiner—Chukwuma Nwaonicha
(74) Attorney, Agent, or Firm—Charles W. Ashbrook; David R. Kurlandsky

(57) ABSTRACT

This invention provides a compound of the formula (I):

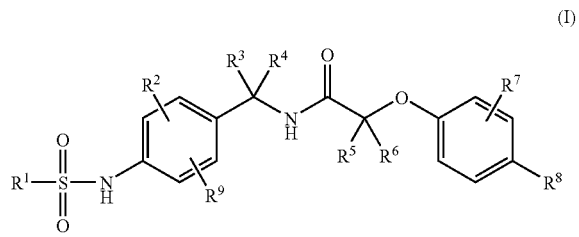

wherein $R^1$ represents a $(C_1-C_6)$alkyl group; $R^2$ represents a hydrogen atom, a halogen atom, a hydroxy group, a $(C_1-C_6)$ alkyl group or a $(C_1-C_6)$alkoxy group; $R^3$, $R^4$, $R^5$ and $R^6$ each independently represents a hydrogen atom, a $(C_1-C_6)$ alkyl, or a halogen atom; $R^7$ represents a hydrogen atom, a halogen atom, a hydroxy group, a $(C_1-C_6)$alkyl group optionally substituted with a piperidino group, a $(C_1-C_6)$ alkoxy group optionally substituted with a 3–7 membered cycloalkyl ring, a hydroxy$(C_1-C_6)$alkoxy group, a $(C_1-C_6)$ alkoxy-$(C_1-C_6)$alkyl group, a $(C_1-C_6)$alkoxy-$(C_1-C_6)$ alkoxy group, a halo $(C_1-C_6)$alkyl group, a $(C_1-C_6)$alkylthio group, a $(C_1-C_6)$alkylsulfinyl group or a $(C_1-C_6)$ alkylsulfonyl group; $R^8$ represents a $(C_1-C_6)$alkyl group, a halo$(C_1-C_6)$alkyl group, a $(C_1-C_6)$alkoxy group, a hydroxy $(C_1-C_6)$alkoxy group, a $(C_1-C_6)$alkoxy-$(C_1-C_6)$alkyl group or a $(C_1-C_6)$alkoxy-$(C_1-C_6)$alkoxy group; or $R^7$ and $R^8$, when adjacent to each other, taken together with the carbon atoms to which they are attached form a 5–8 membered carbocyclic or heterocyclic ring, wherein the carbocyclic ring or the heterocyclic ring is unsubstituted or substituted with one or more substituents selected from the group consisting of a hydroxy group, a $(C_1-C_6)$alkyl group, a $(C_1-C_6)$alkoxy group and a hydroxy$(C_1-C_6)$alkyl group; and $R^9$ represents a hydrogen atom or a halogen atom; or a pharmaceutically acceptable salt or solvate thereof.

These compounds are useful for the treatment of disease conditions caused by overactivation of VR1 receptor, such as pain or the like in mammalian. The present invention also provides a pharmaceutical composition comprising the compound of formula(I).

10 Claims, No Drawings

SUBSTITUTED N-SULFONYLAMINOBENZYL-2-PHENOXYACETAMIDE COMPOUNDS AS VR1 RECEPTOR AGONISTS

This application is a United States utility application, which claims the benefit of priority to U.S. Provisional Application No. 60/626,559, filed Nov. 10, 2004.

TECHNICAL FIELD

This invention relates to novel substituted N-sulfonylaminobenzyl-2-phenoxyacetamide compounds. These compounds are useful as antagonists of VR1 (Type I Vanilloid receptors) or TRPV-1 (Transient receptor potential channel, vanilloid subfamily member-1), and are thus useful for the treatment of pain, neuralgia, neuropathies, nerve injury, burns, migraine, carpal tunnel syndrome, fibromyalgia, neuritis, sciatica, pelvic hypersensitivity, bladder disease, inflammation, or the like in mammals, especially humans. The present invention also relates to a pharmaceutical composition comprising the above compounds.

BACKGROUND ART

Vanilloid receptor 1 (VR1) is a ligand gated non-selective cation channel. It is believed to be a member of the transient receptor potential super family. VR1 is recognized as a polymodal nociceptor that integrates multiple pain stimuli, e.g., noxious heat, protons, and vanilloids. A major distribution of VR1 is in the sensory (Aδ- and C-) fibers, which are bipolar neurons having somata in sensory ganglia. The peripheral fibers of these neurons innervate the skin, the mucosal membranes, and almost all internal organs. It is also recognized that VR1 exists in bladder, kidney, brain, pancreas, and various kinds of organs. A body of studies using VR1 agonists, e.g., capsaicin or resiniferatoxin, have suggested that VR1 positive nerves are thought to participate in a variety of physiological responses, including nociception. Based on both the tissue distribution and the roles of VR1, VR1 antagonists would have good therapeutic potential.

WO200216318A1 discusses N-sulfonylaminobenzyl-3-propionamide derivatives as a modulator for vanilloid receptor. However, the specification of WO200216318A1 is silence about the compounds having an oxygen atom as part of the amide linker between two phenyl groups.

WO200216319A1 discusses methansulfonylaminophenyl acetid acid derivatives as a modulator for vanilloid receptor. With respect to the order of NH and carbonyl groups in the linker between two phenyl groups, the compounds in WO200216319A1 is reverse to the compounds of the present invention. Further WO200216319A1 is silence about the compounds having an oxygen atom as part of the amide linker between two phenyl groups.

WO2005003084A1, published on Jan. 13, 2005 (after the first priority date of the present application of Nov. 11, 2004), discusses 4-(methylsulfonylamino)phenyl analogues as a vanilloid antagonist. However, in WO2005003084, there is no concrete description about phenoxy acetatamide compounds such as the compounds of the present invention. Also there is no description, suggestion or motivation about introducing an alkyl group to the phenyl group substituted with an alkylsulfonylamino group, or about compounds having a methylene group next to the phenyl group substituted with an alkylsulfonylamino group.

Further, the compounds of the present invention possess an excellent compound series in a human VR1 antagonist activitiy by introducing an oxygen atom into the linker. Further the compounds of the present invention also possess an excellent half-life value by introducing an oxygen atom into the linker, being substituted with an alkyl group to the phenyl group having an alkylsulfonylamino group and/or having a methylene group, as part of the linker, next to the phenyl group substituted with an alkylsulfonylamino group.

It would be desirable if there were provided a novel VR1 selective antagonist with potent binding activity with VR1 receptor by systemic administration, and both with less toxicity, good absorption, good half-life, good solubility, low protein binding affinity, less drug-drug interaction, a reduced inhibitory activity at HERG channel, reduced QT prolongation and good metabolic stability.

BRIEF DISCLOSURE OF THE INVENTION

It has now been found that substituted N-sulfonylaminobenzyl-2-phenoxyacetamide compounds are VR1 antagonists with analgesic activity by systemic administration. The compounds of the present invention may show less toxicity, good absorption, good half-life, good solubility, low protein binding affinity, less drug-drug interaction, a reduced inhibitory activity at HERG channel, reduced QT prolongation and good metabolic stability.

The present invention provides a compound of the following formula (I):

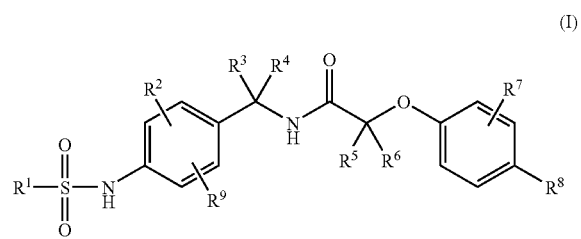

wherein $R^1$ represents a $(C_1-C_6)$alkyl group; $R^2$ represents a hydrogen atom, a halogen atom, a hydroxy group, a $(C_1-C_6)$ alkyl group or a $(C_1-C_6)$alkoxy group; $R^3$, $R^4$, $R^5$ and $R^6$ each independently represents a hydrogen atom, a $(C_1-C_6)$ alkyl, or a halogen atom; $R^7$ represents a hydrogen atom, a halogen atom, a hydroxy group, a $(C_1-C_6)$alkyl group optionally substituted with a piperidino group, a $(C_1-C_6)$ alkoxy group optionally substituted with a 3–7 membered cycloalkyl ring, a hydroxy$(C_1-C_6)$alkoxy group, a $(C_1-C_6)$ alkoxy-$(C_1-C_6)$alkyl group, a $(C_1-C_6)$alkoxy-$(C_1-C_6)$ alkoxy group, a halo $(C_1-C_6)$alkyl group, a $(C_1-C_6)$alkylthio group, a $(C_1-C_6)$alkylsulfinyl group or a $(C_1-C_6)$ alkylsulfonyl group; $R^8$ represents a $(C_1-C_6)$alkyl group, a halo$(C_1-C_6)$alkyl group, a $(C_1-C_6)$alkoxy group, a hydroxy $(C_1-C_6)$alkoxy group, a $(C_1-C_6)$alkoxy-$(C_1-C_6)$alkyl group or a $(C_1-C_6)$alkoxy-$(C_1-C_6)$alkoxy group; or $R^7$ and $R^8$, when adjacent to each other, may be taken together with the carbon atoms to which they are attached form a 5–8 membered carbocyclic or heterocyclic ring, wherein the carbocyclic ring or the heterocyclic ring is unsubstituted or substituted with one or more substituents selected from the group consisting of a hydroxy group, a $(C_1-C_6)$alkyl group, a $(C_1-C_6)$alkoxy group and a hydroxy$(C_1-C_6)$alkyl group; and $R^9$ represents a hydrogen atom or a halogen atom; or a pharmaceutically acceptable salt or solvate thereof.

Another enbodiment of the present invention is a compound of the formula (I-a) which claimed in U.S. provisional application 60/626,559 filed on Nov. 10, 2004:

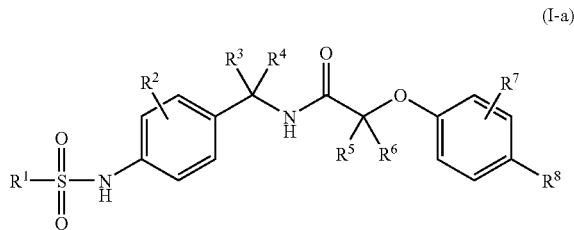

(I-a)

wherein $R^1$ represents a $(C_1-C_6)$alkyl or an aryl group; $R^2$ represents a hydrogen atom, a halogen atom, a hydroxy group, a $(C_1-C_6)$alkyl, a halo $(C_1-C_6)$alkyl, or a $(C_1-C_6)$alkoxy; $R^3$, $R^4$, $R^5$ and $R^6$ each independently represent a hydrogen atom, a $(C_1-C_6)$alkyl, a halogen atom, or a halo $(C_1-C_6)$alkyl, or $R^3$ and $R^4$, and/or, $R^5$ and $R^6$ are taken together with the carbon atoms to which they are attached to form a 3–7 membered cycloalkyl ring or heterocyclic ring in which one or two non-adjacent carbon atoms are optionally replaced by oxygen, sulfur or NH groups; $R^7$ represent a hydrogen atom, a halogen atom, a $(C_1-C_6)$alkyl, a $(C_1-C_6)$alkoxy, a hydroxy$(C_1-C_6)$alkoxy, a $(C_1-C_6)$alkoxy-$(C_1-C_6)$alkyl, a $(C_1-C_6)$alkoxy-$(C_1-C_6)$alkoxy, a halo $(C_1-C_6)$alkyl, a $(C_1-C_6)$alkylthio, a $(C_1-C_6)$alkylsulfinyl, a $(C_1-C_6)$alkylsulfonyl, or a $[(C_1-C_6)alkyl]NH—$, a $[(C_1-C_6)alkyl]_2N—$; and $R^8$ represent a halogen atom, a $(C_1-C_6)$alkyl, a halo $(C_1-C_6)$alkyl, a $(C_1-C_6)$alkoxy, a hydroxy$(C_1-C_6)$alkoxy, a $(C_1-C_6)$alkoxy-$(C_1-C_6)$alkyl, a $(C_1-C_6)$alkoxy-$(C_1-C_6)$alkoxy, or a $[(C_1-C_6)alkyl]NH—$, a $[(C_1-C_6)alkyl]_2N—$, or $R^7$ and $R^8$, when adjacent to each other, may be taken together with the carbon atoms to which they are attached to form a 5–8 membered cycloalkyl ring or heterocycric ring in which one or two non-adjacent carbon atoms are optionally replaced by oxygen, sulfur or NH groups, wherein the cycloalkyl ring or the heterocyclic ring is unsubstituted or substituted with one or more substituents selected from the group consisting of hydroxy, $(C_1-C_6)$alkyl, $(C_1-C_6)$alkoxy and hydroxy$(C_1-C_6)$alkyl; or a pharmaceutically acceptable salt or solvate thereof.

Another enbodiment of the present invention is a compound of the formula (I-b), which described in U.S. provisional applications 60/660,978 filed on Mar. 10, 2005 and 60/699,801 filed on Jul. 15, 2005:

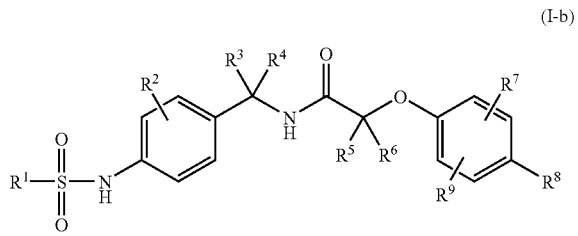

(I-b)

wherein $R^1$ represents a $(C_1-C_6)$alkyl or an aryl group; $R^2$ represents a hydrogen atom, a halogen atom, a hydroxy group, a $(C_1-C_6)$alkyl, a halo $(C_1-C_6)$alkyl, a $(C_1-C_6)$alkoxy; a hydroxy$(C_1-C_6)$alkoxy, a $(C_1-C_6)$alkoxy-$(C_1-C_6)$alkyl or a halo $(C_1-C_6)$alkyl; $R^3$, $R^4$, $R^5$ and $R^6$ each independently represent a hydrogen atom, a $(C_1-C_6)$alkyl, a halogen atom, a halo$(C_1-C_6)$alkyl, a $(C_1-C_6)$alkoxy-$(C_1-C_6)$alkyl or a hydroxy$(C_1-C_6)$alkyl, or $R^3$ and $R^4$, and/or, $R^5$ and $R^6$ are taken together with the carbon atoms to which they are attached to form a 3–7 membered cycloalkyl ring or heterocyclic ring in which one or two non-adjacent carbon atoms are optionally replaced by oxygen, sulfur or NH groups; $R^7$ represents a hydrogen atom, a halogen atom, a $(C_1-C_6)$alkyl, a $(C_1-C_6)$alkoxy, a hydroxy$(C_1-C_6)$alkoxy, a $(C_1-C_6)$alkoxy-$(C_1-C_6)$alkyl, a $(C_1-C_6)$alkoxy-$(C_1-C_6)$alkoxy, a halo $(C_1-C_6)$alkyl, a $(C_1-C_6)$alkylthio, a $(C_1-C_6)$alkylsulfinyl, a $(C_1-C_6)$alkylsulfonyl, or a $[(C_1-C_6)alkyl]NH—$, a $[(C_1-C_6)alkyl]_2N—$; $R^8$ represents a halogen atom, a $(C_1-C_6)$alkyl, a halo$(C_1-C_6)$alkyl, a $(C_1-C_6)$alkoxy, a hydroxy$(C_1-C_6)$alkoxy, a $(C_1-C_6)$alkoxy-$(C_1-C_6)$alkyl, a $(C_1-C_6)$alkoxy-$(C_1-C_6)$alkoxy, or a $[(C_1-C_6)alkyl]NH—$, a $[(C_1-C_6)alkyl]_2N—$, or $R^7$ and $R^8$, when adjacent to each other, may be taken together with the carbon atoms to which they are attached to form a 5–8 membered cycloalkyl ring or heterocycric ring in which one or two non-adjacent carbon atoms are optionally replaced by oxygen, sulfur or NH groups, wherein the cycloalkyl ring or the heterocyclic ring is unsubstituted or substituted with one or more substituents selected from the group consisting of hydroxy, $(C_1-C_6)$alkyl, $(C_1-C_6)$alkoxy and hydroxy$(C_1-C_6)$ alkyl; and $R^9$ represents a hydrogen atom, a halogen atom, a $(C_1-C_6)$alkyl, a $(C_1-C_6)$alkoxy, a hydroxy$(C_1-C_6)$alkoxy, a $(C_1-C_6)$alkoxy-$(C_1-C_6)$alkyl, a $(C_1-C_6)$alkoxy-$(C_1-C_6)$alkoxy, a halo $(C_1-C_6)$alkyl, a $(C_1-C_6)$alkylthio, a $(C_1-C_6)$alkylsulfinyl, a $(C_1-C_6)$alkylsulfonyl, a $[(C_1-C_6)alkyl]NH—$, a $[(C_1-C_6)alkyl]_2N—$, $H_2N—(C_1-C_6)$alkoxy, $(C_1-C_6)$alky-NH—$(C_1-C_6)$alkoxy, $[(C_1-C_6)alky]_2N(C_1-C_6)$alkoxy; $H_2N—(C_1-C_6)$alkoxy-$(C_1-C_6)$alkyl, $(C_1-C_6)$alky-NH—$(C_1-C_6)$alkoxy-$(C_1-C_6)$alky, $[(C_1-C_6)alky]_2N(C_1-C_6)$alkoxy-$(C_1-C_6)$alkyl;

or a pharmaceutically acceptable salt or solvate thereof.

The compounds of the present invention are antagonists of VR1 receptor and are thus useful in therapeutics, particularly for the treatment of acute cerebral ischemia, pain, chronic pain, neuropathic pain, inflammatory pain, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, menstrual pain; bladder disease, such as incontinence, micturition disorder, renal colic and cystitis; inflammation, such as burns, rheumatoid arthritis and osteoarthritis; neurodegenerative disease, such as stroke, post stroke pain and multiple sclerosis; pulmonary disease, such as asthma, cough, chronic obstructive pulmonary disease (COPD) and broncho constriction; gastrointestinal disease such as gastroesophageal reflux disease (GERD), dysphagia, ulcer, irritable bowel syndrome (IBS), inflammatory bowel disease (IBD), colitis and Crohn's disease; ischemia, such as cerebrovascular ischemia; emesis, such as cancer chemotherapy-induced emesis, and obesity, or the like in mammals, especially humans.

The compounds of the present invention are useful for the general treatment of pain, particularly neuropathic pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1–164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765–1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13–44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13–44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), posttraumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition, which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959–1964). The symptoms of neuropathic pain are difficult to treat, as they are often heterogeneous even between patients with the same disease (Woolf & Decosterd, 1999, Pain Supp., 6, S141–S147; Woolf and Mannion, 1999, Lancet, 353, 1959–1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45–56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397–407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679–686; McCarthy et al., 1994, Textbook of Pain, 387–395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

Also, the present invention provides a pharmaceutical composition for the treatment of disease conditions caused by overactivation of VR1 receptor, in a mammalian subject, which comprises administering to said subject a therapeutically effective amount of a compound of formula (I), or a pharmaceutically acceptable salt or solvate thereof. The composition is preferably useful for the treatment of the disease conditions defined above.

Also, the present invention provides for the use of a compound of formula (I), or a pharmaceutically acceptable salt or solvate thereof, as a medicament.

Further, the present invention provides a method for the treatment of the disease conditions defined above in a mammal, preferably a human, which comprises administering to said subject a therapeutically effective amount of a compound of formula (I).

Yet further, the present invention provides the use of a therapeutically effective amount of a compound of formula (I) in the manufacture of a medicament for the treatment of the disease conditions defined above.

Yet further, the present invention provides a combination of a compound of formula(I) and another pharmacologically active agent.

DETAILED DESCRIPTION OF THE INVENTION

As used herein, the term "a halogen atom" means a fluoro, a chloro, a bromo or an iodo atom, preferably a fluoro or a chloro atom.

As used herein, the term "a $(C_1-C_6)$alkyl group" means straight or branched chain saturated radicals, including, but not limited to methyl, ethyl, n-propyl, iso-propyl, n-butyl, iso-butyl, secondary-butyl, tertiary-butyl and 2-methylbutyl groups. Preferable alkyl groups are methyl, ethyl, n-propyl, n-butyl, tertiary-butyl and 2-methylbutyl groups.

As used herein, the term "a $(C_1-C_3)$alkyl group" means straight or branched chain saturated radicals, including, but not limited to methyl, ethyl, n-propyl and iso-propyl. Preferable alkyl groups are methyl, ethyl and n-propyl.

As used herein, the term "a $(C_4-C_5)$alkyl group" means straight or branched chain saturated radicals, including, but not limited to n-butyl, isobutyl, secondary-butyl, tertiary-butyl and 2-methylbutyl groups. Preferable alkyl groups are n-butyl, tertiary-butyl and 2-methylbutyl groups.

As used herein, the term "a $(C_1-C_6)$alkyl group substituted with a piperidino group" means a $(C_1-C_6)$alkyl radical as defined above which is substituted with a piperidino group including, but not limited to, piperidinomethyl, piperidinoethyl or piperidinobutyl group.

As used herein, the term "a hydroxy$(C_1-C_6)$alkyl group" means a $(C_1-C_6)$alkyl radical as defined above which is substituted by hydroxy group including, but not limited to, hydroxymethyl, hydroxyethyl, hydroxy n-propyl, hydroxy iso-propyl, hydroxy n-butyl, hydroxy iso-butyl, hydroxy secondary-butyl and hydroxy tertiary-butyl. Preferable hydroxyalkyl groups are hydroxymethyl, hydroxyethyl, hydroxy n-propyl and hydroxy n-butyl.

As used herein, the term "a $(C_1-C_6)$alkoxy group" means $(C_1-C_6)$alkyl-O— wherein $(C_1-C_6)$alkyl radical as defined above, including, but not limited to methoxy, ethoxy, n-propoxy, iso-propoxy, n-butoxy, iso-butoxy, secondary-butoxy and tertiary-butoxy. Preferable alkoxy groups are methoxy, ethoxy, n-propoxy, n-butoxy and tertiary-butoxy.

As used herein, the term "a $(C_1-C_3)$alkoxy group" means $(C_1-C_3)$alkyl-O— wherein $(C_1-C_3)$alkyl radical as defined above, including, but not limited to methoxy, ethoxy, n-propoxy and iso-propoxy. Preferable alkoxy groups are methoxy, ethoxy and n-propoxy.

As used herein, the term "a $(C_1-C_6)$alkoxy group optionally substituted with a 3–7 membered carbocyclic ring" means a $(C_1-C_6)$alkoxy radical as defined above which is unsubstituted or substituted with a 3–7 membered carbocyclic ring defined below such as a cyclopropyl, cyclobutyl, cyclopentyl, cyclohexyl or cycloheptyl ring.

As used herein, the term "a hydroxy$(C_1-C_6)$alkoxy group" means a $(C_1-C_6)$alkoxy radical as defined above which is substituted by hydroxy group including, but not limited to, hydroxymethoxy, hydroxyethoxy, hydroxy n-propoxy, hydroxy iso-propoxy, hydroxy n-butoxy, hydroxy iso-butoxy, hydroxy secondary-butoxy and hydroxy tertiary-butoxy. Preferable hydroxyalkoxy groups are hydroxymethoxy, hydroxyethoxy, hydroxy n-propoxy and hydroxy n-butoxy.

As used herein, the term "a $(C_1-C_6)$alkoxy-$(C_1-C_6)$alkyl group" means a $(C_1-C_6)$alkoxy radical as defined above which is substituted by a $(C_1-C_6)$alkyl group as defined above.

As used herein, the term "a $(C_1-C_6)$alkoxy-$(C_1-C_6)$alkoxy group" means a $(C_1-C_6)$alkoxy radical as defined above which is substituted by a $(C_1-C_6)$alkoxy group as defined above. Preferable alkoxy-alkoxy groups are methoxy methoxy, methoxy ethoxy or ethoxy ethoxy groups.

As used herein the term "a halo($C_1$–$C_6$)alkyl group", means a ($C_1$–$C_6$)alkyl radical which is substituted by one or more halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trifluoro-1,1-dimethylethyl 2,2,2-trichloroethyl, 3-fluoropropyl, 4-fluorobutyl, chloromethyl, trichloromethyl, iodomethyl, bromomethyl and 4,4,4-trifluoro-3-methylbutyl groups. Preferable halo($C_1$–$C_6$)alkyl groups are fluoromethyl, difluoromethyl, trifluoromethyl, 2-fluoroethyl, 2,2-difluoroethyl, 2,2,2-trifluoroethyl and 2,2,2-trifluoro-1,1-dimethylethyl groups.

As used herein the term "a halo($C_1$–$C_4$)alkyl group", means a ($C_1$–$C_4$)alkyl radical which is substituted by one or more halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trifluoro-1,1-dimethylethyl 2,2,2-trichloroethyl, 3-fluoropropyl, 4-fluorobutyl, chloromethyl, trichloromethyl, iodomethyl and bromomethyl groups. Preferable halo ($C_1$–$C_4$)alkyl groups are fluoromethyl, difluoromethyl, trifluoromethyl, 2-fluoroethyl, 2,2-difluoroethyl, 2,2,2-trifluoroethyl and 2,2,2-trifluoro-1,1-dimethylethyl groups.

As used herein, the term "a ($C_1$–$C_6$)alkylthio group" means ($C_1$–$C_6$)alkyl-S— wherein ($C_1$–$C_6$)alkyl is as defined above, including, but not limited to methylthio, ethylthio, n-propylthio, iso-propylthio, n-butylthio, iso-butylthio, secondary-butylthio and tertiary-butylthio. Preferable alkylthio groups are methylthio, ethylthio, n-propylthio and n-butylthio.

As used herein, the term "a ($C_1$–$C_6$)alkylsulfinyl group" means ($C_1$–$C_6$)alkyl-SO— wherein ($C_1$–$C_6$)alkyl is defined above, including, but not limited to methylsulfinyl, ethylsulfinyl, n-propylsulfinyl, iso-propylsulfinyl, n-butylsulfinyl, iso-butylsulfinyl, secondary-butylsulfinyl and tertiary-butylsulfinyl. Preferable alkylsulfinyl groups are methylsulfinyl, ethylsulfinyl, n-propylsulfinyl and n-butylsulfinyl.

As used herein, the term "a ($C_1$–$C_6$)alkylsulfonyl group" means ($C_1$–$C_6$)alkyl-$SO_2$— wherein ($C_1$–$C_6$)alkyl is defined above, including, but not limited to methylsulfonyl, ethylsulfonyl, n-propylsulfonyl, iso-propylsulfonyl, n-butylsulfonyl, iso-butylsulfonyl, secondary-butylsulfonyl, tertiary-butylsulfonyl. Preferable alkylsulfonyl groups are methylsulfonyl, ethylsulfonyl, n-propylsulfonyl, n-butylsulfonyl.

As used herein, the term "carbocyclic ring" means a saturated carbocyclic ring of 3 to 7 carbon atoms including, but not limited to, cyclopropyl, cyclobutyl, cyclopentyl, cyclohexyl, cycloheptyl. Preferable carbocyclic rings are cyclopropyl, cyclopentyl and cyclohexyl.

As used herein the term "heterocyclic ring" means a 3–8 membered carbocyclic ring in which one or two non-adjacent carbon atoms are optionally replaced by oxygen, sulfur, NH or N($C_1$–$C_6$)alkyl group. Examples of such heterocyclic rings include, but are not limited to, tetrahydrofuran, tetrahydrothiophen, tetrahydrothiazole, tetrahydropyrrole, tetrahydropyran, tetrahydropyridine, tetrahydroprazine, tetrahydropyrimidine and 3,4-dihydro-2H-pyran. Preferable heterocyclic rings are tetrahydrofuran, tetrahydrothiophen, tetrahydropyrrole, tetrahydropyridine and 3,4-dihydro-2H-pyran.

Where the compounds of formula (I) contain hydroxy groups, they may form esters. Examples of such esters include esters with a carboxy group. The ester residue may be an ordinary protecting group or a protecting group which can be cleaved in vivo by a biological method such as hydrolysis.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

Preferable compounds of the invention include those in which each variable in Formula (I) is selected from the preferred group for each variable.

Preferable compounds of the invention include compounds according to formula(I), wherein $R^1$ represents a methyl group; $R^2$ represents a hydrogen atom, a halogen atom, a ($C_1$–$C_6$)alkyl group or a ($C_1$–$C_6$)alkoxy group; $R^3$, $R^4$, $R^5$ and $R^6$ each independently represents a hydrogen atom, a ($C_1$–$C_6$)alkyl, or a halogen atom; $R^7$ represents a hydrogen atom, a halogen atom, a hydroxy group, a ($C_1$–$C_6$) alkyl group substituted with a piperidino group or a ($C_1$–$C_6$) alkoxy group substituted with a 3–7 membered carbocyclic ring; $R^8$ represents a ($C_1$–$C_6$)alkyl group or a halo ($C_1$–$C_6$) alkyl group; or $R^7$ and $R^8$, when adjacent to each other, taken together with the carbon atoms to which they are attached form a 5–6 membered carbocyclic or heterocyclic ring, wherein the carbocyclic ring or the heterocyclic ring is unsubstituted or substituted with one or more ($C_1$–$C_6$)alkyl groups; and $R^9$ represents a hydrogen atom or a halogen atom; or a pharmaceutically acceptable salt or solvate thereof.

Preferable compounds of the invention include compounds according to formula(I), wherein $R^1$ represents a methyl group; $R^2$ represents a hydrogen atom, a halogen atom, a ($C_1$–$C_3$)alkyl group or a ($C_1$–$C_3$)alkoxy group; $R^3$ represents a hydrogen atom or a methyl group; $R^4$ represents a hydrogen atom; $R^5$ and $R^6$ each independently represents a hydrogen atom or a halogen atom; $R^7$ represents a hydrogen atom, a halogen atom, a hydroxy group, a ($C_1$–$C_6$)alkyl group substituted with a piperidino group or a ($C_1$–$C_6$) alkoxy group substituted with a 3–7 membered carbocyclic ring; $R^8$ represents a ($C_4$–$C_5$)alkyl group or a halo($C_1$–$C_4$) alkyl group; or $R^7$ and $R^8$, when adjacent to each other, taken together with the carbon atoms to which they are attached form a 5–6 membered carbocyclic ring or a 6 membered heterocyclic ring containing an oxygen atom, wherein the carbocyclic ring or the heterocyclic ring is substituted with one or more ($C_1$–$C_6$)alkyl groups; and $R^9$ represents a hydrogen atom or a halogen atom; or a pharmaceutically acceptable salt or solvate thereof.

Preferable compounds of the invention include compounds according to formula(I), wherein $R^1$ represents a methyl group; $R^2$ represents a hydrogen atom, a chloro atom, a fluoro atom, or a methyl group; $R^3$ represents a hydrogen atom or a methyl group; $R^4$ represents a hydrogen atom; $R^5$ and $R^6$ each independently represents a hydrogen atom or a halogen atom; $R^7$ represents a hydrogen atom, a chloro atom, a fluoro atom, a hydroxy group, a ($C_1$–$C_6$)alkyl group substituted with a piperidino group or a ($C_1$–$C_6$) alkoxy group substituted with a 3–7 membered carbocyclic ring; $R^8$ represents a tert-butyl group, a trifluoromethyl group or a 2,2,2-trifluoro-1,1-dimethylethyl group; or $R^7$ and $R^8$, when adjacent to each other, taken together with the carbon atoms to which they are attached form 3,4-dihydro-2H-pyran or cyclopentane substituted with one or more methyl groups; and $R^9$ represents a hydrogen atom or a halogen atom; or a pharmaceutically acceptable salt or solvate thereof.

Preferable compounds of the invention include compounds according to formula(I), wherein $R^1$ represents a methyl group; $R^2$ represents a hydrogen atom, a fluoro atom or a methyl group; $R^3$ represents a hydrogen atom or a methyl group; $R^4$, $R^5$ and $R^6$ each represents a hydrogen atom; $R^9$ represents a hydrogen atom; and (1) $R^7$ represents a hydrogen atom, a fluoro atom, a chloro atom or a piperidinomethyl group, and $R^8$ represents a tert-butyl group;
(2) $R^7$ represents a hydrogen atom, and $R^8$ represents a 2,2,2-trifluoro-1,1-dimethylethyl group;
(3) $R^7$ represents a chloro atom, and $R^8$ represents a trifluoromethyl group; —or
(4) $R^7$ and $R^8$, when adjacent to each other, taken together with the carbon atoms to which they are attached form 1,1-dimethylcyclopentane.

Preferable compounds of the invention include compounds according to formula(I), wherein $R^1$ represents a methyl group; $R^2$ represents a fluoro atom; $R^3$, $R^4$, $R^5$ and $R^6$ each represents a hydrogen atom; $R^7$ represents a fluoro atom and $R^8$ represents a tert-butyl group; or $R^7$ and $R^8$, when adjacent to each other, taken together with the carbon atoms to which they are attached form cyclohexane substituted with one or more methyl groups; and $R^9$ represents a hydrogen atom.

A preferred compound of the present invention is selected from:

2-(4-tert-Butyl-3-chlorophenoxy)-N-{3-fluoro-4-[(methylsulfonyl)amino]benzyl}acetamide;

2-(4-tert-Butyl-3-chlorophenoxy)-N-((1R)-1-{4-[(methyisulfonyl)amino]phenyl}ethyl)acetamide;

2-(4-tert-Butyl-3-chlorophenoxy)-N-((1R)-1-{3-fluoro-4-[(methylsulfonyl)amino]phenyl}ethyl)acetamide;

2-(4-tert-Butyl-3-chlorophenoxy)-N-((1R)-1-{3-methyl-4-[(methylsulfonyl)amino]phenyl}ethyl)acetamide;

2-(4-tert-Butyl-3-fluorophenoxy)-N-((1R)-1-{4-[(methylsulfonyl)amino]phenyl}ethyl)acetamide;

2-(4-tert-Butyl-3-fluorophenoxy)-N-((1R)-1-{3-fluoro-4-[(methylsulfonyl)amino]phenyl}ethyl)acetamide;

2-(4-tert-Butyl-3-fluorophenoxy)-N-{3-methyl-4-[(methylsulfonyl)amino]benzyl}acetamide;

2-(4-tert-Butyl-3-fluorophenoxy)-N-((1R)-1-{3-methyl-4-[(methylsulfonyl)amino]phenyl}ethyl)acetamide;

2-[(1,1-Dimethyl-2,3-dihydro-1H-inden-5-yl)oxy]-N-{3-fluoro-4-[(methylsulfonyl)amino]benzy}acetamide;

2-(4-tert-Butylphenoxy)-N-{3-methyl-4-[(methylsulfonyl)amino]benzyl}acetamide;

2-[4-tert-Butyl-2-(piperidin-1-ylmethyl)phenoxy]-N-((1R)-1-{3-methyl-4-[(methylsulfonyl)amino]phenyl}ethyl)acetamide;

2-(4-tert-Butylphenoxy)-N-((1R)-1-{3-methyl-4-[(methylsulfonyl)amino]phenyl}ethyl)acetamide;

N-((1R)-1-{3-Methyl-4-[(methylsulfonyl)amino]phenyl}ethyl)-2-[4-(2,2,2-trifluoro-1,1dimethylethyl)phenoxy]acetamide;

2-(4-tert-Butylphenoxy)-N-((1R)-1-{4-[(methylsulfonyl)amino]phenyl}ethyl)acetamide;

2-[3–Chloro-4-(trifluoromethyl)phenoxy]-N-{3-methyl-4-[(methylsulfonyl)amino]benzyl}acetamide;

2-(4-tert-Butyl-3-hydroxyphenoxy)-N-((1R)-1-{3-methyl-4-[(methylsulfonyl)amino]phenyl}ethyl)acetamide;

2-(4-tert-Butyl-3-fluorophenoxy)-N-{3-fluoro-4-[(methylsulfonyl)amino]benzyl}acetamide; and 2-[(5,5-Dimethyl-5,6,7,8-tetrahydronaphthalen-2-yl)oxy]-N-{3-fluoro-4-[(methylsulfonyl)amino]benzyl}acetamide; or a pharmaceutically acceptable salt or solvate thereof.

General Synthesis

The compounds of the present invention may be prepared by a variety of processes well known for the preparation of compounds of this type, for example as shown in the following reaction scheme. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1999).

The following reaction scheme illustrates the preparation of compounds of formula (I).

Scheme 1:
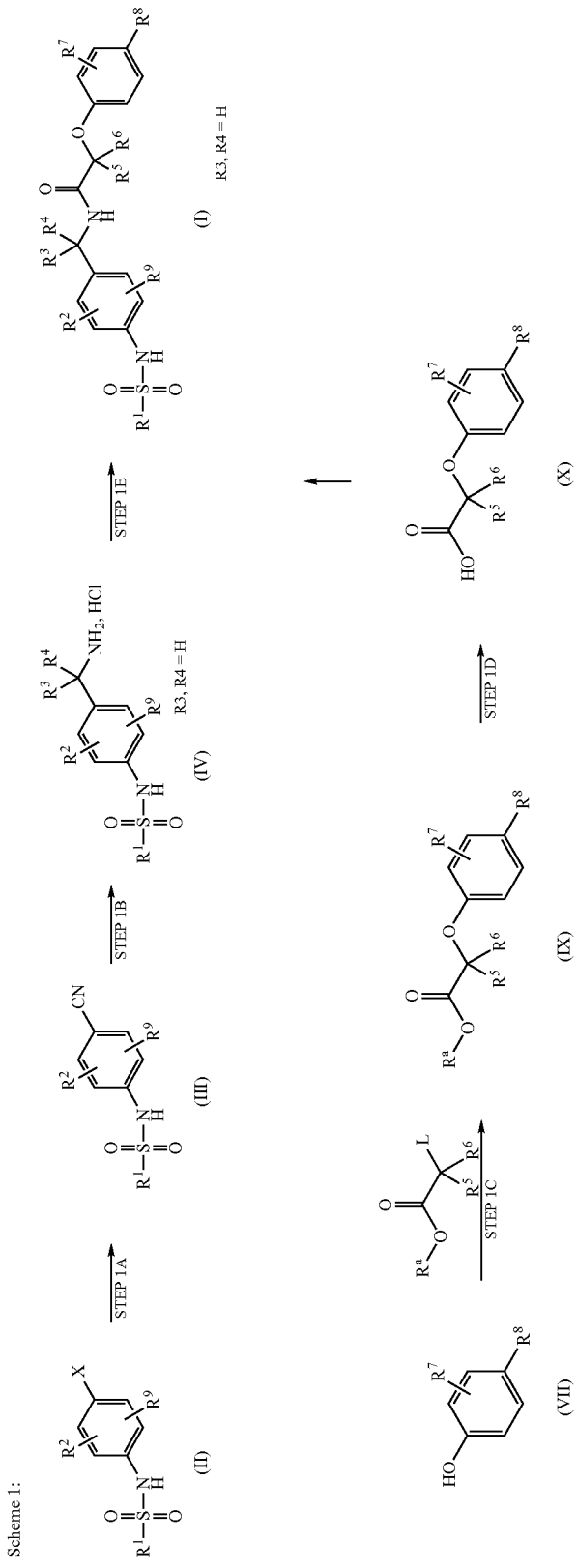

In the above formula, R$^a$ represents an alkyl group having from 1 to 4 carbon atoms or a benzyl group; X represents a halogen atom such as chlorine, or a sulfoxy group; and L represents a leaving group. Examples of suitable leaving groups L include a halogen atom such as chlorine, bromine or iodine.

Step 1A

In this step, the compound of formula (III) can also be prepared by cyanating of the compound of formula (II) under cyanation conditions with a transition metal catalyst and metal cyanide reagent in an inert solvent.

Examples of suitable solvents include: tetrahydrofuran (THF); 1,4-dioxane; N,N-dimethylformamide; acetonitrile; alcohols such as methanol or ethanol; halogenated hydrocarbons such as dichloromethane, 1,2-dichloroethane, chloroform or carbon tetrachloride; and acetic acid. Suitable reagents include, for example, alkali metal cyanide such as lithium cyanide, sodium cyanide and potassium cyanide; transition metal cyanide such as iron(II) cyanide, cobalt(II) cyanide, copper(I) cyanide, copper(II) cyanide, zinc(II) cyanide, sodium borohydride cyanide and trimethylsilyl cyanide.

This reaction can be carried out in the presence of a suitable catalyst. There is no particular restriction on the nature of the catalyst used, and any catalyst commonly used in reactions of this type can equally be used here. Examples of such catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(I) trifluoromethanesulfonate, palladium(II) acetate, palladium(II) chloride, bisacetonitriledichloropalladium(0), bis(dibenzylideneacetone)palladium(0), tris(dibenzylideneacetone)dipalladium(0) or [1,1'-bis(diphenylphosphino)ferrocene]palladium(II) dichloride. Preferable catalysts are tetrakis(triphenylphosphine)-palladium, bis (triphenylphosphine)palladium(II) chloride, palladium(II) acetate, palladium(II) chloride, bisacetonitriledichloropalladium(0), bis(dibenzylideneacetone)palladium(0), tris(dibenzylideneacetone)dipalladium(0) or [1,1'-bis(diphenylphosphino)ferrocene]palladium(II) dichloride.

This reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl or triphenylarsine.

The reaction can be carried out at a temperature of from 0° C. to 200° C., more preferably from 20° C. to 120° C. Reaction time is, in general, from 5 minutes to 48 hours, more preferably 30 minutes to 24 hours, will usually suffice.

Step 1B

In this step, the compounds of formula (IV) can be prepared by a hydrogenation reaction with a compound of formula (III) under, for example, known hydrogenolysis conditions in the presence of a metal catalyst under hydrogen atmosphere or in the presence of hydrogen sources such as formic acid or ammonium formate in an inert solvent. If desired, the reaction is carried out under acidic conditions, for example, in the presence of hydrochloric acid or acetic acid. A preferred metal catalyst is selected from, for example, nickel catalysts such as Raney nickel; palladium-carbon; palladiumhydroxide-carbon; platinumoxide; platinum-carbon; ruthenium-carbon; rhodium-aluminumoxide; and tris[triphenyphosphine] rhodiumchloride. Examples of suitable inert aqueous or non-aqueous organic solvents include: alcohols, such as methanol, ethanol; ethers, such as tetrahydrofuran or dioxane; acetone; dimethylformamide; halogenated hydrocarbons, such as dichloromethane, dichloroethane or chloroform; and acetic acid or mixtures thereof. The reaction can be carried out at a temperature in the range from of 20° C. to 100° C., preferably in the range of 20° C. to 60° C. Reaction time is, in general, from 10 minutes to 48 hours, preferably 30 minutes to 24 hours. This reaction can be carried out under hydrogen atmosphere at a pressure ranging from 1 to 100 atm, preferably from 1 to 10 atm.

Step 1C

In this step, a compound of formula (IX) can be prepared by a substitution reaction of the compound of formula (VII) with a compound of formula (VII) (commercially available) in the presence of a base in an inert solvent. Examples of suitable solvents include: tetrahydrofuran, N,N-dimethylformamide, dimethylsulfoxide, diethylether, toluene, ethylene glycol dimethylether or 1,4-dioxane. Preferred solvents are tetrahydrofuran, N,N-dimethylformamide, dimethylsulfoxide and 1,4-dioxane. Examples of suitable bases include: alkyl lithiums, such as nbutyllithium, sec-butyllithium or tert-butyllithium; aryllithiums, such as phenyllithium or lithium naphthylide; metalamide such as sodium amide or lithium diisopropylamide; and alkali metal, such as potassium hydride, sodium hydride or alkali carbonate, such as potassium carbonate or sodium carbonate. Preferred bases are n-butyllithium, tert-butyllithium, potassium hydride and potassium carbonate. This reaction can be carried out at a temperature in the range from −50° C. to 200° C., usually from 0° C. to 80° C. for 5 minutes to 72 hours, usually 30 minutes to 24 hours.

Step 1D

In this step, an acid compound of formula (X) can be prepared by hydrolysis of the ester compound of formula (IX) in a solvent.

The hydrolysis can be carried out by conventional procedures. In a typical procedure, the hydrolysis is carried out under basic conditions, e.g., in the presence of sodium hydroxide, potassium hydroxide or lithium hydroxide. Suitable solvents include, for example, alcohols such as methanol, ethanol, propanol, butanol, 2-methoxyethanol, and ethylene gylcol; ethers such as tetrahydrofuran (THF), 1,2-dimethoxyethane (DME), and 1,4-dioxane; amides such as N,N-dimethylformamide (DMF) and hexamethylphosphorictriamide; and sulfoxides such as dimethyl sulfoxide (DMSO). Preferable solvents are methanol, ethanol, propanol, tetrahydrofuran (THF), 1,2-dimethoxyethane (DME), 1,4-dioxane, N,N-dimethylformamide (DMF), and dimethyl sulfoxide (DMSO). This reaction can be carried out at a temperature in the range from −20 to 100° C., usually from 20° C. to 65° C. for 30 minutes to 24 hours, usually 60 minutes to 10 hours.

The hydrolysis can also be carried out under acidic conditions, e.g., in the presence of hydrogen halides, such as hydrogen chloride and hydrogen bromide; sulfonic acids, such as p-toluenesulfonic acid and benzenesulfonic acid; pyridium p-toluenesulfonate; and carboxylic acids, such as acetic acid and trifluoroacetic acid. Suitable solvents include, for example, alcohols such as methanol, ethanol, propanol, butanol, 2-methoxyethanol, and ethylene gylcol; ethers such as tetrahydrofuran (THF), 1,2-dimethoxyethane (DME), and 1,4-dioxane; amides such as N,Ndimethylformamide (DMF) and hexamethylphosphorictriamide; and sulfoxides such as dimethyl sulfoxide (DMSO). Preferable solvents are methanol, ethanol, propanol, tetrahydrofuran (THF), 1,2-dimethoxyethane (DME), 1,4-dioxane, N,N-dimethylformamide (DMF), and dimethyl sulfoxide (DMSO). This reaction can be carried out at a temperature in the range from −20 to 100° C., usually from 20° C. to 65° C. for 30 minutes to 24 hours, usually 60 minutes to 10 hours.

Step 1E

In this step, an amide compound of formula (I) can be prepared by coupling reaction of the acid compound of formula (X) with an amine compound of formula (IV) in the presence or absence of a coupling reagent in an inert solvent. This reaction can be carried out through activated carboxylic derivatives.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone, nitromethane, DMF, sulfolane, DMSO, N-methyl pirrolidon (NMP), 2-butanone and acetonitrile; halogenated hydrocarbons, such as dichloromethane, dichloroethane and chloroform; and ethers, such as tetrahydrofuran and 1,4-dioxane.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction at a temperature of from −20° C. to 100° C., more preferably from about 0° C. to 60° C. The time required for the reaction can also vary widely, depending on many factors, notably the reaction temperature and the nature of the reagents and solvent employed. However, provided that the reaction is effected under the preferred conditions outlined above, a period of 5 minutes to 1 week, more preferably 30 minutes to 24 hours, will usually suffice.

Suitable coupling reagents are those typically used in peptide synthesis including, for example, diimides (e.g., dicyclohexylcarbodiimide (DCC), 1-ethyl-3-(3'-dimethylaminopropyl)carbodiimide hydrochloride (EDC)), 2-ethoxy-N-ethoxycarbonyl-1,2-dihydroquinoline, 2-bromo-1-ethylpyridinium tetrafluoroborate (BEP), 2-chloro-1,3-dimethylimidazolinium chloride (CDI), benzotriazol-1-yloxy-tris(dimethylamino)phosphonium hexafluorophosphate (BOP), diethyl azodicarboxylate-triphenylphosphine, diethylcyanophosphate, diethylphosphorylazide, 2-chloro-1-methylpyridinium iodide, N,N'-carbonyldiimidazole, benzotriazol-1-yl diethyl phosphate, ethyl chloroformate or isobutyl chloroformate.

The reaction can be carried out in the presence of a base such as 1-hydroxybenzotriazole (HOBt), N,N-diisopropylethylamine, N-methylmorpholine and triethylamine. The amide compound of formula (I) can be formed via an acylhalide, which can be obtained by the reaction with halogenating agents such as oxalylchloride, phosphorus oxychloride and thionyl chloride. The resulting acylhalide can be converted to the corresponding amide compound by treating with the amine compound of formula (IV) under the similar conditions as described in this step.

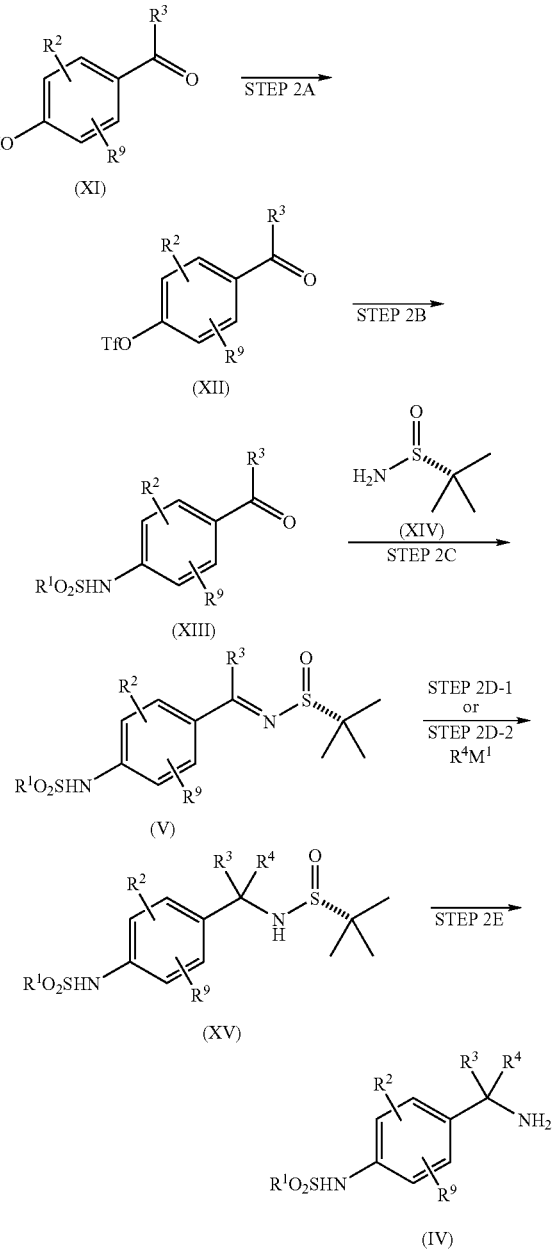

Step 2A

In this step, the compound of formula (XII) can be prepared by triflic reaction of the compound of formula (XI) using triflic anhydrate under basic conditions in an inert solvent. "Tf" represents trifluoromethylsulfonyl group.

A preferred base is, for example, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, 2,6-lutidine, pyridine or dimethylaminopyridine.

Examples of suitable solvents include: tetrahydrofuran, 1,4-dioxane, N,N-dimethylformamide and acetonitrile; alcohols, such as methanol or ethanol; halogenated hydrocarbons, such as dichloromethane, 1,2-dichloroethane, chloroform or carbon tetrachloride; and acetic acid.

Reaction temperature is generally in the range of −78 to 200° C., preferably in the range of from 0° C. to room temperature. Reaction time is, in general, from 1 minute to a day, preferably from 1 hour to 20 hours.

Step 2B

In this step, the compound of formula (XIII) can be prepared by a coupling reaction of the compound of a formula (XII) with alkyl sulfonamide under basic condisions with catalyst and Xantphos in an inert solvent as described in Buchwald, S. L., Journal of the American Chemical Society, 2002, 124, 6043–6048.

Examples of suitable catalysts include tris(dibenzylidenacetone)dipalladium(0) and palladium reagents, such as palladium acetate and palladium dibenzylacetone.

A preferred base is selected from, for example, but not limited to, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, cesium carbonate, potassium fluoride, sodium hydride or potassium hydride, or an amine such as triethylamine, tributylamine, diisopropylethylamine, 2,6-lutidine, pyridine or dimethylaminopyridine.

Examples of suitable solvents include: tetrahydrofuran, 1,4-dioxane, N,N-dimethyiformamide and acetonitrile; alcohols, such as methanol or ethanol; halogenated hydrocarbons, such as dichloromethane, 1,2-dichloroethane, chloroform or carbon tetrachloride and acetic acid Reaction temperature is generally in the range of 0 to 200° C., preferably in the range of from 100° C. to 140° C. Reaction time is, in general, from 1 minute to a day, preferably from 5 minutes to 1 hour.

Step 2C

In this step, the compound of formula (V) can be prepared by dehydration of the compound of a formula (XIII) and sulfimamide of formula (XIV) with catalyst in an inert solvent.

The dehydration reaction is conducted in the presence of a dehydrating agent. Examples of a suitable dehydrating agents include: hydrogen halides, such as hydrogen chloride and hydrogen bromide; sulfonic acids, such as p-toluenesulfonic acid and benzenesulfonic acid; sulfonylchloride, such as methansulfonylchloride and p-toluenesulfonylchloride; methoxycarbonylsulfamoyltriethylammonium hydroxide; p-toluenesulfonylisocyanate and titanium(IV) ethoxide.

Reaction temperature is generally in the range of 0 to 200° C., preferably in the range of from 50° C. to 100° C. Reaction time is, in general, from 1 minute to 48 hours, preferably from 12 hours to 24 hours.

Step 2D-1

In this step, the compound of formula (XV) can be prepared by reduction of the compound of a formula (V) with reducing in an inert solvent.

The reduction may be carried out in the presence of a suitable reducing agent in an inert solvent or without solvent. A preferred reducing agent is, for example, $NaBH_4$, $LiAlH_4$, $LiBH_4$, Fe, Sn or Zn.

Reaction temperature is generally in the range of −78° C. to room temprature, preferably in the range of from −70° C. to 0° C. Reaction time is, in general, from 1 minute to a day, preferably from 3 hours to 6 hours.

Examples of suitable solvents include: tetrahydrofuran, 1,4-dioxane, N,N-dimethylformamide, acetonitrile; alcohols, such as methanol or ethanol; halogenated hydrocarbons, such as dichloromethane, 1,2-dichloroethane, chloroform or carbon tetrachloride and acetic acid.

Step 2D-2

In this step, the organometallic compound of formula $R^4M^1$ can be prepared by reaction of a halide compound of $R^4$ as defined above. $M^1$ represents metal such as lithium, or MgY, wherein Y represents a hydrogen atom or a halogen atom such as fluorine, chlorine, bromine or iodine. This reaction may be carried out in the presence of an organometallic reagent or a metal. Examples of suitable organometallic reagents include: alkyllithiums such as n-butyllithium, sec-butyllithium and tert-butyllithium and aryllithiums such as phenyllithium and lithium naphthylide. Examples of suitable metals include magnesium. Preferred reaction inert solvents include, for example, hydrocarbons, such as hexane; ethers, such as diethyl ether, diisopropyl ether, 1,2-dimethoxyethane (DME), tetrahydrofuran (THF) and dioxane; or mixtures thereof. Reaction temperature is generally in the range of −100 to 50° C., preferably in the range of from −100° C. to room temperature. Reaction time is, in general, from 1 minute to a day, preferably from 1 hour to 10 hours.

Step 2E

In this step, the compound of formula (IV) can be prepared by deprotection and salt formation of the compound of formula (XV) under acidic condition in an inert solvent using the method of D. Cogan et. al. Journal of the American Chemical Society, 1999, 121, 268–269.

Reaction temperature is generally in the range of 0 to 200° C., preferably room temperature. Reaction time is, in general, from 1 minute to 24 hours, preferably from 5 minutes to 1 hour.

Examples of suitable solvents include: tetrahydrofuran, 1,4-dioxane, N,N-dimethylformamide and acetonitrile; alcohols, such as methanol or ethanol; halogenated hydrocarbons, such as dichloromethane, 1,2-dichloroethane, chloroform or carbon tetrachloride; and acetic acid.

The starting materials in the aforementioned general syntheses are commercially available or may be obtained by conventional methods known to those skilled in the art.

The compounds of formula (I), and the intermediates in the above-mentioned preparation methods can be isolated and purified by conventional procedures, such as recrystallization or chromatographic purification.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

Method for Assessing Biological Activities:

Human VR1 Antagonist Assay

VR1 antagonistic activity can be determined by the $Ca^{2+}$ imaging assay using human VR1 highly expressing cells. The cells that highly express human VR1 receptors are obtainable from several different conventional methods. The one standard method is cloning from human Dorsal Root Ganglion (DRG) or kidney according to the methods such as described in the journal article; Nature, 389, pp816–824, 1997. Alternatively VR1 receptors highly expressing human keratinocytes are also known and published in the journal article (Biochemical and Biophysical Research Communications, 291, pp124–129, 2002). In this article, human keratinocytes demonstrated VR1 mediated intracellular $Ca^{2+}$ increase by addition of capsaicin. Furthermore, the method to upregulate human VR1 gene, which is usually a silent gene or doesn't produce detectable levels of VR1 receptors, is also available to obtain propriety cells. Such genetic modification method was described in detail in Nat. Biotechnol., 19, pp440–445, 2001.

The cells that express human VR1 receptors were maintained in a culture flask at 37° C. in an environment containing 5% $CO_2$ until use in the assay. The intracellular $Ca^{2+}$ imaging assay to determine VR1 antagonistic activities were done by the following procedure.

The culture medium was removed from the flask and fura-2/ AM fluorescent calcium indicator was added to the flask at a concentration of 5 µM in the medium. The flask was placed in a $CO_2$ incubator and incubated for 1 hour. Then the cells expressing the human VR1 receptors were detached from the flask followed by washing with phosphate buffer saline, PBS(−) and re-suspended in assay buffer. An 80 µl of aliquot of cell suspension ($3.75 \times 10^5$ cells/ml) was added to the assay plate and the cells were spun down by centrifuge (950 rpm, 200° C., 3 minutes).

Capsaicin Stimulation Assay

The capsaicin-induced changes in the intracellular calcium concentration were monitored using FDSS 6000 (Hamamatsu Photonics, Japan), a fluorometric imaging system. The cell suspension in Krebs-Ringer HEPES (KRH) buffer (115 mM NaCl, 5.4 mM KCl, 1 mM $MgSO_4$, 1.8 mM $CaCl_2$, 11 mM D-glucose, 25 mM HEPES, 0.96 mM $Na_2HPO_4$, pH 7.3) was pre-incubated with varying concentrations of the test compounds or KRH buffer (buffer control) for 15 minutes at room temperature under dark conditions. Then, capsaicin solution, which gives 300 nM in assay mixture, was automatically added to the assay plate by the FDSS 6000.

Acid Stimulation Assay

The acid-induced changes in the intracellular calcium concentration were monitored using FDSS 6000 (Hamamatsu Photonics, Japan), a fluorometric imaging system. The cell suspension in resting buffer (HBSS supplemented with 10 mM HEPES, pH 7.4) was pre-incubated with varying concentrations of the test compounds or resting buffer (buffer control) for 15 minutes at room temperature under the dark conditions. The cells were automatically added to the stimulating solution (HBSS supplemented with MES, final assay buffer pH5.8) by the FDSS 6000. The $IC_{50}$ values of VR1 antagonists were determined from half of the increase demonstrated by buffer control samples after acidic stimulation.

Determination of Antagonist Activity

The monitoring of the changes in the fluorescence signals (πex=340 nm–380 nm, πem=510–520 nm) was initiated at 1 minute prior to the addition of capsaicin solution or acidic buffer and continued for 5 minutes. The $IC_{50}$ values of VR1 antagonists were determined from the half of the increase demonstrated by buffer control samples after agonist stimulation.

Chronic Contriction Injury Model (CCI Model)

Male Sprague-Dawley rats (270–300 g; B. W., Charles River, Tsukuba, Japan) were used. The chronic constriction injury (CCI) operation was performed according to the method described by Bennett and Xie (Bennett, G. J. and Xie, Y. K. Pain, 33:87–107, 1988). Briefly, animals were anesthetized with sodium pentobarbital (64.8 mg/kg, i.p.) and the left common sciatic nerve was exposed at the level of the middle of the thigh by blunt dissection through biceps femoris. Proximal to the sciatic's trifurcation was freed of adhering tissue and 4 ligatures (4-0 silk) were tided loosely around it with about 1 mm space. Sham operation was performed as same as CCI surgery except for sciatic nerve ligation. Two weeks after surgery, mechanical allodynia was evaluated by application of von Frey hairs (VFHs) to the plantar surface of the hind paw. The lowest amount of force of VFH required to elicit a response was recorded as paw withdrawal threshold (PWT). VFH test was performed at 0.5, 1 and 2 hr post-dosing. Experimental data were analyzed using Kruskal-Wallis test followed by Dunn's test for multiple comparisons or Mann-Whitney U-test for paired comparison.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.75 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consisted of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media was removed and test compound solution (10 µM) in buffer was added to the apical compartment. The inserts were moved to wells containing fresh basolateral buffer and incubated for 1 hr. Drug concentration in the buffer was measured by LC/MS analysis.

Flux rate (F, mass/time) was calculated from the slope of cumulative appearance of substrate on the receiver side and apparent permeability coefficient ($P_{app}$) was calculated from the following equation.

$$P_{app}(cm/sec) = (F*VD)/(SA*MD)$$

where SA is surface area for transport (0.3 cm$^2$), VD is the donor volume (0.3 ml), MD is the total amount of drug on the donor side at t=0. All data represent the mean of 2 inserts. Monolayer integrity was determined by Lucifer Yellow transport.

Human Dofetilide Binding

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells were homogenized using a Polytron homogenizer (at the maximum power for 20 seconds) and centrifuged at 48,000 g for 20 minutes at 4° C. The pellet was resuspended, homogenized and centrifuged once more in the same manner. The resultant supernatant was discarded and the final pellet was resuspended (10-fold volume of 50 mM Tris buffer) and homogenized at the maximum power for 20 seconds. The membrane homogenate was aliquoted and stored at −80° C. until use. An aliquot was used for protein concentration determination using a Protein Assay Rapid Kit and ARVO SX plate reader (Wallac). All the manipulation, stock solution and equipment were kept on ice at all time. For saturation assays, experiments were conducted in a total volume of 200 μl. Saturation was determined by incubating 20 μl of [$^3$H]-dofetilide and 160 μl of membrane homogenates (20–30 μg protein per well) for 60 min at room temperature in the absence or presence of 10 μM dofetilide at final concentrations (20 μl) for total or nonspecific binding, respectively. All incubations were terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity was quantified by liquid scintillation counting using Packard LS counter.

For the competition assay, compounds were diluted in 96 well polypropylene plates as 4-point dilutions in semi-log format. All dilutions were performed in DMSO first and then transferred into 50 mM Tris buffer (pH 7.5 at 25° C.) containing 1 mM $MgCl_2$, 10 mM KCl so that the final DMSO concentration became equal to 1%. Compounds were dispensed in triplicate in assay plates (4 μl). Total binding and nonspecific binding wells were set up in 6 wells as vehicle and 10 μM dofetilide at final concentration, respectively. The radioligand was prepared at 5.6× final concentration and this solution was added to each well (36 μl). The assay was initiated by addition of YSi poly-L-lysine Scintillation Proximity Assay (SPA) beads (50 μl, 1 mg/well) and membranes (110 μl, 20 μg/well). Incubation was continued for 60 min at room temperature. Plates were incubated for a further 3 hours at room temperature for beads to settle. Receptor-bound radioactivity was quantified by counting Wallac MicroBeta plate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical Journal, 74, pp230–241). Before the day of experimentation, the cells were harvested from culture flasks and plated onto glass coverslips in a standard Minimum Essential Medium (MEM) medium with 10% Fetal Calf Serum (FCS). The plated cells were stored in an incubator at 37° C. maintained in an atmosphere of 95% $O_2$/5% $CO_2$. Cells were studied between 15–28 hrs after harvest.

HERG currents were studied using standard patch clamp techniques in the whole-cell mode. During the experiment the cells were superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings was made using a patch clamp amplifier and patch pipettes which have a resistance of 1–3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MW and seal resistances>1 GW was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol was applied to the cell to evoke membrane currents. The voltage protocol is as follows. The membrane was depolarized from a holding potential of −80 mV to +40 mV for 100 ms. This was followed by a descending voltage ramp (rate 0.5 mV msec$^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10–20 min by a peristalic pump. Provided there were minimal changes in the amplitude of the evoked current response in the vehicle control condition, the test compound of either 0.3, 1, 3, 10 μM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There was a subsequent wash period of a 10–20 min to assess reversibility. Finally, the cells were exposed to high dose of dofetilide (5 μM), a specific lKr blocker, to evaluate the insensitive endogenous current.

All experiments were performed at room temperature (23±1° C.). Evoked membrane currents were recorded on-line on a computer, filtered at 500–1 KHz (Bessel −3 dB) and sampled at 1–2 KHz using the patch clamp amplifier and a specific data analyzing software. Peak current amplitude, which occurred at around −40 mV, was measured off line on the computer.

The arithmetic mean of the ten values of amplitude was calculated under vehicle control conditions and in the presence of drug. Percent decrease of $I_N$ in each experiment was obtained by the normalized current value using the following formula: $I_N=(1-I_D/I_C)\times100$, where ID is the mean current value in the presence of drug and $I_C$ is the mean current value under control conditions. Separate experiments were performed for each drug concentration or time-matched control, and arithmetic mean in each experiment is defined as the result of the study.

Drug-drug Interaction Assay

This method essentially involves determining the percent inhibition of product formation from fluorescence probe at 3 μM of the each compound.

More specifically, the assay is carried out as follows. The compounds were pre-incubated with recombinant CYPs, 100 mM potassium phosphate buffer and fluorescence probe as substrate for 5 min. Reaction was started by adding a warmed NADPH generating system, which consist of 0.5 mM NADP (expect; for 2D6 0.03 mM), 10 mM $MgCl_2$, 6.2 mM DL-lsocitric acid and 0.5 U/ml Isocitric Dehydrogenase (ICD). The assay plate was incubated at 37° C. (expect; for 1A2 and 3A4 at 30° C.) and taking fluoresce reading every minutes over 20 to 30 min.

Data calculations were preceded as follows;
1. The slope (Time vs. Fluorescence units) was calculated at the linear region
2. The percentage of inhibition in compounds was calculated by the equation $$\{(v_o-v_i)/v_o\}\times100=\% \text{ inhibition}$$

Wherein
$v_o$=rate of control reaction (no inhibitor)
$v_i$=rate of reaction in the presence of compounds.

TABLE 1

| Condition for drug—drug interaction assay. | | | | | |
|---|---|---|---|---|---|
| | 1A2 | 2C9 | 2C19 | 2D6 | 3A4 |
| Substrate | Vivid blue (Aurora) | MFC (Gentest) | Vivid blue (Aurora) | AMMC (Gentest) | Vivid red (Aurora) |
| Substrate (µM) | 10 | 30 | 10 | 1 | 2 |
| Enzyme (pmol) | 50 | 50 | 5 | 50 | 5 |
| EX./Em(λ) | 408/465 | 408/535 | 408/465 | 400/465 | 530/595 |

Half-life in Human Liver Microsomes (HLM)

Test compounds (1 µM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

Half-life=$\ln 2/k$

Drug Substance

Pharmaceutically acceptable salts of the compounds of formula (I) include the acid addition and base salts thereof.

Suitable acid addition salts are formed from acids which form non-toxic salts. Examples include acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

Included within the scope of the invention are complexes such as clathrates, drug-host inclusion complexes wherein, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269–1288 by Haleblian (August 1975).

Hereinafter all references to compounds of formula (I) include references to salts and complexes thereof.

The compounds of the invention include compounds of formula (I) as hereinbefore defined, polymorphs, prodrugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:

(i) where the compound of formula (I) contains an alcohol functionality (—OH), an ether thereof, for example, replacement of the hydrogen with $(C_1-C_6)$alkanoyloxymethyl; and (ii) where the compound of formula (I) contains a primary or secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparationtisolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethytamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

VR1 antagonists may be usefully combined with another pharmacologically active compound, or with two or more other pharmacologically active compounds, particularly in the treatment of pain. For example, VR1 antagonists, particularly a compound of formula (I), or a pharmaceutically acceptable salt or solvate thereof, as defined above, may be administered simultaneously, sequentially or separately in combination with one or more agents selected from:

(I) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(II) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(III) a barbiturate sedative, e.g. amobarbital, aprobarbital, butabarbital, butabital, mephobarbital, metharbital, methohexital, pentobarbital, phenobartital, secobarbital, talbutal, theamylal or thiopental;

(IV) a benzodiazepine having a sedative action, e.g. chlordiazepoxide, clorazepate, diazepam, flurazepam, lorazepam, oxazepam, temazepam or triazolam;

(V) an $H_1$ antagonist having a sedative action, e.g. diphenhydramine, pyrilamine, promethazine, chlorpheniramine or chlorcyclizine;

(VI) a sedative such as glutethimide, meprobamate, methaqualone or dichloralphenazone;

(VII) a skeletal muscle relaxant, e.g. baclofen, carisoprodol, chlorzoxazone, cyclobenzaprine, methocarbamol or orphrenadine;

(VIII) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(IX) an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,
3,4-tetrahydroisoquinol-2-yl)-5-(2-pyridyl)quinazoline;
(X) a tricyclic antidepressant, e.g. desipramine, imipramine, amitriptyline or nortriptyline;
(XI) an anticonvulsant, e.g. carbamazepine, lamotrigine, topiratmate or valproate;
(XII) a tachykinin (NK) antagonist, particularly an NK-3, NK-2 or NK-1 antagonist, e.g. (αR,9R)-7-[3,5-(trifluoromethyl)benzyl]-8,9,10,11-tetrahydro-9-methyl-5-(4-methylphenyl)-7H-[1,4]diazocino[2,1-g][1,7]-naphthyridine-6–13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
(XIII) a muscarinic antagonist, e.g oxybutynin, tolterodine, propiverine, tropsium chloride, darifenacin, solifenacin, temiverine and ipratropium;
(XIV) a COX-2 selective inhibitor, e.g. celecoxib, rofecoxib, parecoxib, valdecoxib, deracoxib, etoricoxib, or lumiracoxib;
(XV) a coal-tar analgesic, in particular paracetamol;
(XVI) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;
(XVII) a vanilloid receptor agonist (e.g. resinferatoxin) or antagonist (e.g. capsazepine);
(XVIII) a beta-adrenergic such as propranolol;
(XIX) a local anaesthetic such as mexiletine;
(XX) a corticosteroid such as dexamethasone;
(XXI) a 5-HT receptor agonist or antagonist, particularly a 5-HT$_{1B/1D}$ agonist such as eletriptan, sumatriptan, naratriptan, zolmitriptan or rizatriptan;
(XXII) a 5-HT$_{2A}$ receptor antagonist such as R(+)-alpha-(2,3-dimethoxy-phenyl)-1-[2-(4-fluorophenylethyl)]-4-piperidinemethanol (MDL-100907);
(XXIII) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
(XXIV) Tramadol®;
(XXV) a PDEV inhibitor, such as 5-[2-ethoxy-5-(4-methyl-1-piperazinyl-sulphonyl)phenyl]-1-methyl-3-N-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidiny)-2,6dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-, one 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl) -N{2-(1-methylpyrrolidin-2-yl)ethyl]-4-propoxybenzenesulfonamide;
(XXVI) an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R, 6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1tetrazol-5-ylmethyl)-cycloheptyl]-methylamine, (3S,4S)-(1-aminomethyl-5-methyl-octanoic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;
(XXVII) a cannabinoid;
(XXVIII) metabotropic glutamate subtype 1 receptor (mGluR1) antagonist;
(XXIX) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;
(XXX) a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;
(XXXI) a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;
(XXXII) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3pyridinecarbonitrile, 2-[[(1R,3S)-3-amino-4-hydroxy-1-(5-thiazolyl)butyl]thio]-5-chlorobenzonitrile, -N-[4-[2-(chlorobenzylamino)ethyl]phenyl]thiophene-2-carboxamidine, or guanidinoethyldisulfide;
(XXXIII) an acetylcholinesterase inhibitor such as donepezil;
(XXXIV) a leukotriene B4 antagonist; such as 1-(3-biphenyl-4-ylmethyl-4-hydroxy-chroman-7-yl)-cyclopentanecarboxylic acid (CP-105696), 5-[2-(2–Carboxyethyl)-3-[6-(4-methoxyphenyl)-5E-hexenyl]oxyphenoxy]-valeric acid (ONO-4057) or DPC-11870,
(XXXV) a 5-lipoxygenase inhibitor, such as zileuton, 6-[(3-fluoro-5-[4-methoxy-3,4,5,6-tetrahydro-2H-pyran-4-yl])

phenoxy-methyl]-1-methyl-2-quinolone (ZD-2138), or 2,3,5-trimethyl-6-(3-pyridylmethyl),1,4-benzoquinone (CV-6504);

(XXXVI) a sodium channel blocker, such as lidocaine;
(XXXVII) a 5-HT3 antagonist, such as ondansetron;

and the pharmaceutically acceptable salts and solvates thereof.

Thus, the invention further provides a combination comprising a compound of the invention or a pharmaceutically acceptable salt or pro-drug thereof, and a compound or class of compounds selected from the group (I)–(XXXVII) above. There is also provided a pharmaceutical composition composition comprising such a combination, together with a pharmaceutically acceptable excipient, diluent or carrier, particularly for the treatment of a disease for which a VR1 antagonist is implicated.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981–986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannftol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryi sulphate. Lubricants generally comprise from 0.25 wt % to 10 wt %, preferably from 0.5 wt % to 3 wt % of the tablet.

Other possible ingredients include anti-oxidants, colorants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified controlled release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1–14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably. to a pH of from 3 to 9), but, for some applications, they may be more suitably formulated as a sterile non-aqueous solution or as powdered a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for use with needle-free injection administration comprise a compound of the invention in powdered form in conjunction with a suitable vehicle such as sterile, pyrogen-free water.

Formulations for parenteral administration may be formulated to be immediate and/or modified controlled release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose tio include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955–958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified controlled release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as Ileucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified controlled release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 10 mg of the compound of formula (I). The overall daily dose will typically be in the range 1 µg to 10 mExg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified controlled release. Modified release formulations include delayed-, sustained-, pulsed-, controlled-, targeted and programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-Of-Parts

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range 0.1 mg to 3000 mg, preferably from 1 mg to 500 mg, depending, of course, on the mode of administration. For example, oral administration may require a total daily dose of from 0.1 mg to 3000 mg, preferably from 1 mg to 500 mg, while an intravenous dose may only require from 0.1 mg to 1000 mg, preferably from 0.1 mg to 300 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

The compounds prepared in the following examples showed the excellent hVR1 antagonist activity determined by the method described as capsaicin stimulation assay in the section of "Method of assessing biological activities" of the present specification. Also the compounds prepared in the following examples showed the superior Half-life in human liver microsomes (HLM), can be detected as $T_{1/2}$ value, according to the method described in the Section of "Half-life in human liver microsomes (HLM)".

EXAMPLES

The invention is illustrated in the following non-limiting examples in which, unless stated otherwise: all operations were carried out at room or ambient temperature, that is, in the range of 18 to 25° C.; evaporation of solvent was carried out using a rotary evaporator under reduced pressure with a bath temperature of up to 60° C.; reactions were monitored by thin layer chromatography (TLC) and reaction time is given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates), mass spectrometry, nuclear magnetic resonance spectra (NMR), infrared red absorption spectra (IR) or microanalysis. Yields are given for illustrative purposes only. Flash column chromatography was carried out using Merck silica gel 60 (230–400 mesh ASTM) or Fuji Silysia Chemical L.T.D. amino bounded silica gel (30–50 μm, DU3050) or Biotage amino bounded silica (35–75 μm, KP-NH) or Biotage silica (32–63 μm, KP-Sil). In some cases, product was purified using high pressure liquid chromatography (Apparatus : UV-trigger preparative HPLC system (Waters), Column: XTerra MS C18, 5 um, 19×50 mm or 30×50 mm, Detector: UV 254 nm, Conditions: $CH_3CN/0.05\%$ HCOOH aq. or $CH_3CN/0.01\%$ $NH_3$ aq. 20 mL/min (19×50 mm) or 40 mL/min (30×50 mm) at ambient temp. Microwave reaction was carried out using Emrys Optimizer (Personal Chemistry). Low-resolution mass spectral data (EI) were obtained on a Integrity (Waters) mass spectrometer. Low-resolution mass spectral data (ESI) were obtained on a ZMD (Micromass) mass spectrometer. NMR data was determined at 270 MHz (JEOL JNM-LA 270 spectrometer) or 300 MHz (JEOL JNM-LA300 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; bp (boiling point), mp (melting point), L (liter(s)), mL (milliliter(s)), g (gram(s)), mg (milligram(s)), mol (moles), mmol (millimoles), eq. (equivalent(s)), quant. (quantitative yield).

In the structure in the present specification, "Me" represents a methyl group; "Ms" represents a methylsulphonyl group; "Boc" represents a tert-butyloxycarbonyl group; and "Tf" represents a trifluoromethylsulfonyl group.

Example 1

2-(4-tert-Butylphenoxy)-N{3-fluoro-4-[(methylsulfonyl)amino]benzyl}acetamide

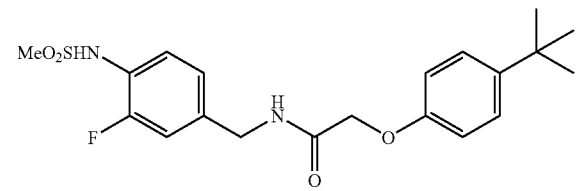

To a N,N-dimethylformamide (DMF) (10 ml) solution of (4-tert-butylphenoxy)acetic acid (50 mg, 0.2 mmol) and N-[4-(aminomethyl)-2-fluorophenyl]methanesulfonamide hydrochloride (40.4 mg, 0.2 mmol, J. Med. Chem. 2003, 46, 3116–3126), 1-ethyl-3-(3'-dimethylaminopropyl)carbodiimide hydrochloride (EDC) (112 mg, 0.6 mmol), 1-hydroxybenzotriazole(HOBt) monohydrate (catalytic amount 5 mg) and triethylamine (0.3 ml) were added and the mixture was stirred for 3 hours at ambient temperature. The reaction mixture was then quenched with saturated aqueous solution of sodium bicarbonate and then crude products were extracted with methylene dichloride. The organic layer was then washed with brine and dried over sodium sulfate. After filtration to separate solvent and sodium sulfate, the solvent was removed under reduced pressure to give a residue, which was applied to a silica gel chromatography column and eluted with methylene dichloride/methanol=9/1 to furnish 0.59 g (75% yield) of the title compound as a white solid.

$^1$H NMR (270 MHz CDCl$_3$) δ ppm 1.30 (9H, s), 1.62 (2H, s), 3.02 (3H, s), 4.51–4.56 (m, 2H), 6.58 (1H, brs), 6.82–6.88 (2H, m), 7.04–7.09 (2H, m), 7.21–7.36 (2H, m), 7.52 (1 H, t, J=8.5 Hz).

MS (ESI) m/z: 409 (M+H)$^+$.

Example 2

N-3-Fluoro-4-[(methylsulfonyl)amino]benzyl-2-[4-(2,2,2-trifluoro-1,1-dimethylethyl)phenoxy]acetamide 2(a): [4-(2,2,2-Trifluoro-1,1-dimethylethyl)phenoxy] acetic acid

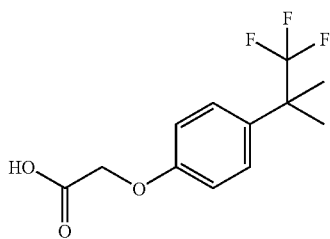

To a mixture of 4-(2,2,2-trifluoro-1,1-dimethylethyl)phenol (408 mg, 2.0 mmol, WO 9708144A1) and potassium carbonate (552 mg, 4.0 mmol) in N,N-dimethylformamide (DMF) (30 ml) was added ethyl bromoacetate (334 mg, 2.0 mmol) and the mixture was stirred for 3 hours at ambient temperature. The reaction was partitioned with water and a 1:10 by volume mixture of ethylacetate/hexane, and the organic layer was separated and dried over sodium sulfate. After filtration to separate solvent and sodium sulfate, the solvent was removed under reduced pressure to give a residue, which was passed through a silica gel chromatography column and eluted with a 1:1 by volume mixture of ethyl acetate/hexane to furnish ethyl [4-(2,2,2-trifluoro-1,1-dimethylethyl)phenoxy]acetate. Then, ethyl [4-(2,2,2-trifluoro-1,1-dimethylethyl)phenoxy]acetate was treated with 2M aqueous sodium hydroxide (3.0 ml) and methanol (3.0 ml) for 2 hours at room temperature and was quenched with 2M aqueous hydrogen chloride to acidify the mixture adjusting to pH 1. Crude product was extracted with ethyl acetate, and then the organic layer was dried over magnesium sulfate. After filtration, solvent was evaporated under reduced pressure to give 345 mg (66% yield) of the title compound as a white solid.

$^1$H NMR (270 MHz CDCl$_3$) δ ppm 1.31 (9H, s), 4.58 (2H, s), 4.85 (2H, d, J=4.4 Hz), 6.94 (2H, d, J=8.6 Hz), 7.36 (2H, d, J=8.6 Hz), 7.47–7.56 (2H, m), 7.60–7.70 (1H, m), 7.69 (1H, NH), 7.90–8.10 (2H, m).

MS (ESI) m/z: 326 [M+H]$^+$.

2(b): N-{3-fluoro-4-[(methylsulfonyl)amino]benzyl}-2-[4-(2,2,2-trifluoro-1,1-dimethylethy)phenoxy]acetamide

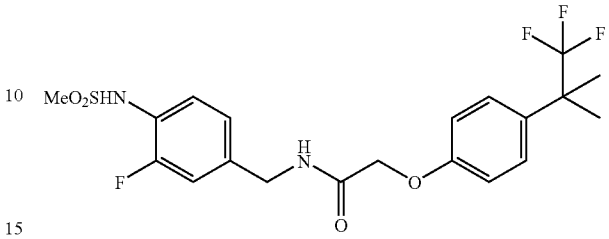

To a tetrahydrofuran (THF) (3.0 ml) solution of [4-(2,2,2-trifluoro-1,1-dimethylethyl)phenoxy]acetic acid (157 mg, 0.6 mmol) was added 2-chloro-1,3-dimethylimidazolinium chloride (CDI) (97 mg, 0.6 mmol) at room temperature and the mixture was stirred for 2 hours, followed by additional stirring for 10 hours with triethylamine (0.33 ml) and N-[4-(aminomethyl)-2-fluorophenyl]methanesulfonamide hydrochloride (122 mg, 0.48 mmol). The reaction was partitioned with water and methylene dichloride and the organic layer was separated, dried over sodium sulfate. After filtration to separate solvent and sodium sulfate, the solvent was removed under reduced pressure to give a residue, which was applied to a silica gel chromatography column and eluted with a volume mixture of methylene dichloride and methanol (5/1 to 5/2) to furnish 62.9 mg (28% yield) of the title compound as colorless oil.

$^1$H NMR (300 MHz, CDCl$_3$)δ ppm 1.56 (6H, s), 3.01 (3H, s), 4.52 (2H, d, J=6.91 (2H, d, J=9.1 Hz), 7.05–7.11 (3H, m), 7.45 (1 H, d, J=8.6 Hz), 7.52 (1H, t, J=8.4 Hz), 7.69 (2H, brs).

MS (ESI) m/z: 463 [M+H]$^+$.

Example 3

2-(4-tert-Butyl-3-methoxyphenoxy)-N-{3-fluoro-4-[(methylsulfonyl)amino]benzyl}acetamide 3(a): 4-tert-butyl-3-methoxyphenol

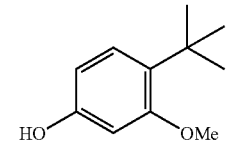

To a suspension of zirconium tetrachloride (2.3 g, 10 mmol) in methylene dichloride (30 ml) was added methyl tert-butyl ether (0.88 g, 10 mmol) at 0° C. After stirring at 0° C. for 30 minutes, 3-methoxyphenol (1.24 g, 10 mmol) in methylene dichloride was added and the mixture was stirred for 2 hours at ambient temperature. The reaction was quenched with saturated aqueous sodium bicarbonate, followed by the addition of methylene dichloride. Then, the organic layer was separated, dried over magnesium sulfate, filtered off, evaporated under reduced pressure to give a residue, which was applied to a silica gel chromatography column eluted with a volume mixture of hexane and ethylacetate (20/1 to 4/1) to furnish 360 mg (20% yield) of the title compound as a white solid.

$^1$H NMR (300 MHz, CDCl$_3$) δ ppm 1.33 (9H, s), 3.80 (3H, s), 4.79 (1 H, s), 6.33 (1H, dd, J=2.6, 8.5 Hz), 6.43 (1H, d, J=2.7 Hz), 7.09 (1H, d, J=8.4 Hz).

3(b): tert-Butyl (4-tert-butyl-3-methoxyphenoxy)acetate

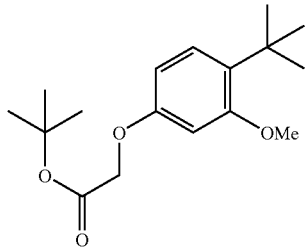

To a suspension of 60% sodium hydride (96 mg, 2.4 mmol) in tetrahydrofuran (THF) (10 ml) was added 4-tert-butyl-3-methoxyphenol (360 mg, 2 mmol) at 0° C., followed by additional stirring for 30 minutes. Then, tert-butyl bromoacetate (468 mg, 2.4 mmol) was added and the mixture was refluxed at 80° C. for 1 hour. The reaction was then quenched with saturated aqueous solution of ammonium chloride and the crude product was extracted with ethylacetate. The organic layer was separated, washed with brine, dried over magnesium sulfate. Then, filtration, evaporation to remove the solvent under reduced pressure gave the residue, which was applied to a silica gel chromatography column and eluted with a volume mixture of hexane and ethylacetate (20/1 to 4/1) to furnish 466 mg (79% yield) of the title compound as a white solid.

$^1$H NMR (CDCl$_3$, 300 MHz) δ ppm 1.33 (9H, s), 1.50 (9H, s), 3.80 (3H, s), 4.48 (2H, s), 6.32 (1H, dd, J =2.6, 8.6 Hz), 6.54 (1H, d, J=2.6 Hz), 7.14 (1H, d, J=8.6 Hz).

MS (ESI) m/z: 295 [M+H]$^+$.

3(c): 2-(4-tert-Butyl-3-methoxyphenoxy)-N-{3-fluoro-4-[(methylsulfonyl)amino]benzyl}acetamide

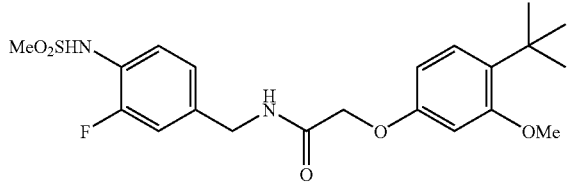

A mixture of tert butyl (4-tert-butyl-3-methoxyphenoxy) acetate (466 mg, 1.6 mmol), trifluoroacetic acid (2.0 ml), tetrahydrofuran (THF) (3.0 ml) and methylene dichloride (2.0 ml) was stirred for 1 hour at ambient temperature. After being concentrated under reduced pressure, the residue was used for further reaction without purification (460 mg). Then (4-tert-butyl-3-methoxyphenoxy)acetic acid (460 mg, crude), 2-chloro-1,3-dimethylimidazolinium chloride (CDI) (97 mg, 0.6 mmol), triethylamine (0.33 ml) and N-[4-(aminomethyl)-2-fluorophenyl]methanesulfonamide hydrochloride (160 mg, 0.63 mmol) were treated in the same procedure described in Example 2(b) to give 8.1 mg (1.1% yield) of the title compound as a white solid.

$^1$H NMR (CDCl$_3$, 270 MHz) δ ppm 1.34 (9H, s), 3.02 (3H, s), 3.81 (3H, s), 4.52 (2H, d, J=6.2 Hz), 4.56 (2H, s), 6.42–6.54 (2H, m), 6.72 (1H, s), 6.97 (1H, brt), 7.03–7.13 (2H, m), 7.19 (1H, d, J=8.5 Hz), 7.53 (1H, t, J=8.0 Hz).

MS (ESI) m/z: 439 [M+H]$^+$.

Example 4

2-(4-tert-Butyl-3-fluorophenoxy)-N-{3-fluoro-4-[(methylsulfonyl)amino]benzyl}acetamide 4(a): 4-tert-Butyl-3-fluorophenol

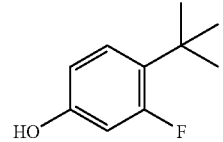

To a suspension of zirconium tetrachloride (1.2 g, 5 mmol) in methylene dichloride (15 ml), methyl tert-butyl ether (0.44 g, 5 mmol), 3-fluorophenol (0.56 g, 5 mmol) were treated in the same procedure described in Example 3(a) to furnish 458 mg (55% yield) of the title compound as a white solid.

$^1$H NMR (CDCl$_3$, 270 MHz) δ ppm 1.34 (9H, s), 4.97 (1H, brs), 6.56–6.50 (2H, m), 7.13 (1H, t,J=8.7 Hz).

4(b): tert-Butyl (4-tert-butyl-3-fluorophenoxy)acetate

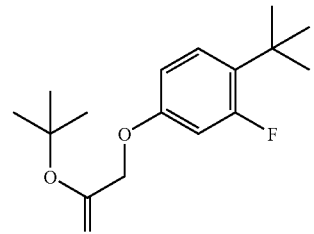

Sixty % sodium hydride (128 mg, 3.2 mmol), 4-tert-butyl-3-fluorophenol (450 mg, 2.7 mmol), tert-butyl bromoacetate (632 mg, 3.2 mmol) were treated in the same procedure described in Example 3(b) to furnish 634 mg (82% yield) of the title compound as a white solid.

$^1$H NMR (300 MHz, CDCl$_3$) δ ppm 1.34 (9H, s), 1.49 (9H, s), 4.47 (2H, s), 6.50–6.65 (2H, m), 7.18 (1H, t, J=9.1 Hz).

MS (ESI) m/z: 281 [M−H]$^-$.

4(c): (4-tert-Butyl-3-fluorophenoxy)aceticacid

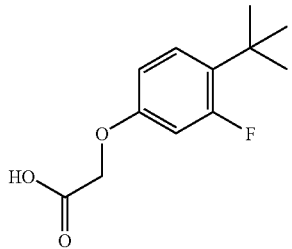

A mixture of tert-butyl (4-tert-butyl-3-fluorophenoxy)acetate (630 mg, 2.2 mmol), trifluoroacetic acid (3.0 ml), tetrahydrofuran (3.0 ml) and methylene dichloride (3.0 ml) was treated in the same procedure described in Example 3(c) to furnish 443 mg of the title compound which was used for further reaction without purification.

4(d): 2-(4-tert-Butyl-3-fluorophenoxy)-N-(3-fluoro-4-[(methylsulfonyl)amino]benzyl}acetamide

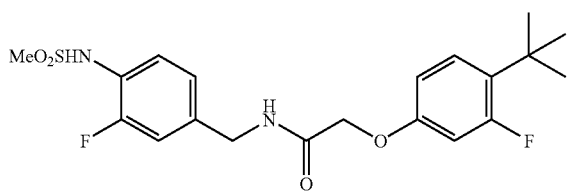

Crude (4-tert-butyl-3-fluorophenoxy)acetic acid (124 mg, crude), 2-chloro-1,3-dimethylimidazolinium chloride (CDI) (90 mg, 0.55 mmol), triethylamine (0.35 ml) and-N[4-(aminomethyl)-2-fluorophenyl]methanesulfonamide hydrochloride (127 mg, 0.5 mmol) were mixed in the same procedure described in Example 2(b) to give 18 mg (7.8% yield) of the title compound as a white solid.

$^1$H NMR (300 MHz, CDCl$_3$) δ ppm 1.35 (9H, s), 3.02 (3H, s), 4.52 (2H, d, J=7.1 Hz), 4.53 (2H, s), 6.53 (1H, brs), 6.56–6.67 (2H, m), 6.92 (1H, brs), 7.03–7.12 (2H, m), 7.23 (1H, t, J=8.8 Hz), 7.53 (1H, t, J=8.2 Hz).

MS (ESI) m/z: 427 [M−H]$^-$.

Example 5

2-[3–Chloro-4-(trifluoromethyl)phenoxyl]-N-{3-methyl-4-[(methylsulfonyl)amino]benzyl}acetamide

5(a): 3–Chloro-4-(trifluoromethyl)phenol

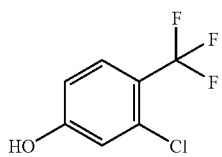

To a sulfuric acid (14 ml) —H$_2$O (14 ml) solution of 3-chloro-4-(trifluoromethyl)aniline (1.96 g, 10 mmol) was added a H$_2$O (10 mL) solution of sodium nitrite (828 mg,12 mmol) at 0 °C. The reaction mixture was stirred at ambient temperature for 1 hour. The mixture was poured into 10 M sulfuric acid (50 mL). The stirred mixture was refluxed at 110 °C. for 2 hours. The reaction mixture was then quenched with saturated aqueous solution of sodium bicarbonate and then crude products were extracted with ethyl acetate The organic layer was then washed with brine, dried over sodium sulfate. After the filtration to separate solvent and sodium sulfate, the solvent was removed under reduced pressure to give the residue, which was applied to a silica gel chromatography column and eluted with a ethyl acetate/hexane=⅓ to furnish 945 mg (48% yield) of the title compound as a brown oil.

$^1$H NMR (CDCl$_3$, 270 MHz) δ ppm 5.99 (1H, brs), 6.80 (1H, dd, J=2.6, 8.6 Hz), 7.00 (1H, d, J=2.6 Hz), 7.56 (1H, d, J=8.6 Hz).

MS (ESI) m/z: 195[M−H]$^-$.

5 (b): tert-Butyl [3-chloro-4-(trifluoromethyl)phenoxylacetate

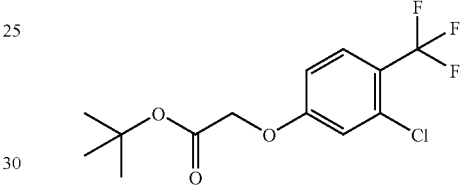

3-chloro-4-(trifluoromethyl)phenol (940 mg, 4.8 mmol), potassium carbonate (2.0 g, 14.0 mmol) and tert-butyl bromoacetate (1.0 mL, 6.4 mmol) were stirred under reflux condition for 14 hours. The precipitate was filtered off and washed with acetone. The filtrate was concentrated under reduced pressure to give the residue, which was applied to a silica gel chromatography column and eluted with a volume mixture of hexane and ethyl acetate (19/1 to 4/1) to furnish 1.2 g (80% yield) of the title compound as a brown oil.

$^1$H NMR (CDCl$_3$, 300 MHz) δ ppm 1.50 (9H, s), 4.56 (2H, s), 6.84 (1H, dd, J=2.6, 8.6 Hz), 7.03 (1H, d, J =2.6 Hz), 7.61 (1H, d, J=8.6 Hz).

5 (c): [3–Chloro-4-(trifluoromethyl)phenoxy]acetic acid

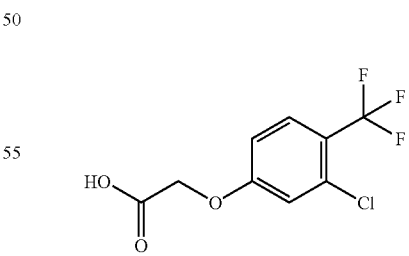

tert-Butyl [3-chloro-4-(trifluoromethyl)phenoxy]acetate (1.2 g, 3.8 mmol) was added trifluoroacetic acid (TFA) (3 ml). The mixture was stirred for 5 hours at ambient temperature. The solvent was removed under reduced pressure to give the residue, which was applied to a recrystallization from hexane-methylene dichloride to furnish 251 mg (80% yield) of the title compound as a brown solid.

¹H NMR (CDCl₃, 270 MHz) δ ppm 4.75 (2H, s), 6.88 (1H, d, J=8.8 Hz), 7.07 (1H, s), 7.64 (1H, d, J=8.8 Hz), 8.58 (1H, brs).

MS (ESI) m/z: 253 [M–H]⁻.

5 (d); 2-[3-Chloro-4-(trifluoromethyl)phenoxy]-N-{3-methyl-4-[(methylsulfonyl)amino]benzyl}acetamide

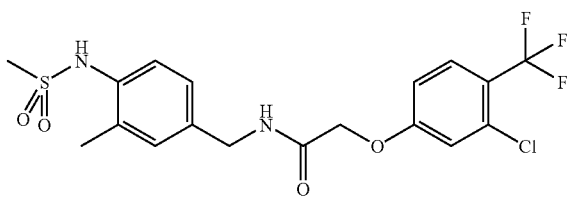

[3-Chloro-4-(trifluoromethyl)phenoxy]acetic acid (127 mg, 0.5 mmol), 2-chloro-1,3-dimethylimidazolinium chloride (CDI) (97 mg, 0.6 mmol), triethylamine (0.33 ml) and N{4-(aminomethyl)-2-methylphenyl]methanesulfonamide hydrochloride (151 mg, 0.6 mmol) were treated in the same procedure described in Example 2(b). The crude residue was applied to a silica gel chromatography column and eluted with a volume mixture of hexane and ethyl acetate (3/1 to 1/1) to furnish 150 mg (67% yield) of the title compound as a white solid.

¹H NMR (CDCl₃, 270 MHz) δ ppm 2.31 (3H, s), 3.03 (3H, s), 4.50 (2H, d, J=5.9 Hz), 4.59 (2H, s), 6.25 (1H, brs), 6.77 (1H, brs), 6.89 (1H, dd, J=2.0, 8.6 Hz), 7.09 (1H, d, J=2.0 Hz), 7.16 (2H, brs), 7.43 (d, J=8.5 Hz), 7.65 (1H, J=8.6 Hz).

MS (ESI) m/z: 451 [M+H]⁺.

Example 6

2-(4-tert-Butyl-2-chlorophenoxy)-N-{3-fluoro-4-[(methylsulfonyl)amino]benzyl}acetamide

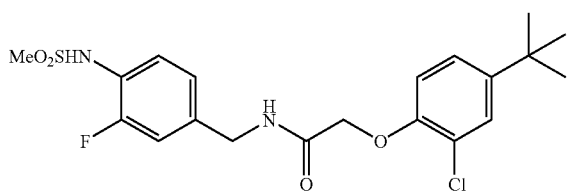

A mixture of (4-tert-butyl-2-chlorophenoxy)acetic acid (121 mg, 0.5 mmol), 2-chloro-1,3-dimethylimidazolinium chloride (CDI) (90 mg, 0.55 mmol), triethylamine (0.30 ml), tetrahydrofuran (3.0 ml) and N-[4-(aminomethyl)-2-fluorophenyl]methanesulfonamide hydrochloride (127 mg, 0.5 mmol) was treated in the same procedure described in Example 2(b) to give 16 mg (7% yield) of the title compound as a white solid.

¹H NMR (300 MHz, CDCl₃) δ ppm 1.30 (9H, s), 3.02 (3H, s), 4.55 (2H, d, J=6.3 Hz), 4.60 (2H, s), 6.53 (1H, brs), 6.87 (1H, d, J=8.6 Hz), 7.05–7.17 (2H, m), 7.21–7.31 (2H, m), 7.41 (1H, d, J=2.5 Hz), 7.55 (1H,t,J=8.1 Hz).

MS (ESI) m/z: 443 [M+H]⁺.

Example 7

2-(4-tert-Butylphenoxy)-2,2-difluoro-N-{3-fluoro-4-(methylsulfonyl)amino]benzyl}acetamide

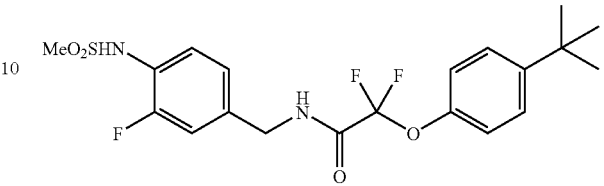

To a methylene dichloride (10 ml) solution of (4-tert-butylphenoxy)difluoroacetic acid (100 mg, 0.4 mmol, Ambinter Screening Library) and oxalyl chloride (0.1 ml) was added 4-(dimethylamino)pyridine (DMAP) (5 mg) and the mixture was stirred for 1 hour at ambient temperature. After evaporation under reduced pressure, crude residue was used for further reaction without purification. To this crude residue, triethylamine (0.5 ml), methylene dichloride (5.0 ml) and N{4-(aminomethyl)-2-fluorophenyl]-methanesulfonamide hydrochloride were added (125 mg, 0.4 mmol) and the reaction mixture was stirred for 3 hours at ambient temperature. After quenching with saturated aqueous sodium bicarbonate, crude products were extracted with methylene dichloride and the organic layer was washed with brine, dried over sodium sulfate. Then, filtration to remove sodium sulfate, evaporation under reduced pressure gave the residue, which was applied to a silica gel chromatography column and eluted with a volume mixture of methylene chloride and methanol (1/9) to furnish 26.8 mg (15% yield) of the title compound as a white solid.

¹H NMR (300 MHz, CDCl₃) δ ppm 1.31 (9H, s), 3.03 (3H, s), 4.51 (2H, d, J=6.1 Hz), 7.08–7.15 (m, 5H), 7.38 (2H, d, J=8.8 Hz), 7.53 (1H, t, J=8.1 Hz).

MS (ESI) m/z: 445 [M+H]⁺.

Example 8

2-[(5,5-Dimethyl-5,6,7,8-tetrahydronaphthalen-2-yl)oxy]-N-{3-fluoro-4-[(methylsulfonyl)amino]benzyl}acetamide 8(a): 5,5-Dimethyl-5,6,7,8-tetrahydronaphthalen-2-ol

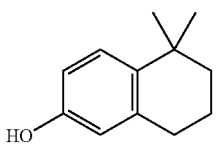

To a methylene chloride (10 ml) solution of 6-methoxy-1,1-dimethyl-1,2,3,4-tetrahydronaphthalene (Tetrahedron, 1994, 50, 3297) (2.28 g, 12.0 mmol) was added methylene chloride solution of boron tribromide (1M, 24 mL, 24.0 mmol) at 0° C. The mixture was stirred at 0° C. for 2 hours. The reaction mixture was then quenched with methanol and then the solvent was removed under reduced pressure to give a residue, which was applied to a silica gel chromatography column and eluted with ethyl acetate/hexane=1/3 to furnish 2.0 g (96% yield) of the title compound as a white solid.

$^1$H NMR (CDCl$_3$, 300 MHz) δ ppm 1.25 (6H, s), 1.59–1.67 (2H, m), 1.71–1.85 (2H, m), 2.70 (2H, t, J=6.2 Hz), 4.65 (1H, s), 6.51 (1H, d, J=2.7 Hz), 6.64 (1H, dd, J=2.7, 8.4 Hz), 7.19 (1H, d, J=8.4 Hz).

MS (ESI) m/z: 175 [M−H]$^-$.

8(b): tert-Butyl [(5,5-dimethyl-5,6,7,8-tetrahydronaphthalen-2-yl)oxy]acetate

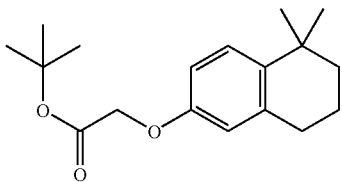

A mixture of 5,5-dimethyl-5,6,7,8-tetrahydronaphthalen-2-ol (2.0 g, 11.3 mmol), 60% sodium hydride (542 mg, 13.2 mmol), tert-butyl bromoacetate (3.3 g, 17 mmol) and tetrahydrofuran (THF) (10 ml) was treated in the same procedure described in Example 3(a) to furnish 2.8 g of the title compound as a white solid.

$^1$H NMR (300 MHz, CDCl$_3$) δ ppm 1.24 (6H, s), 1.49 (9H, s), 1.59–1.67 (2H, m), 1.86–1.72 (2H,m), 2.71 (2H, t, J=6.2 Hz), 4.46 (2H, s), 6.55 (1H, d, J=2.7 Hz), 6.71 (1H, dd, J=8.6, 2.9 Hz), 7.23 (1H, dt, J=8.8 Hz).

MS (ESI) m/z: 291 [M+H]$^+$.

8(c): [(5,5-Dimethyl-5,6,7,8-tetrahydronaphthalen-2-yl)oxy]acetic acid

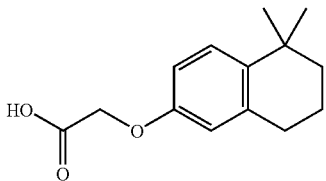

A mixture of tert-butyl [(5,5-dimethyl-5,6,7,8-tetrahydronaphthalen-2-yl)oxy]acetate (2.8 g, 9.6 mmol), trifluoroacetic acid (10.0 ml) and methylene dichloride (20 ml) was stirred for 2 hours at 0° C. After being concentrated under reduced pressure, the crude residue was triturated using hexane and collected by filtration to give 1.45 g of the title compound as a white solid, which was used for further reaction without purification.

$^1$H NMR (300 MHz, CDCl$_3$) δ ppm 1.25 (6H, s), 1.59–1.70 (2H, m), 1.87–1.71 (2H, m), 2.74 (2H, t, J=6.1 Hz), 4.63 (2H, s), 6.60 (1H, d, J=2.7 Hz), 6.74 (1H, dd, J=3.0, 8.7 Hz), 7.25 (1H, d, J=8.6 Hz).

MS (ESI) m/z: 281 [M+H]$^-$,

8(d): 2-[(5,5-Dimethyl-5,6,7,8-tetrahydronaphthalen-2-yl)oxyl-N-{-4-fluoro-4-[(methylsulfonyl)amino]benzyl}acetamide

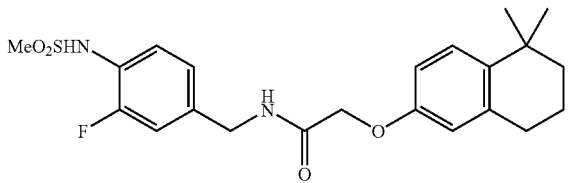

A mixture of [(5,5-dimethyl-5,6,7,8-tetrahydronaphthalen-2-yl)oxy]acetic acid (140 mg, 0.5 mmol), 2-choro-1,3-dimethylimidazolinium chloride (CDI) (97 mg, 0.6 mmol), triethylamine (0.35 ml), tetrahydrofuran (THF) (3.0 ml) and N-{4-(aminomethyl)-2-fluorophenyl]methanesulfonamide hydrochloride (127 mg, 0.5 mmol) was mixed in the same procedure described in Example 2(b) to give 83.6 mg (32% yield) of the title compound as a white solid.

$^1$H NMR (300 MHz, CDCl$_3$) δ ppm 1.25 (6H, s), 1.61–1.70 (2H, m), 1.90 (2H, m), 2.73 (2H, t, J=6.3 Hz), 3.02 (3H, s), 4.51 (2H, d, J=6.4 Hz), 4.53 (2H, s), 6.45–6.65 (2H, m), 6.73 (1H, dd, J=2.6, 8.7 Hz), 6.97 (1H, brs), 7.02–7.13 (2H, m), 7.27 (1H, m), 7.52 (1H, t, J=8.0 Hz).

MS (ESI) m/z: 433 [M−H]$^-$.

Example 9

2-(4-tert-Butylphenoxy)-N-{4-[(methylsulfonyl)amino]benzyl}acetamide

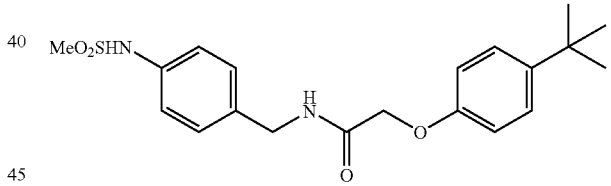

To a stirred pyridine (15 ml) suspension of N-[4-(aminomethyl)-phenyl]methane sulfonamide hydrochloride (376 mg, 1.59 mmol) was added (4-tert-butylphenoxy)acetic acid chloride (300 mg, 1.3 mmol) at 0° C. and the mixture was stirred for 1 hour at ambient temperature. The reaction was then partitioned with ethylacetate and 2M aqueous solution of hydrogen chloride and the organic layer was separated, washed with brine, dried over magnesium sulfate. Then, filtration to remove magnesium sulfate, evaporation under reduced pressure gave the residue, which was applied to a silica gel chromatography column and eluted with a volume mixture of hexane/ethylacetate (1/1 to 1/2) to furnish 240 mg (62% yield) of title compound as a white solid.

$^1$H NMR (270 MHz, DMSO-d$_6$) δ ppm 1.26 (9H, s), 2.94 (3H, s), 4.33–4.25 (2H, m), 4.51 (2H, s), 6.93–6.85 (2H, m), 7.23–7.10 (4H, m), 7.35–7.27 (2H, m), 8.57 (1H, brs), 9.65 (1H, brs).

mp: 163.1° C.

MS (m/z): 391 [M+H]$^+$, 389 [M−H]$^-$.

EXAMPLE 10

2-(4-tert-Butylphenoxy)-N-{3-chloro-4-[(methdysulfonyl)amino]benzyl}acetamide

10(a): N-(2-chloro-4-cyanophenyl)methanesulfonamide

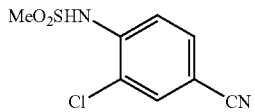

A mixture of N-(2-chloro-4-iodophenyl)methanesulfonamide (4.4 g, 13.3 mmol, *Industrie Chimique Belge* 1974, 39, 490–500), zinc(II)cyanide (1.95 g, 16.6 mmol) and palladium(0) tetrakis(triphenyl phosphine) (1.53 g, 1.33 mmol) in N,N-dimethyl formamide (DMF) (30 ml) was heated at 90° C. for 1.5 hours. Then, the mixture was diluted with ethyl acetate and toluene (8:1) solution (250 ml) and washed with water, brine, dried over sodium sulfate. Then, filtration, evaporation to remove solvent gave the crude residue, which was applied to a silica gel chromatography column and eluted with a volume mixture of methylene dichloride/hexane(2/1 to 4/2) to furnish 2.69 g (88% yield) of title compound as a white solid.

$^1$H NMR (300 MHz, DMSO- $d_6$) δ ppm 3.19 (3H, s), 7.66 (1H, d, J=8.4 Hz), 7.80–7.86 (1H, m), 8.15–8.10 (1H, m), 9.91 (1H, brs).

10(b): N-[4-(Aminomethyl)-2-chlorophenyl]methanesulfonamide hydrochloride

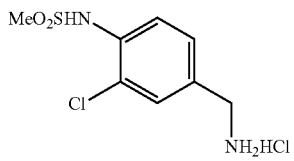

A mixture of N-(2-chloro-4-cyanophenyl)methanesulfonamide (0.5 g, 2.2 mmol) and 10% Pd—C (100 mg) in methanol (7.5 ml)-tetrahydrofuran (7.5 ml)-12M aqueous solution of hydrogen chloride (3.0 ml) was stirred under H$_2$ balloon pressure for 2 hours at ambient temperature. Then, filtration to remove 10% Pd—C, evaporation gave the crude residue, which was applied to recrystallization from methanol and diisopropylether to furnish 500 mg (85% yield) of title compound as a white solid.

$^1$H NMR (270 MHz, DMSO- $d_6$) δ ppm 3.06 (3H, s), 4.01 (2H, s), 7.51–7.47 (2H, m), 7.74 (1H, brs), 8.79 (3H, brs).

10(c): 2-(4-tert-Butylphenoxy)-N-{3-chloro-4 [(methylsulfonyl)amino]-benzyl}acetamide

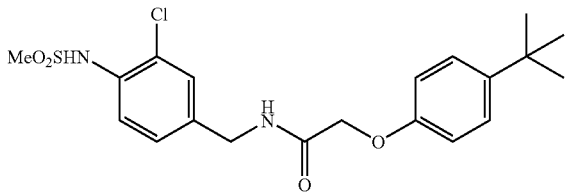

A mixture of N-[-4-(aminomethyl)-2-chlorophenyl]methanesulfonamide hydrogen chloride (488 mg, 1.80 mmol), (4-tert-butylphenoxy)acetic acid (312 mg, 1.5 mmol), 1-ethyl-3-(3'-dimethylaminopropyl)carbodiimide hydrogen chloride (EDC) (518 mg, 2.7 mmol), triethylamine (607 mg, 6.0 mmol) and 4-(dimethylamino)pyridine (DMAP) (55 mg, 0.45 mmol) in N,N-dimethylformamide (DMF) (15 ml) was stirred at ambient temperature for 18 hours. The mixture was diluted with a volume mixture of ethylacetate-toluene (8/1, 100 ml) and organic solvent was washed with 1M aqueous solution of hydrogen chloride and brine, dried over magnesium sulfate. Then, filtration to remove magnesium sulfate, evaporation under removed pressure gave the residue which was applied to an amino bound silica gel chromatography column and eluted with a volume mixture of methylene dichloride: methanol (50/1 to 30/1) to furnish 291 mg (46% yield) of the title compound as a white amorphous solid.

$^1$H NMR (270MHz, CDCl$_3$) δ ppm 1.30 (9H, s), 3.00 (3H, s), 4.51 (2H, d, J=6.3 Hz), 4.55 (2H, s), 6.82–6.90 (2H, m), 6.76 (1H, brs), 6.98 (1H, brs), 7.18–7.24 (1H, m), 7.30–7.40 (3H, m), 7.61 (1H, d, J=8.4 Hz).

MS (m/z): 425 [M+H]$^+$, 423 [M–H]$^-$.

Example 11

2-(4-tert-Butylphenoxy)-N-{3-methoxy-4-[(methysulfonyl)amino]benzyl}acetamide

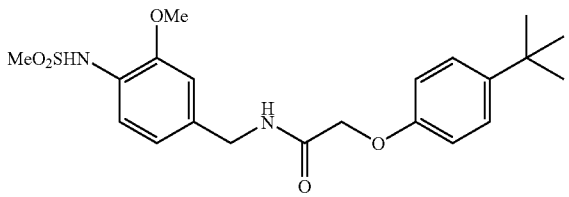

A mixture of N-[4-(aminomethyl)-3-methoxyphenyl]methanesulfonamide trifluoroacetic acid (1.24 g, 3.6 mmol), (4-tert-butylphenoxy)acetic acid (625 mg, 3.0 mmol), 1-ethyl-3-(3'-dimethylaminopropyl) carbodiimide hydrogen chloride (EDC) (1.04 g, 5.4 mmol), triethylamine (1.21 g, 2.0 mmol) and 4-(dimethylamino)pyridine (DMAP) (110 mg, 0.9 mmol) in N,N-dimethylformamide (DMF) (30 ml) was treated in the same procedure described in Example 2(b) to give 543 mg (43% yield) of the title compound as a white amorphous solid.

$^1$H NMR (300 MHz, CDCl$_3$) δ ppm 1.30 (9H, s), 2.94 (3H, s), 3.85 (3H, s), 4.51 (2H, d, J=6.1 Hz), 4.54 (2H, s), 6.77 (1H, brs), 6.82–6.90 (4H, m), 6.95 (1H, brs), 7.30–7.36 (2H, m) 7.47 (1H, d, J=7.9 Hz).

MS (m/z): 421 [M+H]$^+$

Example 12

2-(4-tert-Butylphenoxy)-N-{3-hydroxy-4-[(methyl-sulfonyl)amino]benzyl}acetamide

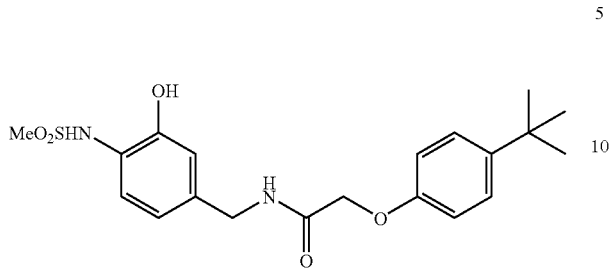

To a solution of 2-(4-tert-butylphenoxy)-N-{3-methoxy-4-[(methylsulfonyl)amino]benzyl}acetamide (Example 11) (446 mg, 1.06 mmol) in methylene dichrolide (20 ml) was added 1.0 M methylene dichloride solution of boron(III) bromide (5.3 ml, 5.3 mmol) at 0° C. After being stirred for 1.5 hours at 0° C., the mixture was quenched with water and crude residue was extracted with methylene dichloride. The organic layer was separated, then washed with brine, dried over magnesium sulfate. Then, filtration to remove magnesium sulfate, evaporation under removed pressure gave the residue, which was applied to a silica gel chromatography column and eluted with a volume mixture of hexane : ethyl acetate (2/3) to furnish 293 mg (55% yield) of the title compound as a white solid.

$^1$H NMR (270 MHz, CDCl$_3$) δ ppm 1.29 (9H, s), 2.96 (3H, s), 4.43–4.49 (2H, m), 4.53 (2H, s), 6.73–6.88 (4H, m), 6.97–7.02 (1H, m), 7.19–7.39 (5H, m), mp: 112.3° C.

MS (m/z): 407 [M+H]$^+$, 405 [M–H]$^-$.

Example 13

2-(4-tert-Butyl-3-chlorophenoxy)-N3-{fluoro-4-[(methylsulfonyl)amino]benzyl}acetamide 13(a): 1-tert-Butyl-2-chloro-4-nitrobenzene

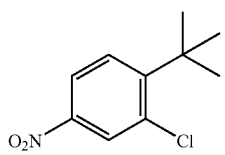

To a conc. chloric acid (10 ml) suspension of 2-tert-butyl-5-nitroaniline (WO 02055501) (1.94 g, 10.0 mmol) was added the H$_2$O (5 ml) solution of sodium nitrite (690 mg, 10.0 mmol) at 0° C. The mixture was stirred at 0° C. for 20 min and to the mixture was then added the conc. chloric acid (10 ml) solution of copper chloride (900 mg, 10.0 mmol) at 70° C. The reaction mixture was stirred at 70° C. for 20 min and the resulting precipitate was collected by filtration, washed with H$_2$O and dried under reduced pressure to furnish furnish 1.76 g (78% yield) of the title compound as a white solid.

$^1$H NMR (CDCl$_3$, 300 MHz) δ ppm 1.52 (9H, s), 7.61 (1H, d, J=8.6 Hz), 8.04 (1H, dd, J=2.6, 9.2 Hz), 8.23 (1H, d, J=2.6 Hz).

13(b): 4-tert-Butyl-3-chloroaniline

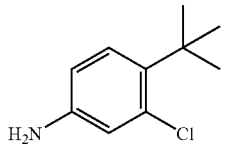

To an acetic acid (7 ml) and conc. chloric acid (2 ml) solution of 1-tert-butyl-2-chloro-4-nitrobenzene (1.67 g, 7.8 mmol) was added zinc powder (4.1 g, 62 mmol) at 60° C. The reaction mixture was stirred at 60° C. for 1 hour. Zinc powder was filtered off and washed with H$_2$O. The filtrate was concentrated in vacuo. The residue was dissolved in ethyl acetate and then the organic layer washed with saturated aqueous solution of sodium bicarbonate and brine, dried over sodium sulfate. After filtration to separate solvent and sodium sulfate, the solvent was removed under reduced pressure to give a residue, which was applied to a silica gel chromatography column and eluted with ethyl acetate/hexane=¼ to furnish 0.7 g (48% yield) of the title compound as a brown oil.

$^1$H NMR (CDCl$_3$, 300 MHz) δ ppm 1.43 (9H, s), 3.59 (2H, brs), 6.51 (1H, dd, J=2.2, 8.1 Hz), 6.71 (1H, d, J=2.2Hz), 7.18 (1H, d, J=8.8 Hz).

MS (ESI) m/z: 184 [M+H]$^+$.

13(c): 4-tert-Butyl-3-chlorophenol

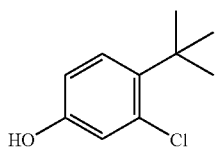

4-tert-Butyl-3-chloroaniline (690 mg, 3.8 mmol) was dissolved in 12 M sulfuric acid (30 ml) and then heated at 90° C. To the clear solution was added 5 ml of aqueous solution of sodium nitrite (776 mg, 11.3 mmol) at ambient temperature. The reaction mixture was stirred at ambient temperature for 15 minutes. Urea was added to the mixture until excess sodium nitrite was destroyed (by checking starch-iodine test paper). A small amount of cupric sulfate was added to the mixture and then the mixture was stirred at 90° C. for 30 minutes. The resulting organic layer was extracted with ethyl acetate washed with brine, dried over sodium sulfate. After filtration to separate solvent and sodium sulfate, the solvent was removed under reduced pressure to give a residue, which was applied to a silica gel chromatography column and eluted with ethyl acetate/hexane=¼ to furnish 0.44 g (64% yield) of the title compound as a brown oil.

$^1$H NMR (CDCl$_3$, 300 MHz) δ ppm 1.44 (9H, s), 5.15 (1H, brs), 6.67 (1H, dd, J=2.6, 8.5 Hz), 6.87 (1H, d, J=3.3 Hz), 7.27 (1H, d, J=8.5 Hz).

MS (ESI) m/z: 183 [M–H]$^-$.

13(d): tert-Butyl (4-tert-butyl-3-chlorophenoxy)acetate

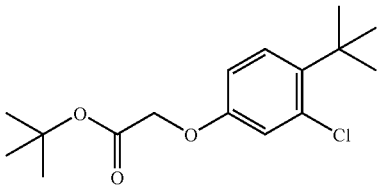

To an acetone (5 ml) solution of 4-tert-butyl-3-chlorophenol (440 mg, 2.4 mmol) were added potassium carbonate (994 mg, 7.2 mmol) and tert-butyl bromoacetate (0.7 ml, 4.8 mmol). The stirred mixture was refluxed at 65° C. for 14 hours. The precipitate was filtered off and washed with acetone. The filtrate was concentrated under reduced pressure to give a residue, which was applied to a silica gel chromatography column and eluted with ethyl acetate/hexane=⅕ to furnish 0.83 g (100% yield) of the title as a colorless oil.

$^1$H NMR (CDCl$_3$, 300 MHz) δ ppm 1.44 (9H, s), 1.49 (9H, s), 4.48 (2H, s), 6.73 (1H, dd, J=2.9, 8.8 Hz), 6.90 (1H, d, J=2.9 Hz), 7.32 (1H, d, J=8.8 Hz).

13(e): (4-tert-Butyl-3-chlorophenoxy)acetic acid

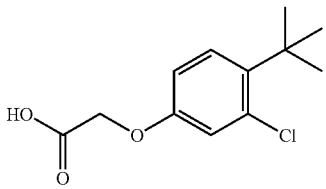

To a methylene chliride (3 ml) solution of tert-butyl (4-tert-butyl-3-chlorophenoxy)acetate (820 mg, 2.4 mmol) was added trifluoroacetic acid (TFA) (3 ml). The mixture was stirred for 5 hours at ambient temperature. The solvent was removed under reduced pressure to give a residue, which was applied to a recrystallization from hexane-methylene dichloride to furnish 657 mg (100% yield) of the title compound as a white solid.

$^1$H NMR (CDCl$_3$, 300 MHz) δ ppm 1.45 (9H, s), 4.67 (2H, s), 6.76 (1H, dd, J=2.6, 8.6 Hz), 6.96 (1H, d, J=2.6 Hz), 7.35 (1H, d, J=8.6 Hz). acetamide

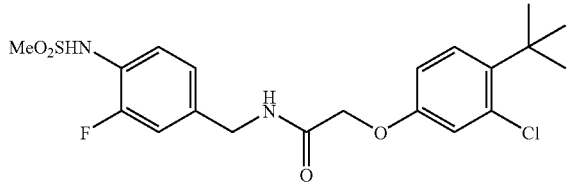

(4-tert-butyl-3-chlorophenoxy)acetic acid (194 mg, 0.8 mmol), 2-chloro-1,3-dimethylimidazolinium chloride (CDI) (168 mg, 1.04 mmol), triethylamine (0.33 ml) and N-[4-(aminomethyl)-2-fluorophenyl]methanesulfonamide hydrochloride (400 mg, 1.6 mmol) were mixed in the same procedure described in Example 2(b) to give 126 mg (36% yield) of the title compound as a white solid.

$^1$H NMR (300 HMz, CDCl$_3$) δ ppm 1.45 (9H, s), 3.02 (3H, s), 4.52 (2H, d, J=7.9 Hz), 4.54 (2H, s), 6.56 (1H, bs), 6.75 (1H, dd, J=2.6, 8.5 Hz), 6.92 (1H, bs), 6.95 (1H, d, J=2.7 Hz), 7.09 (2H, d, J=9.9 Hz), 7.37 (1H, d, J=9.2 Hz), 7.53 (1H, t, J=7.9 Hz).

MS (ESI) m/z: 443 [M+H]$^+$.

Example 14

2-(4-tert-Butyl-3-chlorophenoxy)-N-((1R)-1-{4-[(methylsulfonyl)amino]phenyl}ethyl)acetamide

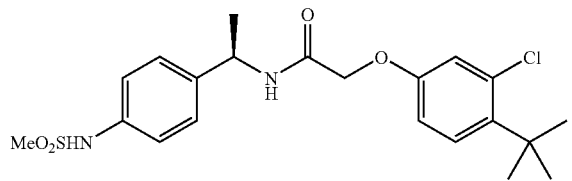

(4-tert-Butyl-3-chlorophenoxy)acetic acid (121 mg, 0.50 mmol), 2-chloro-1,3-dimethylimidazolinium chloride (CDI) (86 mg, 0.53 mmol), triethylamine (0.5 ml) and N-{4-[(1R)-1-aminoethyl]phenyl}methanesulfonamide hydrochloride (125 mg, 0.50 mmol, *Bioorganic & Medicinal Chemistry Letters*, 2004, 14, 1751–1755) were treated in the same procedure described in Example 2(b) to give 91 mg (40% yield) of the titled compound as a white solid.

$^1$H NMR (270 MHz, DMSO-d$_6$) δ ppm 1.38 (3H, d, J=7.3 Hz), 1.41 (9H, s), 2.94 (3H, s), 4.53 (2H, s), 4.97 (1H, m), 6.85 (1H, dd, J=2.6, 8.6 Hz), 6.99 (1H, d, J=2.6 Hz), 7.14 (2H, s, J=7.9 Hz), 7.26 (2H, d, J=7.9 Hz), 7.36 (1H, d, J=9.2 Hz), 8.49 (1H, d, J=7.9 Hz), 9.67 (1H, brs).

MS (ESI) m/z: 439 [M+H]$^+$, 437 [M−H]$^-$

Example 15

2-(4-tert-Butyl-3-chlorophenoxy)-N-((1R)-1-{3-fluoro-4-[(methylsulfonyl)amino] phenyl}ethyl)acetamide

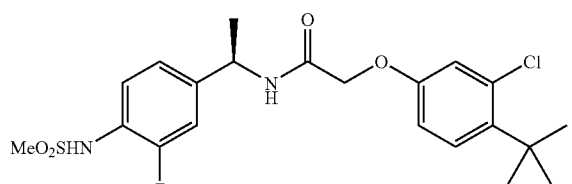

(4-tert-Butyl-3-chlorophenoxy)acetic acid (121 mg, 0.50 mmol), 2-chloro-1,3-dimethylimidazolinium chloride (CDI) (86 mg, 0.53 mmol), triethylamine (0.5 ml) and N{4-[(1R)-1-aminoethyl]-2-fluorophenyl}methanesulfonamide hydrochloride (134 mg, 0.50 mmol, WO 2005003084A1) were mixed in the same procedure described in Example 2(b) to give 68 mg (30% yield) of the title compound as a white solid.

$^1$H NMR (270 MHz, DMSO-d$_6$) δ ppm 1.38 (3H, d, J=7.3 Hz), 1.41 (9H, s), 2.99 (s, 3H), 4.55 (2H, s) 4.99 (1H, m), 6.86 (1H, dd, J=2.6, 9.2 Hz), 7.00 (1H, d, J=2.6 Hz), 7.16

(2H, m), 7.31 (1H, t, J=7.9 Hz), 7.37 (1H, d, J=9.2 Hz), 8.57 (1H, d, J=7.9 Hz), 9.55 (1H, brs).

MS (ESI) m/z 457: [M+H]⁺, 455 [M−H]⁻

Example 16

2-(4-tert-Butyl-3-chlorophenoxy)-N-{3-methyl-4-[(methylsulfonyl)amino]benzyl}acetamide

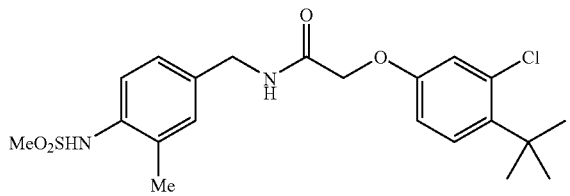

(4-tert-Butyl-3-chlorophenoxy) acetic acid (121 mg, 0.50 mmol), 2-chloro-1,3-dimethylimidazolinium chloride (CDI) (86 mg, 0.53 mmol), Et₃N (0.50 ml) and N-[4-(aminomethyl)-2-methylphenyl]methanesulfonamide hydrochloride (125 mg, 0.50 mmol) were mixed in the same procedure described Example 2(b) to give 2-(4-tert-butyl-3-fluorophenoxy)-N-{3-methyl-4-[(methylsulfonyl)amino]benzyl}acetamide.

$^1$H NMR (270 MHz, DMSO- d₆) δ ppm 1.41 (9H, s), 2.26 (3H, s), 2.93 (3H, s), 4.28 (2H, d, J=5.9 Hz), 4.57 (2H, s), 6.89 (1H, dd, J=2.6, 9.2 Hz), 7.01–7.08 (3H, m), 7.20 (1H, md, J=8.6 Hz), 7.39 (1H, d, J=8.6 Hz), 8.64 (1H, m), 9.00 (1H, brs).

MS (ESI) m/z: 439 [M+H]⁺, 437 [M−H]⁻

Example 17

2-(4-tert-Butyl-3-chlorophenoxy)-N-((1R)-1-3-methyl-4-[(methylsulfonyl)amino]phenylethyl)acetamide 17(a): 4-Acetyl-2-methylphenyl trifluoromethanesulfonate

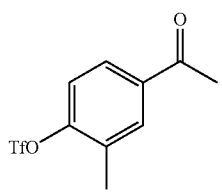

To a stirred solution of 1-(4-hydroxy-3-methylphenyl) ethanone (6.0 g, 40 mmol, WO 9964415A1) in methylene dichloride (100 ml) was added triflic anhydride (8.7 ml, 52 mmol) and triethylamine (10 ml) successively. After being stirred for 16 hours at ambient temperature, the reaction mixture was quenched with water and crude product was extracted with methylene dichloride. The organic layer was dried over sodium sulfate and concentrated in vacuo. The crude material was applied to a silica gel chromatography column and eluted with a volume mixture of methylene dichloride/ethyl acetate (5/1) to furnish 9.6 g (85% yield) of the title compound as yellow liquid.

$^1$H NMR (270 MHz, CDCl₃) δ ppm 2.45 (3H, s), 2.62 (3H, s), 7.35 (1H, d, J=8.6 Hz), 7.86 (1H, dd, J=8.6, 2.5 Hz), 7.92 (1H, s).

17(b): N-(4-Acetyl-2-methylphenyl)methanesulfonamide

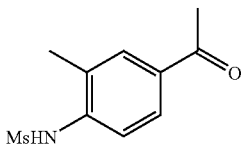

A test tube for microwave was charged with tris(dibenzylidenacetone)dipalladium (0) chloroform adduct (205 mg, 0.20 mmol), 9,9-dimethyl-9H-xanthene-4,5-diyl)bis[diphenylphosphine] (345 mg, 0.60 mmol), 4-acetyl-2-methylphenyl trifluoromethanesulfonate (1.41 g, 5.0 mmol), methanesulfonamide (570 mg, 6.0 mmol), cesium carbonate (1.63 g, 7.0 mmol) and 1,4-dioxane (5 ml). The mixture was subjected to microwave irradiation at 120° C. with stirring for 10 minutes. Then, it was filterd off and the filtrate was concentrated under reduced pressure to furnish the crude residue which was applied to a silica gel chromatography column and eluted with a volume mixture of hexane:ethyl acetate (2/1) to give 390 mg (34% yield) of the title compound as a yellow solid.

$^1$H NMR (270 MHz, CDCl₃) δ ppm 2.34 (3H, s), 2.59 (3H, s), 3.11 (3H, s), 6.47 (1H, brs), 7.58 (1H, d, J=8.1 Hz), 7.84 (2H, m).

MS (ESI) m/z: 228 [M+H]⁺, 226 [M−H⁻.

17(c): N-[4-((1R)-1-{[(R)-tert-Butylsulfinyl]amino}ethyl)-2-methylphenyl]methanesulfonamide

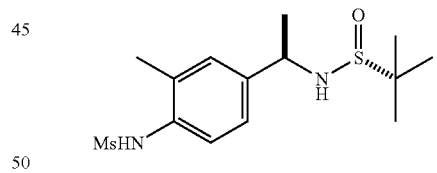

To a solution of titanium (IV) ethoxide (1.32 g, 5.8 mol) and N-(4-acetyl-2-methylphenyl)methanesulfonamide (800 mg, 3.5 mmol) in tetrahydrofuran (20 ml) was added (R)-(+)-2-methyl-2-propanesulfininamide (423mg, 350 mmol, Advanced Asymmetry). The mixture was heated at 70° C. and stirred for 16 hours. It was quenched with water and the resulting white precipitate was filtered off. The filtrate was partitioned between ethyl acetate and water. The organic layer was separated, dried over sodium sulfate. Then, filtration to remove sodium sulfate, evaporation under removed pressure gave the residue, which was applied to a silica gel chromatography column and eluted with a volume mixture of hexane:ethyl acetate (4/1). The given yellow oil was dissolved in tetrahydrofuran (10 ml) and the solution was added to sodium borohydride (242 mg, 6.4 mmol) in tetrahydrofuran (10 ml) at −70° C. The mixture was stirred at −70° C. for 5 hours and then quenched with methanol. It was stirred at room temperature for 1 hour and concentrated under reduced pressure to furnish 530 mg (45% yield) of the title compound as a yellow solid.

MS (ESI): m/z 333 [M+H]$^+$, 331 [M−H]$^-$.

17(d): N-{4-[(1R)-1-Aminoethyl]-2-methylphenyl}methanesulfonamide hydrochloride

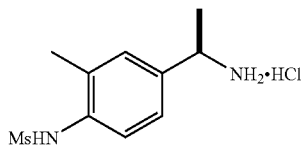

To N-[4-((1R)-1-{[(R)-tert-butylsulfinyl]amino}ethyl)-2-methylphenyl]methanesulfonamide (530 mg, 1.60 mmol) was added 10% methanolic hydrogen chloride (5.0 ml) and dioxane (5.0 ml). The solution was stirred at ambient temperature for 30 minutes and then concentrated under reduced pressure. Diethyl ether was added to precipitate amine hydrochloride. The precipitate was then filtered, washed with diethyl ether and collected to furnish 450 mg (quant.) of the title compound as a white solid.

$^1$H NMR (270 MHz, DMSO-$d_6$) δ ppm 1.45 (3H, m), 2.31 (3H, s), 2.98 (3H, s), 4.27 (1H, m), 7.31–7.38 (3H, m).

MS (ESI): m/z 227 [M−H]$^-$.

17(e): 2-(4-tert-Butyl-3-chlorophenoxy)-N-((1R)-1-{3-methyl-4[(methylsulfonyl)amino]phenyl}ethyl)acetamide

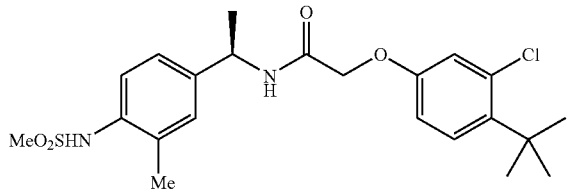

(4-tert-Butyl-3-chlorophenoxy) acetic acid (121 mg, 0.50 mmol), 2-chloro-1,3-dimethylimidazolinium chloride (CDI) (86 mg, 0.53 mmol), triethylamine and N{(1R)-1-aminoethyl]-2-methylphenyl}methanesulfonamide hydrochloride (132 mg, 0.50 mmol) were mixed in the same procedure described in Example 2(b) to give 71 mg (32% yield) of the title compound as a white solid.

$^1$H NMR (270 MHz, DMSO-$d_6$) δ ppm 1.38 (3H, d, J=6.6 Hz), 1.40 (9H, s), 2.26 (3H, s), 2.94 (3H, s), 4.54 (2H, s), 4.95 (1H, m), 6.86 (1H, dd, J=2.6, 8.6 Hz), 7.00 (1H, d, J=2.6 Hz), 7.10–7.21 (3H, m), 7.36 (1H, d, J=8.6 Hz), 8.51 (1H, d, J=7.9 Hz), 9.67 (1H, brs).

MS (ESI) m/z: 453 (M+H)$^+$, 451 (M−H)$^-$

Example 18

2-(4-tert-Butyl-3-fluorophenoxy)-N-((1R)-1-{4-[(methylsulfonyl)amino]phenyl}ethyl)acetamide

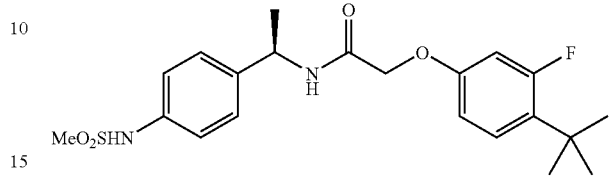

(4-tert-Butyl-3-fluorophenoxy)acetic acid (135 mg, 0.60 mmol), 2-chloro-1,3-dimethylimidazolinium chloride (CDI) (102 mg, 0.63 mmol), triethylamine (0.5 ml) and N-{4-[(1R)-1-aminoethyl]phenyl}methanesulfonamide hydrochloride (150 mg, 0.60 mmol) were mixed in the same procedure described in Example 2(b) to furnish 94 mg (37% yield) of the title compound as a white solid.

$^1$H NMR (CDCl$_3$) δ ppm 1.43 (9H, s), 1.54 (3H, d, J=7.3 Hz), 3.01 (3H, s), 4.44 (2H, d, J=2.6 Hz), 5.19 (1H, m), 6.40 (2H, d, J=12 Hz), 6.65 (1H, d), 7.19 (2H, d, J=8.6 Hz), 7.30 (2H, m).

MS (ESI) m/z: 423 [M+H]$^+$, 421 [M−H]$^-$

Example 19

2-(4-tert-Butyl-3-fluorophenoxy)-M((1R)-1-{3-fluoro-4-[(methylsulfonyl)amino]phenyl}ethyl)acetamide

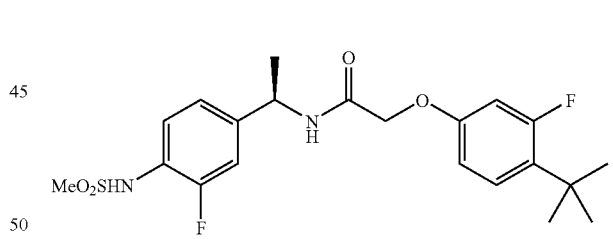

(4-tert-Butyl-3-fluorophenoxy) acetic acid (153 mg, 0.68 mmol), 2-chloro-1,3-dimethylimidazolinium chloride (CDI) (110 mg, 0.68 mmol), triethylamine (0.5 ml) and N-(4-[(1R)-1-aminoethyl]-2-fluorophenyl}methanesulfonamide hydrochloride (183 mg, 0.68 mmol) were mixed in the same procedure described in Example 2(b) to furnish 64 mg (21% yield) of the title compound as a white solid.

$^1$H NMR (300 MHz, CDCl$_3$) δ ppm 1.35 (9H, s), 1.52 (3H, d, J=6.6 Hz), 3.03 (3H, s), 4.48 (2H, d, J=2.9 Hz), 5.18 (1H, m), 6.44 (1H, brs), 6.60–6.72 (3H, m), 7.23 (1H, m), 7.53 (1H, t, J=8.0 Hz).

MS (ESI) m/z: 441 [M+H]$^+$, 439 [M−H]$^-$

Example 20

2-(4-tert-Butyl-3-fluorophenoxy)-N-{3-methyl-4-[(methylsulfonyl)amino]benzyl}acetamide

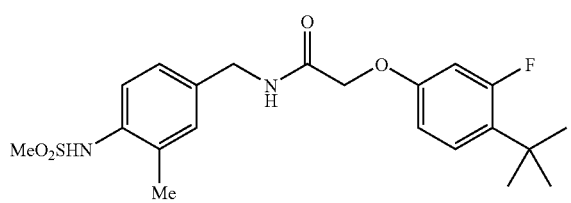

(4-tert-Butyl-3-fluorophenoxy) acetic acid (339 mg, 1.5 mmol), 1-ethyl-3-(3'-dimethylaminopropyl)carbodiimide hydrochloride (EDC) (518 mg, 2.7 mmol), 4-(dimethylamino)pyridine (DMAP) (55 mg, 0.45 mmol), triethylamine (0.836 ml) and N-[4-(aminomethyl)-2-methylphenyl]methanesulfonamide hydrochloride (451 mg, 1.8 mmol) were mixed in the same procedure described in Example 2(b) to give 105 mg (17% yield) of the title compound as a white solid.

$^1$H NMR (270 MHz, CDCl$_3$) δ ppm 1.35 (9H, s), 2.30 (3H, s), 3.02 (3H, s), 4.50 (2H, d, J=5.9 Hz), 4.53 (2H, s), 6.14 (1H, brs), 6.58–6.67 (2H, m), 6.58 (1H, brs), 7.13–7.25 (3H, m), 7.40–7.44 (1H, m).

MS (ESI) m/z: 423 [M+H]$^+$, 421 [M−H]$^−$

Example 21

(4-tert-butyl-3-fluorophenoxy)-N-((1R)-1-{3-methyl-4-[(methylsulfonyl)amino]phenyl}ethyl)acetamide

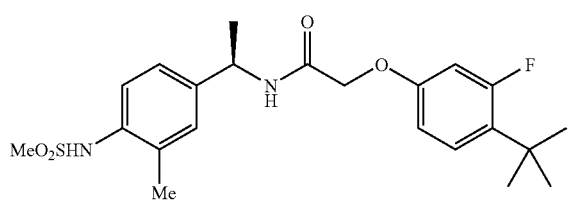

(4-tert-Butyl-3-fluorophenoxy) acetic acid (153 mg, 0.68 mmol), 2-chloro-1,3-dimethylimidazolinium chloride (CDI) (110 mg, 0.68 mmol), triethylamine (0.5 ml) and N-{4-[(1R)-1-aminoethyl]-2-methylphenyl}methanesulfonamide hydrochloride (180 mg, 0.68 mmol) were mixed in the same procedure described in Example 2(b) to give 129 mg (44% yield) of the title compound as a white solid.

$^1$H NMR (300 MHz, CDCl$_3$) δ ppm 1.35 (9H, s), 1.52 (3H, d, J=7.3 Hz), 2.30 (3H, s), 3.02 (3H, s), 4.47 (2H, d, J=3.3 Hz), 5.17 (1H, m), 6.07 (1H, brs), 6.64 (3H, m), 7.15 (2H, m), 7.40 (1H, m).

MS (ESI) m/z: 435 [M−H]$^−$

Example 22

2-(4-tert-Butylphenoxy)-N-{4-[(ethylsulfonyl)amino]benzyl}acetamide

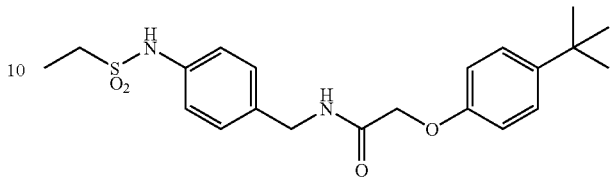

To a N,N-dimethylformamide (DMF) (5 ml) solution of (4-tert-butylphenoxy)acetic acid (330 mg, 1.50 mmol) and N-[4-(aminomethyl)phenyl]ethanesulfonamide hydrochloride (451 mg, 1.80 mmol, Journal of Medicinal Chemistry 2003, 46(14), 3116–3126), 1-ethyl-3-(3'-dimethylaminopropyl)carbodiimide hydrochloride (EDC) (431 mg, 2.25 mmol), 4-(dimethylamino)pyridine (DMAP) (46 mg, 0.38 mmol) and triethylamine (506 mg, 5.0 mmol) were added and the mixture was stirred for 15 hours at ambient temperature. The reaction mixture was then quenched with saturated aqueous solution of sodium bicarbonate and then crude products were extracted with methylene dichloride. The organic layer was then washed with brine, dried over sodium sulfate. After filtration to separate solvent and sodium sulfate, the solvent was removed under reduced pressure to give a residue, which was applied to an amino bound silica gel chromatography column and eluted with methylene dichloride/methanol=100/1 to furnish the title compound. Further, the title compound was recrystallized from ethyl acetate and hexane to furnish 341 mg (56% yield) of the title compound as a white solid.

$^1$H NMR (DMSO-d$_6$, 270 MHz) δ ppm 1.13–1.21 (3H, m), 1.25 (9H, s), 2.98–3.09 (2H, m), 4.25–4.32 (2H, m), 4.51 (2H, s), 6.85–6.93 (2H, m), 7.10–7.21 (4H, m), 7.28–7.35 (2H, m), 8.54–8.62 (1H, m), 9.73 (1, brs).

MS (ESI) m/z: 405 (M+H)$^+$, 403(M−H)$^−$.

Example 23

2-[4-(1,1-Dimethylpropyl)phenoxyl-N-{3-fluoro-4-[(methylsulfonyl)amino]benzyl}acetamide

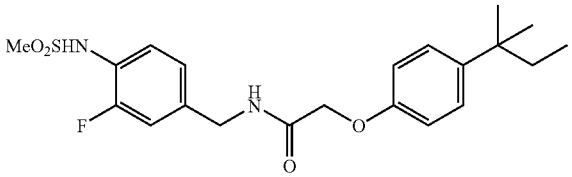

To an N,N-dimethylformamide (DMF) (10 ml) solution of [4-(1,1-dimethylpropyl)phenoxy]]acetic acid (330 mg, 1.50 mmol, Jpn. Kokai Tokkyo Koho JP 07304710(1995), 13 pp) and N{4-(aminomethyl)-2-fluorophenyl]methanesulfonamide hydrochloride (458 mg, 1.80 mmol), 1-ethyl-3-(3'- dimethylaminopropyl)carbodiimide hydrochloride (EDC) (431 mg, 2.25 mmol), 4-(dimethylamino)pyridine (DMAP) (55 mg, 0.45 mmol) and triethylamine (607 mg, 6.0 mmol) were added and the mixture was stirred for 15 hours at ambient temperature. The reaction mixture was then quenched with saturated aqueous solution of sodium bicarbonate and then crude products were extracted with methylene dichloride. The organic layer was then washed with brine, dried over sodium sulfate. After filtration to separate solvent and sodium sulfate, the solvent was removed under reduced pressure to give a residue, which was applied to an amino bound silica gel chromatography column and eluted with methylene dichloride/methanol=10/1 to furnish the title compound. Further, the title compound was recrystallized from ethyl acetate and hexane to furnish 344 mg (54% yield) of the title compound as a white solid.

$^1$H NMR (270 MHz DMSO- $d_6$) δ ppm 0.56–0.65 (3H, m), 1.21 (6H, s), 1.52–1.65 (2H, m), 2.99 (3H, s), 4.29–4.35 (2H, m), 4.53 (2H, s), 6.86–6.94 (2H, m), 7.02–7.17 (2H, m), 7.21–7.35 (3H, m), 8.62–8.71 (1H, m), 9.54 (1H, brs).

MS (ESI) m/z: 423 [M+H]$^+$, 421 [M−H]$^−$

Example 24

2-(4-tert-Butylphenoxy)-N-(3,5-difluoro-4-[(methylsulfonyl)amino]benzyl}-acetamide 24(a): N-(4-Bromo-2,6-difluorophenyl)-N4methylsulfonyl)methanesulfonamide

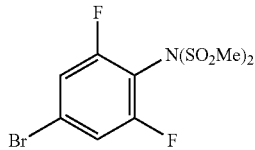

A mixture of 4-bromo-2,6-difluoroaniline (2.62 g, 12.6 mmol), methanesulfonyl chloride (1.73 g, 15.1 mmol) and 4-(dimethylamino)pyridine (461 mg, 3.78 mmol) in anhydrous pyridine (35 ml) was stirred for 15 hours at ambient temperature. The mixture was diluted with ethyl acetate (15 ml) and washed with 2M hydochloride aqueous solution until the aqueous pH 2, brine, dried over sodium sulfate. After filtration to separate solvent and sodium sulfate, the solvent was removed under reduced pressure to give a residue, which was applied to a silica gel chromatography column and eluted with hexane/ethyl acetate =5/1 to furnish 2.20 g (48 % yield) of the title compound as a white solid.

$^1$H NMR (DMSO-$d_6$, 270 MHz) δ ppm 3.55 (6H, s), 7.78–7.85 (2H, m).

24(b): N-(4-Bromo-2,6-difluorophenyl)methanesulfonamide

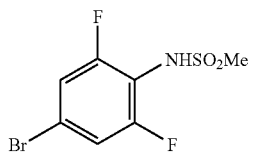

A mixture of N-(4-bromo-2,6-difluorophenyl)-N-(methylsulfonyl)methanesulfonamide (2.20 g, 6.04 mmol) and sodium hydroxide (pellet) (1.20 g, 30.0 mmol) in tetrahydrofuran. (30 ml) and water (10 ml) was stirred for 2 hours at ambient temperature. After the solvent was evaporated in vacuo and the residue was acidified to pH 2 with 2M hydrochloride aqueous solution. The aqueous solution was extracted with ethyl acetate and the combined solution was washed with brine, dried over sodium sulfate. After filtration to separate solvent and sodium sulfate, the solvent was removed under reduced pressure to give a residue, which was recrystallized from ethyl acetate and hexane to furnish 1.55 g (90% yield) of the title compound as a white solid.

$^1$H NMR (DMSO- $d_6$, 270 MHz) δ ppm 3.07 (3H, s), 7.56–7.65 (2H, m), 9.62 (1H, brs).

24(c): N-[4-(Aminomethyl)-2,6-difluorophenyl] methanesulfonamide hydrochloride and it's salt

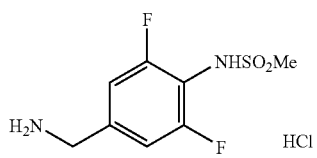

A mixture of N(4-bromo-2,6-difluorophenyl)methanesulfonamide (1.48 g, 5.17 mmol), zinc cyanide (760 mg, 6.47 mmol) and tetrakis(triphenylphosphine)palladium (0) (600 mg, 0.52 mmol) in anhydrous N,N-dimethylformamide (12 ml) was subjected to microwave irradiation at 110° C. with stirring for 20 min. Then, the mixture was diluted with ethyl acetate and toluene (8:1) solution (50 ml) and washed with water. The combined solution was washed with brine, dried over sodium sulfate. After filtration to separate solvent and sodium sulfate, the solvent was removed under reduced pressure to give a residue, which was applied to a silica gel chromatography column and eluted with hexane/ethyl acetate=3/2 to furnish 1.02 g (82 % yield) of the title compound as a white solid.

A mixture of N-(4-cyano-2,6-difluorophenyl)methanesulfonamide (1.01 g, 4.35 mmol) in methanol (15 ml), tetrahydrofuran (15 ml) and 12 M aqueous solution of hydrogen chloride (5 ml) was hydrogenated over 10% palladium-carbon (250 mg) under ballon pressure for 3 h at ambient temperature. The catalyst was filtered through a pad of celite and the filter cake was washed with methanol. After the filtrate and washings were evaporated in vacuo, the residue was recrystallized from methanol and diisopropyl ether to give to furnish 953 mg (80% yield) of the title compound as a white solid.

$^1$H NMR (DMSO-$d_6$, 300 MHz) δ ppm 3.07 (3H, s), 4.05 (2H, s), 7.38–7.46 (2H, m), 8.81 (2H, brs)

MS (ESI) m/z: 235 [M−H$^−$.

24(d): 2-(4-tert-Butylphenoxy)-N-3,5-difluoro-4-[(methylsulfonyl)amino]benzyl}-acetamide

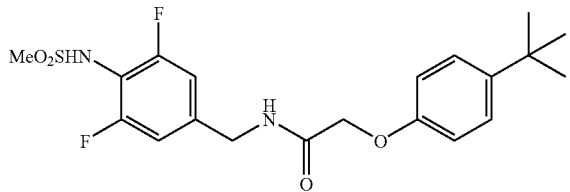

To an N,N-dimethylformamide (DMF) (10 ml) solution of (4-tert-butylphenoxy)acetic acid (330 mg, 1.50 mmol) and N-[4-(aminomethyl)-2,6-difluorophenyl]methanesulfonamide hydrochloride (491 mg, 1.80 mmol), 1-ethyl-3-(3'-dimethylaminopropyl)carbodiimide hydrochloride (EDC) (431 mg, 2.25 mmol), 4-(dimethylamino)pyridine (DMAP) (55 mg, 0.45 mmol) and triethylamine (607 mg, 6.0 mmol) were added and the mixture was stirred for 15 hours at ambient temperature. The reaction mixture was then quenched with saturated aqueous solution of sodium bicarbonate and then crude products were extracted with methylene dichloride The organic layer was then washed with brine, dried over sodium sulfate. After filtration to separate solvent and sodium sulfate, the solvent was removed under reduced pressure to give a residue, which was applied to an amino bound silica gel chromatography column and eluted with methylene dichloride/methanol=10/1 to furnish the title compound. Further, the title compound was recrystallized from ethyl acetate and hexane to furnish 199 mg (31% yield) of the title compound as a white solid.

$^1$H NMR (DMSO-d$_6$, 270 MHz) δ ppm 1.25 (9H, s), 3.03 (3H, s), 4.31–4.36 (2H, m), 4.56 (2H, s), 6.86–6.94 (2H, m), 6.98–7.07 (2H, m), 7.28–7.36 (2H, m), 8.65–8.75 (1H, m), 9.48 (1H, brs)

MS (ESI) m/z: 427 [M+H]$^+$, 425 [M−H]$^-$

Example 25

2-[(5,5-Dimethyl-5,6,7,8-tetrahydronaphthalen-2-yl)oxyl-N-{3-methyl-4-[(methylsulfonyl)amino]benzyl}acetamide

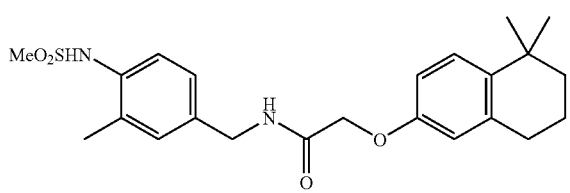

To an N,N-imethylformamide (DMF) (10 ml) solution of [(5,5-dimethyl-5,6,7,8-tetrahydronaphthalen-2-yl)oxy]acetic acid (351 mg, 1.50 mmol) and N44-(aminomethyl)-2-methylphenyl]methanesulfonamide hydrochloride (451 mg, 1.80 mmol), 1-ethyl-3-(3'-dimethylaminopropyl)carbodiimide hydrochloride (EDC) (431 mg, 2.25 mmol), 4-(dimethylamino)pyridine (DMAP) (55 mg, 0.45 mmol) and triethylamine (607 mg, 6.0 mmol) were added and the mixture was stirred for 15 h at ambient temperature. The reaction mixture was then quenched with saturated aqueous solution of sodium bicarbonate and then crude products were extracted with methylene dichloride. The organic layer was then washed with brine, dried over sodium sulfate. After filtration to separate solvent and sodium sulfate, the solvent was removed under reduced pressure to give a residue, which was applied to an amino bound silica gel chromatography column and eluted with methylene dichloride/methanol=100/1 to furnish 352 mg (55% yield) of the title compound as white amorphous solid.

$^1$H NMR (270 MHz, CDCl$_3$) δ ppm 1.25 (6H, s), 1.60–1.86 (4H, s), 2.30 (3H, s), 2.69–2.77 (2H, m), 3.02 (3H, s), 4.47–4.54 (4H, m), 6.57–6.61 (1H, m), 6.70–6.76 (1H, m), 6.93 (1H, brs), 7.10–7.17 (2H, m), 7.24–7.30 (2H, m), 7.38–7.44 (1H, m).

MS (ESI) m/z: 431 [M+H]$^+$, 429 [M−H]$^-$

Example 26

2-[(1,1-dimethyl-2,3-dihydro-1H-inden-5-yl)oxy]-N-13-fluoro-4-[(methylsulfonyl)amino] benzyl}acetamide

26(a): 5-Methoxy-1,1-dimethylindane

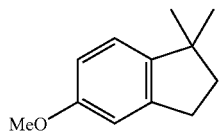

To a stirred solution of titanium chloride (4.91 g, 25.9 mmol) in anhydrous dichloromethane (30 ml) was added 1.01 M dimethyl zinc toluene solution (25.6 ml, 25.9 mmol) at −45° C. under nitrogen and the mixture was stirred for 10 minutes at −45° C. To the mixture was added a solution of 5-methoxy-1-indanone (2.0 g, 12.3 mmol) in anhydrous dichloromethane (15 ml) dropwise at −45° C. and the mixture was warmed to ambient temperature. After 3 hours at ambient temperature, the mixture was poured into ice-water and the aqueous solution was extracted with ethyl acetate (x 3). The combined solution was washed with brine, dried over sodium sulfate. After filtration to separate solvent and sodium sulfate, the solvent was removed under reduced pressure to give a residue, which was applied to a silica gel chromatography column and eluted with hexane/ethyl acetate =50/1–30/1 to furnish 941 mg (43% yield) of the title compound as colorless oil.

$^1$H NMR (270 MHz, CDCl$_3$) δ ppm 1.23 (6H, s), 1.88–1.96 (2H, m), 2.82–2.90 (2H, m), 3.78 (3H, s), 6.70–6.78 (2H, m), 7.00–7.07(1H, m)

26(b): 1,1-Dimethylindan-5-ol

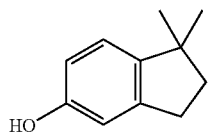

To a stirred solution of 5-methoxy-1,1-dimethylindane (941 mg, 5.34 mmol) in anhydrous dichloromethane (20 ml) was added 1.0 M boron tribromide dichloromethane solution (10.7 ml, 10.7 mmol) via a syringe at −78° C. The mixture was warmed to ambient temperature and stirred for 1.5 hours. The mixture was quenched with water (15 ml) and extracted with dichloromethane. The combined solution was washed with brine, dried over sodium sulfate. After filtration to separate solvent and sodium sulfate, the solvent was removed under reduced pressure to give 878 mg of the crude 1,1-dimethylindan-5-ol as a gray solid.

26(c): Ethyl [(1,1-dimethyl-2,3-dihydro-1H-inden-5-yl)oxy]acetate

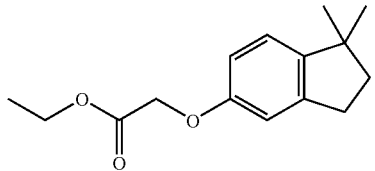

To a stirred suspension of 60% sodium hydride (240 mg, 5.87 mmol) in anhydrous tetrahydrofuran (5 ml) was added a solution of crude 1,1-dimethylindan-5-ol (878 mg) in anhydrous tetrahydrofuran (10 ml) dropwise at 0° C. After 15 minutes at 0° C., to this was added ethyl bromoacetate (1.16 g, 6.94 mmol) via a syringe at 0° C. After 2 hours at ambient temperature, the mixtute was quenched with water (15 ml) and extracted with ethyl acetate. The combined solution was washed with brine, dried over sodium sulfate. After filtration to separate solvent and sodium sulfate, the solvent was removed under reduced pressure to give a residue, which was applied to a silica gel chromatography column and eluted with hexane/ethyl acetate=8/1–6/1 to furnish 890 mg (67% yield in 2 steps) of the title compound as a pale yellow oil.

$^1$H NMR (CDCl$_3$, 270 MHz) δ ppm 1.22 (6H, s), 1.26–1.34 (3H, m), 1.87–1.95 (2H, m), 2.78–2.88 (2H, m), 4.22–4.32 (2H, m), 4.59 (3H, s), 6.68–6.76 (2H, m), 6.97–7.05(1H, m)

26(d): [(1,1-Dimethyl-2,3-dihydro-1H-inden-5-yl)oxy]acetic acid

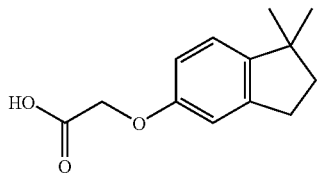

A mixture of ethyl [(1,1-dimethyl-2,3-dihydro-1H-inden-5-yl)oxy]acetate (1.14 g, 4.58 mmol) in ethanol (20 ml) and 2M sodium hydroxide aqueous solution (4 ml) was refluxed for 2 hours. After cooling to ambient temperature, the solvent was evaporated in vacuo and the aqueous solution was acidified to pH 2 with 2M hydrochloride aqueous solution with ice-cooling. The precipitate solid was collected and dried in vacuo to give 894 mg (89% yield) of the title compound as a pale gray solid.

$^1$H NMR (300 MHz, DMSO-d$_6$) δ ppm 1.18 (6H, s), 1.81–1.89 (2H, m), 2.75–2.83 (2H, m), 4.57 (2H, s), 6.64–6.72 (2H, m), 7.01–7.06(1H, m)

MS (ESI) m/z: 219 [M–H]$^-$.

26(e): 2-[(1,1-Dimethyl-2,3-dihydro-1H-inden-5-yl)oxy]-N-{3-fluoro-4-[(methylsulfonyl)amino]benzyl}acetamide

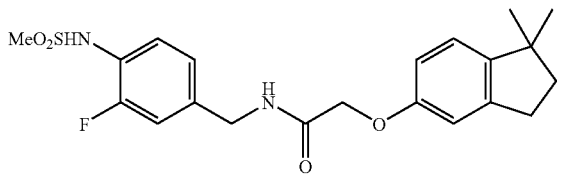

To a N,N-dimethylformamide (DMF) (5 ml) solution of [(1,1-dimethyl-2,3-dihydro-1Hinden-5-yl)oxy]acetic acid (330 mg, 1.50 mmol) and N-4-(aminomethyl)-2-fluorophenyl]methanesulfonamide hydrochloride (458 mg 1.80 mmol), 1-ethyl-3-(3'-dimethylaminopropyl)carbodiimide hydrochloride (EDC) (431 mg, 2.25 mmol), 4-(dimethylamino)pyridine (DMAP) (46 mg, 0.38 mmol) and triethylamine (506 mg, 5.0 mmol) were added and the mixture was stirred for 15 h at ambient temperature. The reaction mixture was then quenched with saturated aqueous solution of sodium bicarbonate and then crude products were extracted with methylene dichloride The organic layer was then washed with brine, dried over sodium sulfate. After filtration to separate solvent and sodium sulfate, the solvent was removed under reduced pressure to give aresidue, which was applied to an amino bound silica gel chromatography column and eluted with methylene dichloride/methanol=40/1–20/1 to furnish the title compound. Further, the title compound was recrystallized from ethyl acetate and hexane to furnish 283 mg (45% yield) of the title compound as a white solid.

$^1$H NMR (270 MHz, CDCl$_3$) δ ppm 1.24 (6H, s), 1.89–1.97 (2H, m), 2.81–2.90 (2H, m), 3.02 (3H, s), 4.49–4.56 (4H, m), 6.57 (1H, brs), 6.71–6.78 (2H, m), 6.94–7.11 (4H, m), 7.47–7.56 (1H, m).

MS (ESI) m/z: 421 [M+H]$^+$, 419 [M–H]$^-$

Example 27

2-(4-tert-Butylphenoxy)-N-{3-methyl-4-[(methylsulfonyl)amino]benzyl}acetamide

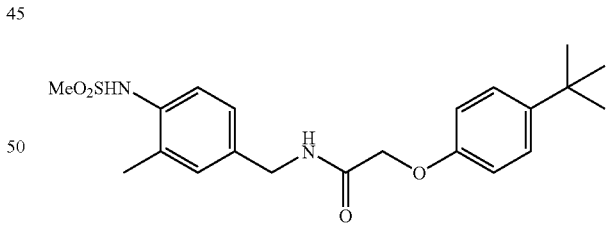

To a N,N-dimethylformamide (DMF) (15 ml) solution of (4-tert-butylphenoxy)acetic acid (312 mg, 1.50 mmol) and N-[4-(aminomethyl)-2-methylphenyl]methanesulfonamide hydrochloride (451 mg, 1.80 mmol), 1-ethyl-3-(3'-dimethylaminopr6pyl)carbodiimide hydrochloride (EDC) (518 mg, 2.70 mmol), 4-(dimethylamino)pyridine (DMAP) (55 mg, 0.45 mmol) and triethylamine (607mg, 6.0 mmol) were added and the mixture was stirred for 15 hours at ambient temperature. The reaction mixture was then quenched with saturated aqueous solution of sodium bicarbonate and then crude products were extracted with methylene dichloride. The organic layer was then washed with brine, dried over sodium sulfate. After filtration to separate solvent and sodium sulfate, the solvent was removed under reduced pressure to give a residue, which was applied to an amino bound silica gel chromatography column and eluted with methylene dichloride/methanol=100/1 to furnish 350 mg (58% yield) of the title compound as a white solid.

¹H NMR (CDCl₃, 270 MHz) δ ppm 1.30 (9H, s), 2.30 (3H, s), 3.01 (3H, s), 4.47–4.53 (2H, m), 4.55 (2H, s), 6.31 (1H, brs), 6.82–7.00 (3H, m), 7.10–7.18 (2H, m), 7.30–7.45 (3H, m).

MS (ESI) m/z: 405 [M+H]⁺, 403 [M−H]⁻

Example 28

2-[4-tert-Butyl-2-(Piperidin-1-ylmethyl)phenoxy]-N-((1R)-1-{3-methyl-4-[(methylsulfonyl)amino]phenyl}ethyl)acetamide 28(a): tert-Butyl (4-tert-butyl-2-formylphenoxy)acetate

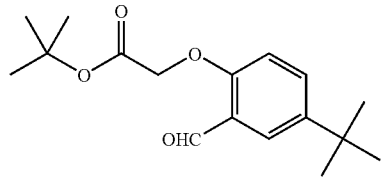

To an acetone/methanol=9:1 (1.6 ml) solution of 5-tert-butyl-2-hydroxybenzaldehyde (191 mg, 1.1 mmol), potassium carbonate (118 mg, 0.85 mmol) was added at ambient temperature under nitrogen atmosphere. After being stirred for 10 minutes, tert-butyl bromoacetic acetate (0.14 ml, 0.95 mmol) was added. The reaction mixture was stirred additionally for 2 hours at ambient temperature and then the resulting yellow solution was filtered. The filtrate was concentrated under reduced pressure to give a residue, which was applied to silica gel chromatography column and eluted with hexane/ethyl acetate=10/1 to furnish 207 mg (66% yield) of the title compound as slightly yellow oil.

¹H NMR (300 MHz, CDCl₃) δ ppm 1.31 (9H, s), 1.49 (9H, s), 4.63 (2H, s), 6.78 (1H, d, J=8.8 HZ), 7.56 (1H, dd, J=2.9, 8.8 Hz), 7.88 (1H, d, J=2.9 Hz), 10.57 (1H, s).

MS (ESI) m/z: 293 [M+H]⁺·

28(b): tert-Butyl [4-tert-2-(piperidine-1-ylmethyl)phenoxy]acetate

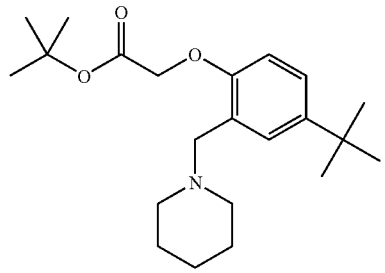

To a methanol (6.6 ml) solution of tert-butyl (4-tert-butyl-2-formylphenoxy)acetate (193 mg, 0.66 mmol), piperidine (0.33 ml, 3.3 mmol) and acetic acid (0.10 ml, 1.7 mmol) were added at ambient temperature under nitrogen atmosphere. After being stirred for 15 hours, a portion of sodium borohydride (37 mg, 0.98 mmol) was added and stirred for 0.5 hours at ambient temperature. The reaction mixture was quenched with saturated aqueous solution of ammonium chloride. The organic layer was washed with brine and dried over magnesium sulfate. After filtration to separate solvent and magnesium sulfate, the solvent was removed under reduced pressure to give a residue, which was applied to preparative TLC on silica gel and eluted with hexane/ethyl acetate=1/1 to furnish 81 mg (34% yield) of the title compound as pale yellow oil.

¹H NMR (300 MHz, CDCl₃) δ ppm 1.29 (9h, s), 1.48 (9H, s), 1.53–1.62 (6H, m), 2.41–2.48 (4H, m), 3.60 (2H, s), 4.49 (2H, s), 6.65 (1H, d, J=8.8 Hz), 7.17 (1H, dd, J=2.2, 8.8 Hz), 7.38 (1H, d, J=2.2 Hz).

MS (ESI) m/z: 362 [M+H]⁺.

28(c): [4-tert-Butyl-2-(Piperidine-1-ylmethyl)phenoxy]aceticacid

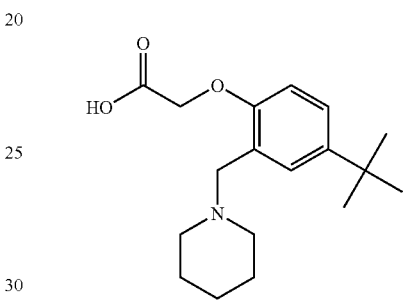

To a methylene dichloride (2.0 ml) solution of tert-butyl [4-tert-butyl-2-(piperidin-1-ylmethyl)phenoxy]acetate (75 mg, 0.21 mmol), trifluoroacetic acid (0.2 ml, 2.7 mmol) was added at ambient temperature under nitrogen atmosphere. After being stirred for 15 hours, additional trifluoroacetic acid (1.0 ml, 13.5 mmol) was added. After being stirred additionally for 10 hours, the resulting mixture was concentrated under reduced pressure and azeotrope with toluene to furnish 111 mg of the title compound as slightly yellow oil, which was used for the next reaction without further purification.

¹H NMR (300 MHz, CDCl₃) δ ppm 1.29 (9H, s), 1.84–1.98 (6H, m), 2.71–2.86 (4H, m), 3.50 (2H, m), 4.87 (2H, s), 6.99 (1H, d, J=8.8 Hz), 7.20 (1H, d, J=2.9 Hz), 7.47 (1H, dd, J=2.9, 8.8 Hz).

MS (ESI) m/z: 306 [M+H]⁺, 304 (M−H⁻.

28(d): 2-[4-tert-Butyl-2-(piperidine-1-ylmethyl)phenoxy]-N-((1R)-1-{3-methyl-4-[(methylsulfonyl)amino]phenyl}ethyl)acetamide

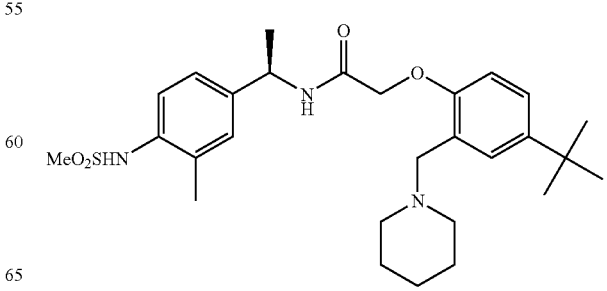

To a methylene dichloride (5.0 ml) solution of [4-tert-butyl-2-(piperidin-1-ylmethyl)phenoxy]acetic acid (111 mg) and N-{4-[(1R)-1-aminoethyl]-2-methylphenyl}methanesulfonamide hydrochloride (97 mg, 0.37 mmol), a portion of N-(3-dimethylaminopropyl)-N'-ethylcarbodiimide hydrochloride (109 mg, 0.57 mmol), triethylamine (0.2 ml, 1.4 mmol), and catalytic amount of 4-(dimethylamino)pyridine were added at ambient temperature under nitrogen atmosphere. After being stirred for 18 hours, the reaction mixture was diluted with methylene dichloride and quenched with saturated aqueous solution of ammonium chloride. The organic layer was then washed with brine and dried over magnesium sulfate. After filtration to separate solvent and magnesium sulfate, the solvent was removed under reduced pressure, which was applied to an amino bound silica gel chromatography column and eluted with methylene dichloride/methanol=40/1 to give oil which contained 4-(dimethylamino)pyridine. This crude product was purified by HPLC gradient from 0.05% aqueous solution of ammonium formate/acetonitrile=4/96 to 96/4 to furnish 9.1 mg (5% yield) of the title compound as a white solid.

$^1$H NMR (300 MHz, DMSO-$d_6$) δ ppm 1.31 (9H, m), 1.34–1.47 (6H, m), 1.50 (3H, d, J=7.3 Hz), 2.26 (3H, s), 2.28–2.46 (4H, m), 2.99 (3H, s), 3.41 (1H, d, J=12.5 Hz), 3.54 (1H, d, J=12.5 Hz), 4.55 (2H, s), 5.15–5.28 (1H, m), 6.77 (1H, d, J=8.8 Hz), 7.01–7.13 (2H, m), 7.18–7.26 (2H, m), 7.36 (1H, d, J=8.8 Hz).

MS (ESI) m/z: 516 [M+H]$^+$, 514 [M−H]$^−$.

Example 29

2-(4-tert-Butylphenoxy)-N-((1R)-1-{3-methyl-4-[(methylsulfonyl)amino]phenyl}ethyl)acetamide

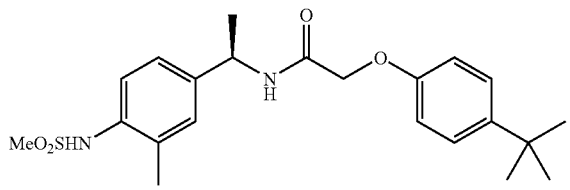

To a tetrahydrofuran (THF) (2.0 ml) solution of (4-tert-butylphenoxy)acetic acid (140 mg, 0.7 mmol) 1,1'-dicarbonyldiimidazole (110 mg, 0.7 mmol) was added and the mixture was stirred for 1 hour at ambient temperature. N-{4-[(1R)-1-aminoethyl]-2-methylphenyl}methanesulfonamide hydrochloride (180 mg, 0.7 mmol) and triethylamine (0.5 ml) were added to the mixture. After being stirred for 1 hour at ambient temperature, white precipitate appeared. It was filtered and the solvent was removed under reduced pressure to give a residue, which was applied to a silica gel chromatography column and eluted with methylene dichloride/ethyl acetate=1/1 to furnish 90 mg (31% yield) of the title compound as a white solid.

$^1$H NMR (270 MHz, CDCl$_3$) δ ppm 1.31 (9H, s), 1.51 (3H, d, J=6.6 Hz), 2.29 (3H, s), 3.02 (3H, s), 4.49 (2H, s), 5.18 (1H, m), 6.08 (1H, brs), 6.87 (2H, d, J=8.6 Hz), 7.15 (2H, m), 6.79 (1H, d, J=9.2 Hz), 7.35 (2H, d, J=8.6 Hz), 7.42 (1H, d, J=9.2 Hz).

MS (ESI) m/z: 419 (M+H]$^+$, 417 [M−H]$^−$.

Example 30

N-((1R)-1-{3-Methyl-4-[(methylsulfonyl)amino]phenyl}ethyl)-2-[4-(2,2,2-trifluoro-1,1-dimethylethyl)phenoxy]acetamide

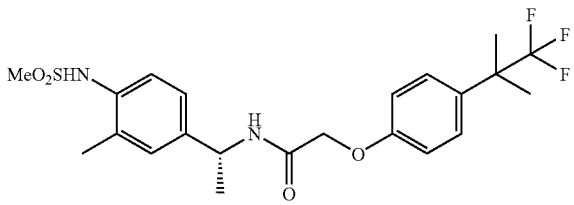

To a N,N-dimethylformamide (DMF) (3 ml) solution of [4-(2,2,2-trifluoro-1,1-dimethylethyl)phenoxy]acetic acid (131 mg, 0.5 mmol) and N-{4-[(1R)-1-aminoethyl]-2-methylphenyl}methanesulfonamide hydrochloride (132 mg, 0.5 mmol), 1-ethyl-3-(3'-dimethylaminopropyl)carbodiimide hydrochloride (EDC) (144 mg, 0.75 mmol), 1-hydroxybenzotriazole (HOBt) monohydrate (85 mg, 0.55 mmol) and triethylamine (0.21 ml) were added and the mixture was stirred for 2 hours at ambient temperature. The reaction mixture was then quenched with saturated aqueous solution of sodium bicarbonate and then crude products were extracted with ethyl acetate. The organic layer was then washed with brine, dried over sodium sulfate. After filtration to separate solvent and sodium sulfate, the solvent was removed under reduced pressure to give a residue, which was applied to a silica gel chromatography column and eluted with ethyl acetate/hexane=1/1 to furnish 92 mg (39% yield) of the title compound as a white solid.

$^1$H NMR (CDCl$_3$, 270 MHz) δ ppm 1.51 (3H, d, J=7.3 Hz), 1.57 (6H, s), 2.29 (3H, s), 3.02 (3H, s), 4.45–4.56 (2H, m), 5.11–5.21 (1H, m), 6.13 (1H, s), 6.73 (1H, d, J=8.1 Hz), 6.90–6.94 (2H, m), 7.13–7.17 (2H, m), 7.39–7.46 (3H, m).

MS (ESI) m/z: 473 [M+H]$^+$, 471 [M−H]$^−$

Example 31

2-[4-tert-Butyl-3-(2-methoxyethoxy)phenoxy]-N-{3-fluoro-4-[(methylsulfonyl)amino]benzyl}acetamide 31(a): tert-Butyl 4-tert-butyl-3-(2-methoxyethoxy)phenyl carbonate

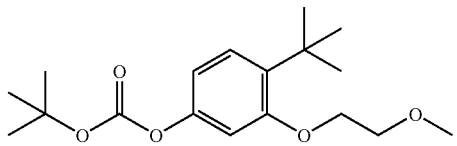

To a tetrahydrofuran (THF) (3 ml) solution of tert-butyl 4-tert-butyl-3-hydroxyphenyl carbonate (*J. Org. Chem.* 2001, 66, 3435) (266 mg, 1.0 mmol), 2-methoxy-ethanol (83 μL, 1.1 mmol) and triphenylphosphine (275 mg, 1.1 mmol) were added diethyl azodicarboxylate (DEAD) (165 μl, 1.1 mmol) and the mixture was stirred for 3 hours at 50° C. The solvent was removed under reduced pressure to give a residue, which was applied to a silica gel chromatography column and eluted with ethyl acetate/hexane=1/19 to furnish 0.23 g (71% yield) of the title compound as a yellow oil.

$^1$H NMR (CDCl$_3$, 270 MHz) δ ppm 1.30 (9H, s), 1.56 (9H, s), 3.44 (3H, s), 3.79 (2H, t, J=5.3 Hz), 1.97–2.11 (2H, m), 6.63 (2H, m), 7.25 (1H, d, J=8.5 Hz).

31(b): 4-tert-Butyl-3-(2-methoxyethoxy)phenol

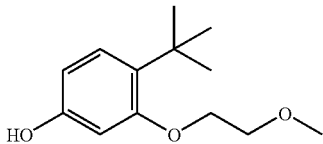

To a methylene dichloride (3 ml) solution of tert-butyl 4-tert-butyl-3-(2-methoxyethoxy)phenyl carbonate (792 mg, 2.4 mmol) was added trifluoroacetic acid (TFA) (3 ml) and the mixture was stirred for 1 hour at ambient temperature. The solvent was removed under reduced pressure to give a residue, which was applied to a silica gel chromatography column and eluted with ethyl acetate/hexane=⅓ to furnish 0.32 g (59% yield) of the title compound as a white solid.

$^1$H NMR (CDCl$_3$, 300 MHz) δ ppm 1.35 (9H, s), 3.45 (3H, s), 3.80 (2H, m), 4.09 (2H, t, J=4.6 Hz), 6.33 (1H, dd, J=2.6, 8.5 Hz), 6.41 (1H, d, J=2.6 Hz), 7.11 (1H, d, J=8.4 Hz).

31(c): Ethyl [4-tert-butyl-3-(2-methoxyethoxy)phenoxy]acetate

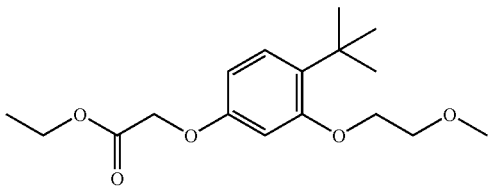

To a tetrahydrofuran (THF) (10 ml) suspension of sodium hydride (60% in mineral oil) (68 mg, 1.7 mmol) was added a tetrahydrofuran (THF) solution (5 ml) of 4-tert-butyl-3-(2-methoxyethoxy)phenol (320 mg, 1.4 mmol) and the mixture was stirred for 30 minutes at ambient temperature. To the mixture was added ethyl bromoacetate (190 ul, 1.7 mmol) at ambient temperature. The stirred mixture was refluxed for 4 hours. The reaction mixture was then quenched with saturated aqueous solution of ammonium chloride and then crude products were extracted with ethyl acetate The organic layer was then washed with brine, dried over sodium sulfate. After filtration to separate solvent and sodium sulfate, the solvent was removed under reduced pressure to give a residue, which was applied to a silica gel chromatography column and eluted with ethyl acetate/hexane=1/9 to furnish 0.26 g (60% yield) of the title compound as colorless oil.

$^1$H NMR (CDCl$_3$, 300 MHz) δ ppm 1.31 (3H, t, J=7.1 Hz), 1.35 (9H, s), 3.44 (3H, s), 3.80 (2H, m), 4.10 (2H, m), 4.28 (2H, q$_{AB}$, J=7.2 Hz), 4.58 (2H, s), 6.34 (1H, dd, J=2.5, 8.6 Hz), 6.54 (1H, d, J=2.6 Hz), 7.16 (1H, d, J=8.7 Hz).

MS (ESI) m/z: 311 [M+H]$^+$.

31(d): [4-tert-Butyl-3-(2-methoxyethoxy)phenoxy]acetic acid

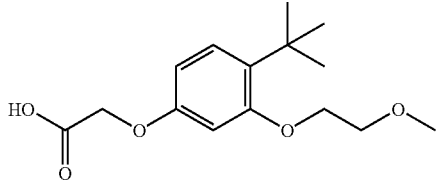

To a methanol (3 mL) solution of ethyl [4-tert-butyl-3-(2-methoxyethoxy)phenoxy]acetate (260 mg, 0.84 mmol) was added 2M potassium hydroxide solution (1 ml) at ambient temerature. The stirred mixture was refluxed at 90° C. for 30 minutes. The reaction mixture was then quenched with saturated aqueous solution of ammonium chloride and then crude products were extracted with ethyl acetate The organic layer was then washed with brine, dried over sodium sulfate. After filtration to separate solvent and sodium sulfate, the solvent was removed under reduced pressure to give a residue, which was applied to recrystallization from hexane to furnish 0.24 g (100% yield) of the title compound as a white solid.

$^1$H NMR (CDCl$_3$, 300 MHz) δ ppm 1.36 (9H, s), 3.17 (3H, s), 3.80 (2H, m), 4.10 (2H, m), 4.65 (2H, s), 6.37 (1H, dd, J=2.8, 8.6 Hz), 6.54 (1H, d, J=2.5 Hz), 7.18 (1H, d, J=8.7 Hz).

MS (ESI) m/z: 283 [M+H]$^+$.

31(e): 2-[4-tert-Butyl-3-(2-methoxyethoxy)phenoxy]-N-{3-fluoro-4-[(methylsulfonyl)amino]benzyl}acetamide

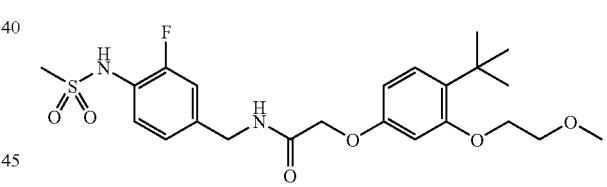

To a tetrahydrofuran (THF) (3 ml) solution of [4-tert-butyl-3-(2-methoxyethoxy)phenoxy]acetic acid (100 mg, 0.35 mmol) was added 1,1'-carbonyl-diimidazole (63 mg, 0.39 mmol) and the mixture was stirred for 1 hour at ambient temperature. To the mixture was added N-[4-(aminomethyl)-2-fluorophenyl]methanesulfonamide hydrochloride (99 mg, 0.39 mmol) and triethyl amine (150 ul, 1.1 mmol) and the mixture was stirred for 1 hour at ambient temperature. After filtration to separate solvent and the resulting percipitate, the solvent was removed under reduced pressure to give a residue, which was applied to a silica gel chromatography column and eluted with ethyl acetate/hexane=1/1 to furnish 78 mg (46% yield) of the title compound as a white solid.

$^1$H NMR (CDCl$_3$, 300 MHz) δ ppm 1.36 (9H, s), 3.02 (3H, s), 3.45 (3H, s), 3.79 (2H, t, J=5.1 Hz), 4.08 (2H, t, J=4.3 Hz), 4.52 (2H, d, J=6.3 Hz), 4.55 (2H, s), 6.32–6.50 (2H, m), 6.53 (1H, brs), 6.94 (1H, brs), 7.03–7.15 (1H, m), 7.19 (1H, d, J=8.4Hz), 7.52 (1H, t, J=8.1 Hz).

MS (ESI) m/z: 483[M+H]$^+$.

Example 32

2-[4-tert-Butyl-3-(cyclopropylmethoxy)phenoxy]-N{3-fluoro-4-[(methylsulfonyl)amino]benzyl}acetamide

32(a): tert-Buyl 4-tert-butyl-3-(cyclopropylmethoxy)phenyl carbonate

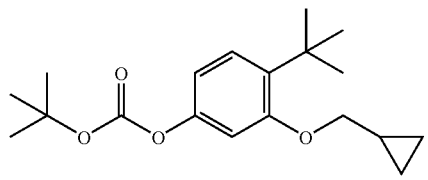

Tert-butyl 4-tert-butyl-3-hydroxyphenyl carbonate (1.5 g, 5.6 mmol), cyclopropylmethanol (0.5 mL, 6.2 mmol), triphenylphosphine (1.6 g, 6.2 mmol) and diethyl azodicarboxylate (DEAD) (1.0 mL, 6.2 mmol) were treated in the same procedure described in Example 31(a). The crude residue was applied to a silica gel chromatography column and eluted with a volume mixture of hexane and ethyl acetate (19/1 to 9/1) to furnish 1.42 g (79% yield) of the title compound as a yellow oil.

$^1$H NMR (CDCl$_3$, 300 MHz) δ ppm 0.29–0.39 (2H, m), 0.57–0.70 (2H, m), 1.38 (9H, s), 1.39 (1H, m), 1.55 (9H, s), 3.80 (2H, d, J=6.8 Hz), 6.61 (1H, d, J=2.4 Hz), 6.68 (1H, dd, J=2.3, 8.4 Hz), 7.24 (1H, d, J=8.6 Hz).

MS (ESI) m/z: 319 [M–H]$^-$.

32(b): 4-tert-Butyl-3-(cyclopropylmethoxy)phenol

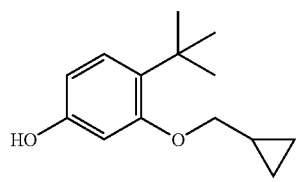

To a dioxane (10 mL) solution of tert-butyl 4-tert-butyl-3-(cyclopropylmethoxy)phenyl carbonate. (1.42 g, 4.43 mmol) was added 2M hydrochrolic acid (12 ml) at ambient temperature. The stirred mixture was refluxed for 18 hours. The reaction mixture was then quenched with saturated aqueous solution of sodium bicarbonate and then crude products were extracted with ethyl acetate. The organic layer was then washed with brine, dried over sodium sulfate. After filtration to separate solvent and sodium sulfate, the solvent was removed under reduced pressure to give a residue, which was applied to a silica gel chromatography column and eluted with hexane and ethyl acetate (9/1) to furnish 0.44 g (46% yield) of the title compound as a white solid.

$^1$H NMR (CDCl$_3$, 300 MHz) δ ppm 0.23–0.39 (2H, m), 0.56–0.69 (2H, m), 1.30 (1H, m), 1.39 (9H, s), 3.77 (2H, d, J=6.8 Hz), 4.69 (1H, s), 6.30 (1H, dd, J=2.5, 8.3 Hz), 6.35 (1H, d, J=2.6 Hz), 7.09 (1H, d, J=8.2 Hz).

MS (ESI) m/z: 219 [M–H]$^-$.

32(c): Ethyl [4-tert-butyl-3-(cyclopropylmethoxy)phenoxy]acetate

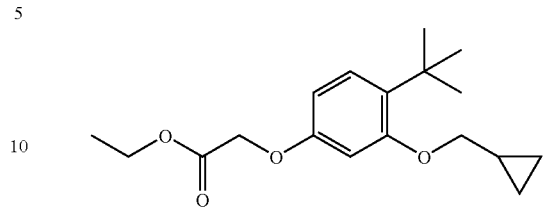

4-tert-Butyl-3-(cyclopropylmethoxy)phenol (444 mg, 2.0 mmol), sodium hydride (60% in mineral oil) (68 mg, 1.7 mmol) and ethyl bromoacetate (270 II, 2.4 mmol) were treated in the same procedure described in Example 31(c). The crude residue was applied to a silica gel chromatography column and eluted with a volume mixture of hexane and ethyl acetate (19/1 to 9/1) to furnish 463 mg (75% yield) of the title compound as a yellow oil.

$^1$H NMR (CDCl$_3$, 300 MHz) δ ppm 0.25–0.40 (2H, m), 0.55–0.69 (2H, m), 1.30 (3H, t, J=6.8 Hz), 1.35 (1H, m), 1.37 (9H, s), 3.79 (2H, d, J=6.8 Hz), 4.28 (2H, q$_{AB}$, J=7.2 Hz), 4.58 (2H, s), 6.31 (1H, dd, J=2.7, 8.6 Hz), 6.49 (1H, dd, J=2.5 Hz), 7.15 (1H, d, J=8.6Hz).

MS (ESI) m/z: 307 [M+H]$^+$.

32(d): [4-tert-Butyl-3-(cyclopropylmethoxy)phenoxy]acetic acid

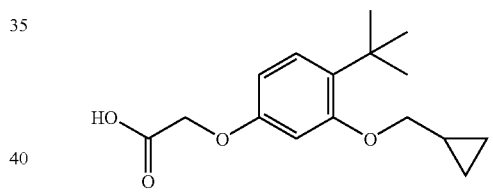

Ethyl [4-tert-butyl-3-(cyclopropylmethoxy)phenoxy]acetate (460 mg, 1.5 mmol) was treated in the same procedure described in Example 31(d). The crude residue was applied to recrystallization from hexane to furnish 357 mg (85% yield) of the title compound as a white solid.

$^1$H NMR (CDCl$_3$, 300 MHz) δ ppm 0.23–0.40 (2H, m), 0.50–0.73 (2H, m), 1.32 (1H, m), 1.37 (9H, s), 3.78 (2H, d, J=6.8 Hz), 4.63 (2H, s), 6.32 (1H, dd, J=2.6, 8.4 Hz), 6.47 (1H, d, J=2.6 Hz), 7.16 (1H, d, J=8.5 Hz), 9.01 (1H, brs).

MS (ESI) m/z: 279 [M+H]$^+$.

32(e): 2-[4-tert-Butyl-3-(cyclopropylmethoxy)phenoxy]-N-{3-fluoro-4-[(methylsulfonyl)amino]benzyl}acetamide

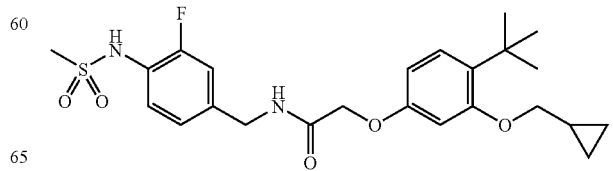

[4-tert-Butyl-3-(cyclopropylmethoxy)phenoxy]acetic acid (139 mg, 0.5 mmol), 2-chloro-1,3-dimethylimidazolinium chloride (CDI) (89 mg, 0.6 mmol), triethylamine (0.2 ml) and N-[4-(aminomethyl)-2-fluorophenyl]methanesulfonamide hydrochloride (140 mg, 0.6 mmol) were treated in the same procedure described in Example 2(b). The crude residue was applied to a silica gel chromatography column and eluted with a volume mixture of hexane and ethyl acetate (3/1) to furnish 188 mg (78% yield) of the title compound as a white solid.

$^1$H NMR (CDCl$_3$, 300 MHz) δ ppm 0.29–0.37 (2H, m), 0.59–0.68 (2H, m), 1.31 (1H, m), 1.36 (9H, s), 3.01 (3H, s), 3.77 (2H, d, J=7.3 Hz), 4.50 (2H, d, J=5.9 Hz), 4.53 (2H, s), 6.33–6.42 (2H, m), 6.50 (1H, brs), 6.94 (1H, brs), 7.03–7.10 (2H, m), 7.18 (1H,d, J=8.6 Hz), 7.51 (1H, t, J=8.6 Hz).

MS (ESI) m/z: 479 [M+H]$^+$.

Example 33

2-(4-tert-Butylphenoxy)-N-((1R)-1-{4-[(methylsulfonyl)amino]phenyl}ethyl)acetamide 33(a): 2-(4-tert-butylphenoxy)-N-[4(1R)-1-(4-nitrophenyl)ethyl]acetamide

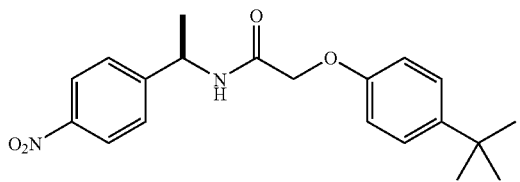

(4-tert-Butylphenoxy)acetic acid (202 mg, 1.0 mmol), 2-chloro-1,3-dimethylimidazolinium chloride (CDI) (170 mg, 1.1 mmol), triethylamine (1.0 ml) and (1R)-1-(4-nitrophenyl)ethanamine hydrochloride (208 mg, 1.0 mmol, Aldrich) were treated in the same procedure described in Example 2(b). The crude residue was applied to a silica gel chromatography column and eluted with hexane and ethylacetate (4/1) to furnish 360 mg (100% yield) of the title compound as colorless oil.

$^1$H NMR (270 MHz, CDCl$_3$) δ ppm 1.31 (9H, s), 1.56 (2H, d, J=6.6 Hz), 4.51 (2H, d, J=2.0 Hz), 5.27 (1H, m), 6.87 (2H, d, J=8.6 Hz), 6.92 (1H, brs), 7.35 (2H, d, J=8.6 Hz), 7.44 (2H, d, J=8.6 Hz), 8.18 (2H, d, J=8.6 Hz).

MS (ESI) m/z 357 [M+H]$^+$, 355 [M−H]$^-$.

33(b): N-[(1R)-1-(4-Aminophenyl)ethyl]-2-(4-tert-butylPhenoxy)acetamide

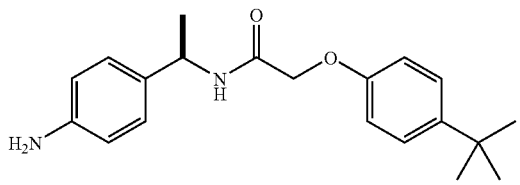

A mixture of 2-(4-tert-butylphenoxy)-N-[(1R)-1-(4-nitrophenyl)ethyl]acetamide (360 mg, 1.0 mmol) and 10% Pd—C (50 mg) in methanol (10 ml) was stirred under H$_2$ balloon pressure for 1 hour at ambient temperature. Then, filtration to remove 10% Pd—C, evaporation gave 420 mg of the title compound as yellow oil.

$^1$H NMR (270 MHz, CDCl$_3$) δ ppm 1.30 (9H, s), 1.50 (2H, d, J=7.3 Hz), 3.50 (2H, brs), 4.47 (2H, s), 5.15 (1H, m), 6.81 (1H, brs), 6.76 (2H, d, J=8.6 Hz), 6.85 (2H, d, J=8.6 Hz), 7.14 (2H, d, J=8.6 Hz), 7.33 (2H, d, J=8.6 Hz).

MS (ESI) m/z 327 [M+H]$^+$.

33(c):2-(4-tert-Butylphenoxy)-N-(1R)-1-{4-[(methylsulfonyl)amino]phenyl}ethyl)acetamide

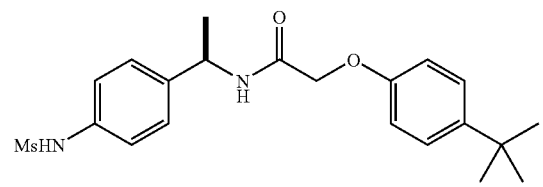

To a pyridine (5.0 ml) solution of N-[(1R)-1-(4-aminophenyl)ethyl]-2-(4-tert-butylphenoxy)acetamide (420 mg, 1.0 mmol), methanesulfonyl chloride (114 mg, 1.0 mmol) was added at 0° C. and the mixture was stirred for 3 hours at 0° C. The reaction mixture was then quenched with 2 M HCl and then crude products were extracted with methylene dichloride The organic layer was then washed with brine, dried over Na$_2$SO$_4$. After filtration to separate solvent and sodium sulfate, the solvent was removed under reduced pressure to give a residue, which was applied to a silica gel chromatography column and eluted with methylene dichloride/ethylacetate=1/1 to furnish 120 mg (29% yield) of the title as a white solid.

$^1$H NMR (CDCl$_3$, 270 MHz) δ ppm 1.30 (9H, s), 1.52 (3H, d, J=6.6 Hz), 3.00 (3H, s), 4.50 (s, 2H), 5.18 (1H, m), 6.87 (1H, brs), 6.87 (2H, d, J=7.9 Hz), 7.17 (2H, d, J=7.9 Hz), 7.26 (1H, brs), 7.26 (2H, d, J=7.9 Hz), 7.33 (2H, d, J=7.9 Hz).

MS (ESI) m/z: 405 [M+H]$^+$, 403 [M−H]$^-$.

Example 34

2-[3-Butoxy-4-tert-butylphenoxyl-N{3-fluoro-4-[(methylsulfonyl)amino]benzyl}acetamide 34(a): 3-butoxy-4-tert-butylphenyl tert-butyl carbonate

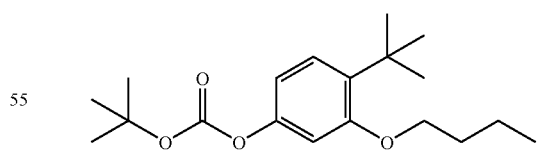

tert-Butyl 4-tert-butyl-3-hydroxyphenyl carbonate (1.5 g, 5.6 mmol), n-butanol (0.5 mL, 5.4 mmol), triphenylphosphine (1.3 g, 5.0 mmol) and diethyl azodicarboxylate (DEAD) (0.78 mL, 5.0 mmol) were treated in the same procedure described in Example 31(a). The crude residue was applied to a silica gel chromatography column and eluted with a volume mixture of hexane and ethyl acetate (19/1 to 9/1) to furnish 964 mg (66% yield) of the title compound as a colorless oil.

¹H NMR (CDCl₃, 300 MHz) δ ppm 0.99 (3H, t, J=7.3 Hz), 1.36 (9H, s), 1.56 (9H, s), 1.46–1.66 (2H, m), 1.73–1.92 (2H, m), 3.96 (2H, t, J=5.9 Hz), 6.63–6.73 (2H, m), 7.24 (1H, d, J=8.6 Hz).
MS (ESI) m/z: 323 [M+H]⁺.

34(b): 3-Butoxy-4-tert-butylphenol

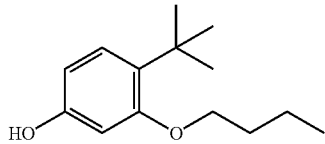

3-Butoxy-4-tert-butylphenyl tert-butyl carbonate (960 mg, 3.0 mmol) was treated in the same procedure described in Example 32(b). The crude residue was applied to a silica gel chromatography column and eluted with a volume mixture of hexane and ethyl acetate (19/1 to 2/1) to furnish 641 mg (96% yield) the title compound as a white solid.
¹H NMR (CDCl₃, 300 MHz) δ ppm 0.99 (3H, t, J=7.3 Hz), 1.35 (9H, s), 1.46–1.68 (2H, m), 1.73–1.91 (2H, m), 3.94 (2H, t, J=6.6 Hz), 4.67 (1H, brs), 6.31 (1H, dd, J=2.2, 8.8 Hz), 6.41 (1H, d, J=2.3 Hz), 7.09 (1H, d, J=8.8 Hz).
MS (ESI) m/z: 221 [M–H]⁻.

34(c): Ethyl (3-butoxy-4-tert-butylphenoxy)acetate

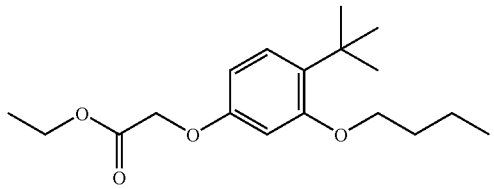

3-Butoxy-4-tert-butylphenol (640 mg, 2.9 mmol), potassium carbonate (1.2 g, 8.6 mmol) and ethyl bromoacetate (480 ul, 4.3 mmol) were treated in the same procedure described in Example 33(d). The crude residue was applied to a silica gel chromatography column and eluted with a volume mixture of hexane and ethyl acetate (19/1 to 4/1) to furnish 856 mg (96% yield) of the title compound as a colorless oil.
¹H NMR (CDCl₃, 300 MHz) δ ppm 0.99 (3H, t, J=7.2 Hz), 1.31 (3H, t, J=7.2 Hz), 1.35 (9H, s), 1.45–1.61 (2H, m), 1.73–1.92 (2H, m), 3.95 (2H, t, J=6.0 Hz), 4.28 (2H, qAB, J=7.2 Hz), 4.59 (2H, s), 6.31 (1H, dd, J=2.7, 8.6Hz), 6.55 (1H, d, J=2.0 Hz), 7.15 (1H, d, J=8.6 Hz).
MS (ESI) m/z: 309 [M+H]⁺.

34(d): (3-Butoxy-4-tert-butylphenoxy)acetic acid

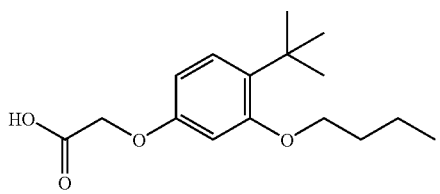

Ethyl (3-butoxy-4-tert-butylphenoxy)acetate (855 mg, 2.8 mmol) was treated in the same procedure described in Example 31(d). The crude residue was applied to recrystallization from hexane to furnish 485 mg (63% yield) of the title compound as a white solid.
¹H NMR (CDCl₃, 300 MHz) δ ppm 0.97 (3H, t, J=7.3 Hz), 1.34 (9H, s), 1.42–1.64 (2H, m), 1.68–1.94 (2H, m), 3.92 (2H, m), 4.58 (2H, s), 6.31 (1H, d, J=7.4 Hz), 6.52 (1H, brs), 7.14 (1H, d, J=8.0 Hz).
MS (ESI) m/z: 281 [M+H]⁺.

34(e): 2-[3-Butoxy-4-tert-butylphenoxyl-N{3-fluoro-4-[(methylsulfonyl)amino]benzyl}acetamid

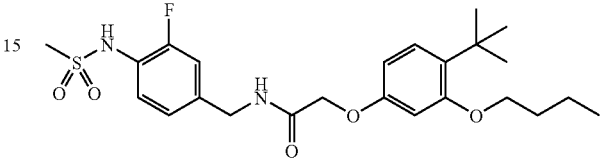

(3-Butoxy-4-tert-butylphenoxy)acetic acid (140 mg, 0.5 mmol), 2-chloro-1,3-dimethylimidazolinium chloride (CDI) (105 mg, 0.65 mmol), triethylamine (0.33 ml) and N44-(aminomethyl)-2-fluorophenyl]methanesulfonamide hydrochloride (153 mg, 0.6 mmol) were treated in the same procedure described in Example 2(b). The crude residue was applied to a silica gel chromatography column and eluted with a volume mixture of hexane and ethyl acetate (3/1 to 1/1) to furnish 140 mg (58% yield) of the title compound as a white solid.
¹H NMR (CDCl₃, 300 MHz) δ ppm 0.99 (3H, t, J=7.3 Hz), 1.35 (9H, s), 1.46–1.59 (2H, m), 1.73–1.90 (2H, m), 3.02 (3H, s), 3.94 (2H, t, J=6.6 Hz), 4.52 (2H, d, J=5.9 Hz), 4.55 (2H, s), 6.39 (1H, dd, J=2.2, 8.1 Hz), 6.48 (1H, d, J=3.0 Hz), 6.52 (1H, brs), 6.97 (1H, brt, J=5.1 Hz), 7.07 (1H, s), 7.10 (1H, s), 7.19 (1H, d, J=8.8 Hz), 7.53 (1H, t, J=8.1 Hz).
MS (ESI) m/z: 481 [M+H]⁺.

Example 35

2-[(4,4-Dimethyl-3,4-dihydro-2H-chromen-7-yl)oxy]-N{3-fluoro-4-[(methylsulfonyl)amino]benzyl}acetamide 35(a): 7-Methoxy-4,4-dimethylchroman-2-one

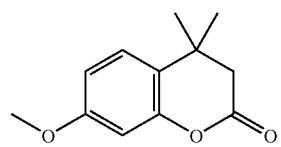

A mixture of 3-methoxy-phenol (12 g, 96.5 mmol) and conc. sulfuric acid (0.5 ml) was heated at 130° C. with stirring, and methyl 3,3-dimethylacrylate (5.8 g, 51 mmol) was added. The mixture was stirred at 13° C. for 3 hours. After being cooled to ambient temperature, the organic layer was dissolved in ethyl acetate. The organic layer washed with brine, dried over sodium sulfate. After filtration to separate solvent and sodium sulfate, the solvent was removed under reduced pressure to give a residue, which was applied to a silica gel chromatography column and eluted with ethyl acetate/hexane=⅑ to furnish 4.1 g (39% yield) of the title compound as a brown solid.

¹H NMR (CDCl₃, 300 MHz) δ ppm 1.33 (6H, s), 2.61 (2H, s), 3.80 (3H, s), 6.63 (1H, d, J=2.2 Hz), 6.71 (1H, dd, J=2.2, 8.8 Hz), 7.21 (1H, d, J=8.1 Hz).

MS (ESI) m/z: 207 [M+H]⁺.

35(b): 2-(3-Hydroxy-1,1-dimethylpropyl)-5-methoxyphenol

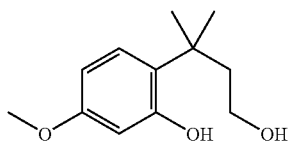

To a tetrahydrofran (THF) (20 ml) solution of 7-methoxy-4,4-dimethylchroman-2-one (4.1 g, 19.7 mmol) was added lithium aluminum hydride (750 mg, 19.7 mmol) at 0° C. The reaction mixture was stirred at 0° C. for 1 hour. To the mixture was added H₂O (1 ml) carefully to form a white prepicitate. The organic layer was dried over magnesium sulfate. After filtration to separate solvent and magnesium sulfate and precipitate, the solvent was removed under reduced pressure to give a residue, which was applied to a silica gel chromatography column and eluted with ethyl acetate/hexane=¼ to furnish 3.0 g (76% yield) of the title compound as colorless oil.

¹H NMR (CDCl₃, 300 MHz) δ ppm 1.39 (6H, s), 2.17 (2H, t, J=6.6 Hz), 3.54 (2H, q$_{AB}$, J=4.4 Hz), 3.75 (3H, s), 5.96 (1H, brs), 6.25 (1H, d, J=2.2 Hz), 6.41 (1H, dd, J=2.9, 8.8 Hz), 7.10 (1H, d, J=8.1 Hz).

MS (ESI) m/z: 211 [M+H]⁺.

35(c): 7-Methoxy-4,4-dimethylchromane

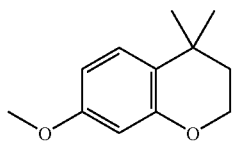

To a toluene (30 ml) solution of 2-(3-hydroxy-1,1-dimethylpropyl)-5-methoxyphenol (3.0 g, 14.3 mmol) was added catalytic amount of p-toluenesulfonic acid. The stirred mixture was refluxed for 2 hours. The reaction mixture was then quenched with saturated aqueous solution of sodium bicarbonate and then crude products were extracted with ethyl acetate The organic layer was then washed with brine, dried over sodium sulfate. After filtration to separate solvent and sodium sulfate, the solvent was removed under reduced pressure to give a residue, which was applied to a silica gel chromatography column and eluted with ethyl acetate/hexane=1/9 to furnish 2.1 g (75% yield) of the title compound as a colorless oil.

¹H NMR (CDCl₃, 300 MHz) δ ppm 1.30 (6H, s), 1.81 (2H, t, J=5.8 Hz), 3.75 (3H, s), 4.19 (2H, t, J=5.2 Hz), 6.35 (1H, d, J=2.9 Hz), 6.49 (1H, dd, J=2.2, 8.8 Hz), 7.15 (1H, d, J=8.1 Hz).

MS (ESI) m/z: 193 [M+H]⁺.

35(d): 4,4-Dimethylchroman-7-ol

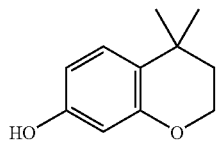

To a methylene chloride (3 ml) solution of 7-methoxy-4,4-dimethylchromane (1.9 g, 9.7 mmol) was added methylene chloride solution of boron tribromide (1M, 19.4 mL, 19.4 mmol) at 0° C. The mixture was stirred at 0° C. for 1 hour. The reaction mixture was then quenched with methanol and then the solvent was removed under reduced pressure to give a residue, which was applied to a silica gel chromatography column and eluted with ethyl acetate/hexane=¼ to furnish 1.3 g (75% yield) of the title compound as a yellow solid.

¹H NMR (CDCl₃, 300 MHz) δ ppm 1.30 (6H, s), 1.80 (2H, t, J=5.1 Hz), 4.18 (2H, t, J=5.1 Hz), 4.76 (1H, brs), 6.29 (1H, d, J=2.9 Hz), 6.40 (1H, dd, J=2.9, 8.8 Hz), 7.11 (1H, d, J=8.1 Hz).

MS (ESI) m/z: 179 [M+H]⁺.

35(e): Ethyl [(4,4-dimethyl-3,4-dihydro-2H-chromen-7-yl)oxy]acetate

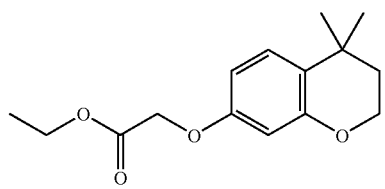

4,4-Dimethylchroman-7-ol (1.4 g, 8.0 mmol), potassium carbonate (3.3 g, 24.0 mmol) and ethyl bromoacetate (1.0 mL, 9.2 mmol) were treated in the same procedure described in Example 33(d). The crude residue was applied to a silica gel chromatography column and eluted with a volume mixture of hexane and ethyl acetate (19/1 to 4/1) to furnish 2.1 g (98% yield) of the title compound as a colorless oil.

¹H NMR (CDCl₃, 300 MHz) δ ppm 1.30 (3H, t, J=7.4 Hz), 1.30 (6H, s), 1.80 (2H, t, J=5.8 Hz), 4.18 (2H, t, J=5.1 Hz), 4.27 (2H, q$_{AB}$, J=7.4 Hz), 4.56 (2H, s), 6.32 (1H, d, J=2.2 Hz), 6.50 (1H, dd, J=2.9, 8.8 Hz), 7.15 (1H, d, J=8.8 Hz).

MS (ESI) m/z: 265 [M+H]⁺.

35(f): [(4,4-Dimethyl-3,4-dihydro-2H-chromen-7-yl)oxy]acetic acid

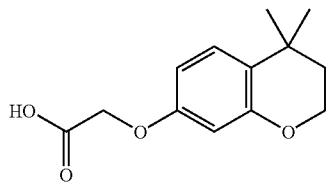

Ethyl [(4,4-dimethyl-3,4-dihydro-2H-chromen-7-yl)oxy]acetate (2.1 g, 7.8 mmol) was treated in the same procedure described in Example 31(d). The crude residue was applied to recrystallization from hexane to furnish 1.65 g (89% yield) of the title compound as a white solid.

$^1$H NMR (CDCl$_3$, 300 MHz) δ ppm 1.30 (6H, s), 1.81 (2H, t, J=4.4 Hz), 4.19 (2H, t, J=5.2 Hz), 4.63 (2H, s), 6.35 (1H, d, J=2.9 Hz), 6.51 (1H, dd, J=2.2, 8.1 Hz), 7.18 (1H, d, J=8.8 Hz).

MS (ESI) m/z: 237 [M+H]$^+$.

35(g): 2-[(4,4-Dimethyl-3,4-dihydro-2H-chromen-7-yl)oxy]-N{3-fluoro-4-[(methylsulfonyl)amino]benzyl}acetamide

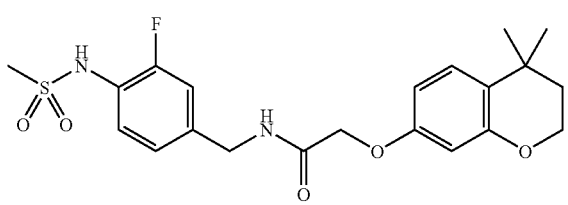

[(4,4-Dimethyl-3,4-dihydro-2H-chromen-7-yl)oxy]acetic acid (118 mg, 0.5 mmol), 2-chloro-1,3-dimethylimidazolinium chloride (CDI) (89 mg, 0.55 mmol), triethylamine (0.33 ml) and N{4-(aminomethyl)-2-fluorophenyl]methanesulfonamide hydrochloride (140 mg, 0.55 mmol) were treated in the same procedure described in Example 2(b). The crude residue was applied to a silica gel chromatography column and eluted with a volume mixture of hexane and ethyl acetate (3/1 to 1/1) to furnish 43 mg (20% yield) of the title compound as a white solid.

$^1$H NMR (CDCl$_3$, 300 MHz) δ ppm 1.30 (6H, s), 1.81 (2H, t, J=5.2 Hz), 3.02 (3H, s), 4.19 (2H, t, J=5.1 Hz), 4.51 (2H, d, J=5.8 Hz), 4.51 (2H, s), 6.36 (1H, d, J=3.0 Hz), 6.48 (1H, dd, J=3.0, 8.8 Hz), 6.58 (1H, brs), 6.96 (1H, brt, J=5.2 Hz), 7.01–7.12 (2H, m), 7.18 (1H, d, J=8.8 Hz).

MS (ESI) m/z: 454 [M−18]$^+$.

Example 36

2-(4-tert-Butyl-3-fluorophenoxy)-N-{3-methoxy-4-[(methylsulfonyl)amino]benzyl}acetamide

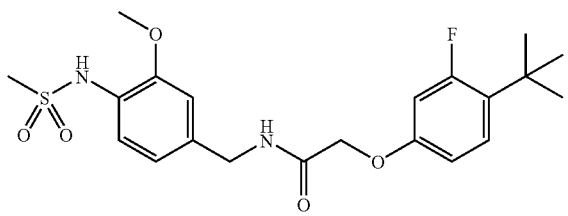

(4-tert-Butyl-3-fluorophenoxy)acetic acid (113 mg, 0.5 mmol), 2-chloro-1,3-dimethylimidazolinium chloride (CDI) (89 mg, 0.55 mmol), triethylamine (0.33 ml) and N-[4-(aminomethyl)-3-methoxyphenyl]methanesulfonamide trifluoroacetic acid (258 mg, 0.75 mmol) were treated in the same procedure described in Example 2(b). The crude residue was applied to a silica gel chromatography column and eluted with a volume mixture of hexane and ethyl acetate (3/1 to 1/1) to furnish 43 mg (20% yield) of the title compound as a white solid.

$^1$H NMR (CDCl$_3$, 300 MHz) δ ppm 1.34 (9H, s), 2.95 (3H, s), 3.86 (3H, s), 4.52 (2H, d, J=6.6 Hz), 4.53 (2H, s), 6.52–6.68 (2H, m), 6.77 (1H, brs), 6.82–6.99 (3H, m), 7.22 (1H, t, J=8.1 Hz).

MS (ESI) m/z: 439 [M+H]$^+$.

Example 37

2-(4-tert-Butyl-3-chlorophenoxy)-N{3-methoxy-4-[(methylsulfonyl)amino]benzyl}acetamide

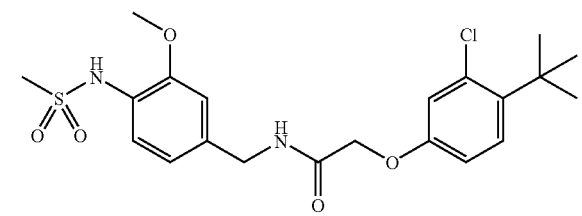

(4-tert-Butyl-3-chlorophenoxy)acetic acid (121 mg, 0.5 mmol), 2-chloro-1,3-dimethylimidazolinium chloride (CDI) (97 mg, 0.6 mmol), triethylamine (0.33 ml) and N44-(aminomethyl)-3-methoxyphenyl]methanesulfonamide trifluoroacetic acid (206 mg, 0.6 mmol) were treated in the same procedure described in Example 2(b). The crude residue was applied to a silica gel chromatography column and eluted with a volume mixture of hexane and ethyl acetate (3/1 to 1/1) to furnish 43 mg (20% yield) of the title compound as a white solid.

$^1$H NMR (CDCl$_3$, 300 MHz) δ ppm 1.45 (9H, s), 2.95 (3H, s), 3.86 (3H, s), 4.51 (2H, d, J=7.9 Hz). 4.53 (2H, s), 6.69–6.80 (2H, m), 6.80–6.92 (3H, m), 6.96 (1H, d, J=2.7 Hz), 7.36 (1H, d, J=8.6 Hz), 7.49 (1H,d, J=8.6 Hz).

MS (ESI) m/z: 455 [M+H]$^+$.

Example 38

2-(4-tert-Butyl-3-hydroxyphenoxy)-N-((1R)-1–1-{3-methyl-4-[(methylsulfonyl)amino]phenyl}ethyl)acetamide 38(a): 3-(Benzyloxy)-4-tert-butylphenyl tert-butyl carbonate

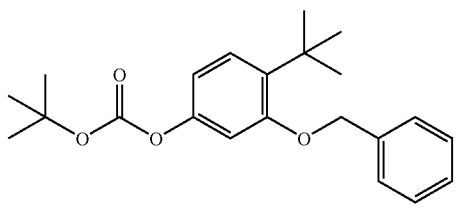

To an acetone (100 mL) solution of tert-butyl 4-tert-butyl-3-hydroxyphenyl carbonate (*J. Org. Chem.* 2001, 66, 3435) (5.5 g, 20.7 mmol) were added potassium carbonate (8.6 g, 63 mmol) and benzyl bromide (3.0 ml, 25.0 mmol). The stirred mixture was refluxed at 65° C. for 4 hours. The precipitate was filtered off and washed with acetone. The filtrate was concentrated under reduced pressure to give a residue, which was applied to a silica gel chromatography column and eluted with ethyl acetate/hexane=1/30 to furnish 7.1 g (96% yield) of the title compound as a colorless oil.

¹H NMR (CDCl₃, 300 MHz) δ ppm 1.37 (9H, s), 1.56 (9H, s), 5.07 (2H, s), 6.64–6.82 (5H, m).

MS (ESI) m/z: 357 [M+H]⁺.

38(b): 3-(Benzyloxy)-4-tert-butylphenol

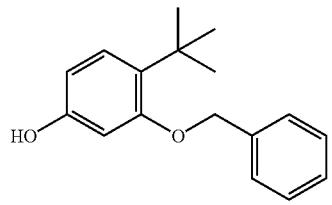

To a diethylether (100 ml) solution of 3-(benzyloxy)-4-tert-butylphenyl tert-butyl carbonate (7.1 g, 20 mmol) was added lithium aluminum hydride (0.75 g, 20 mmol) at 0° C. The reaction mixture was 10 stirred at ambient temperature for 3 hours. To the mixture was added H₂O (10 ml) carefully to form a white prepicitate. The organic layer was dried over magnesium sulfate. After filtration to separate solvent and magnesium sulfate and precipitate, the solvent was removed under reduced pressure to give a residue, which was applied to a silica gel chromatography column and eluted with ethyl acetate/hexane =1/6 to furnish 4.9 g (96% yield) of the title compound as colorless oil.

¹H NMR (CDCl₃, 300 MHz) δ ppm 1.36 (9H, s), 4.66 (1H, s), 5.08 (2H, s), 6.35 (1H, dd, J=2.6, 8.5 Hz), 6.49 (1H, d, J=2.7 Hz), 7.14 (1H, d, 8.6 Hz), 7.28–7.51 (5h, m).

38(c): Ethyl [3-(benzyloxy)-4-tert-butylphenoxy]acetate

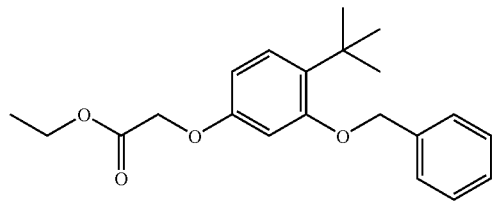

3-(Benzyloxy)-4-tert-butylphenol (4.9 g, 19.2 mmol), potassium carbonate (8.0 g, 57.6 mmol) and ethyl bromoacetate (2.6 ml, 23.0 mmol) were treated in the same procedure described in Example 13(d). The crude residue was applied to a silica gel chromatography column and eluted with a volume mixture of hexane and ethyl acetate (29/1 to 19/1) to furnish 5.6 g (85% yield) of the title compound as a colorless oil.

¹H NMR (CDCl₃, 300 MHz) δ ppm 1.31 (3H, t, J=7.3 Hz), 1.36 (9H, s), 4.28 (2H, q_{AB}, J=7.2 Hz), 4.58 (2H, s), 5.08 (2H, s), 6.36 (1H, dd, J=2.6, 8.6 Hz), 6.63 (1H, d, J=2.7 Hz), 7.19 (1H, d, J=8.6 Hz), 7.30–7.53 (5H, m).

MS (ESI) m/z: 343 [M+H]⁺.

38(d): [3-(Benzyloxy)-4-tert-butylphenoxy]acetic acid

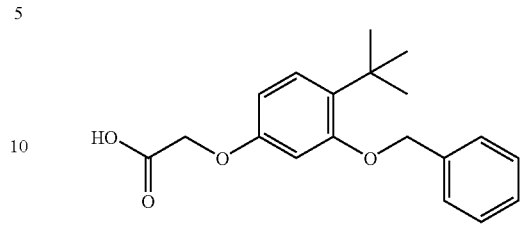

Ethyl [3-(benzyloxy)-4-tert-butylphenoxy]acetate (342 mg, 1.0 mmol) was treated in the same procedure described in Example 31(d). The crude residue was applied to recrystallization from hexane to furnish 251 mg (80% yield) of the title compound as a white solid.

MS (ESI) m/z: 315 [M+H]⁺.

38(e): 2-(4-tert-Butyl-3-hydroxyphenoxy)-N'-((1R)-1-{3-methyl-4-[(methylsulfonyl)amino]phenyl}ethyl)acetamide

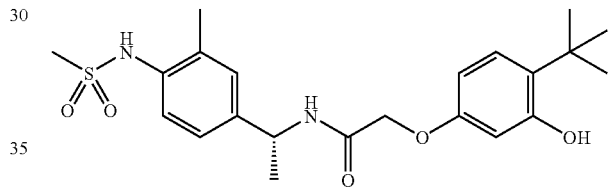

To a tetrahydrofuran (THF) (3 ml) solution of [3-(benzyloxy)-4-tert-butylphenoxy]acetic acid (110 mg, 0.35 mmol) was added 1,1'-carbonyl-diimidazole (63 mg, 0.39 mmol) and the mixture was stirred for 2 hours at ambient temperature. To the mixture were added N-{4-[(1R)-1-aminoethyl]-2-methylphenyl}methanesulfonamide hydrochloride (100 mg, 0.39 mmol) and triethyl amine (150 μl, 1.1 mmol) and the mixture was stirred for 14 hours at ambient temperature. After filtration to separate solvent and the resulting percipitate, the solvent was removed under reduced pressure to give a residue. The residue was dissolved in methanol (3 ml). To the mixture was added palladium hydroxide (50 mg). Into the mixture was charged hydrogen gas. The mixture was stirred under hydrogen atmosphere at ambient temperature for 1 hour. After filtration to separate solvent and the catalyst, the solvent was removed under reduced pressure to give a residue, which was applied to a silica gel chromatography column and eluted with ethyl acetate/hexane=1/1 to furnish 88 mg (56% yield) of the title compound as a white solid.

¹H NMR (CDCl₃, 300 MHz) δ ppm 1.30 (9H, s), 1.38 (3H, d, J=7.2 Hz), 2.26 (3H, s), 2.95 (3H, s), 4.41 (2H, q_{AB}, J=14.5 Hz), 4.96 (1H, m), 6.28 (1H, dd, J=2.6, 8.5 Hz), 6.42 (1H, d, J=2.7 Hz), 7.01 (1H, d, J=8.6 Hz), 7.06–7.18 (2H, m), 7.19 (1H, d, J=7.9 Hz), 8.43 (1H, d, J=7.9 Hz), 9.00 (1H, s), 9.40 (1H, s).

MS (ESI) m/z: 435 [M+H]⁺.

The invention claimed is:
1. A compound of the formula (I):

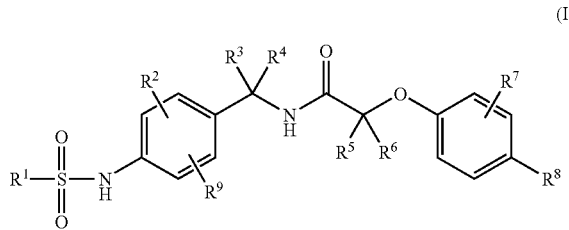

wherein $R^1$ represents a $(C_1-C_6)$alkyl group; $R^2$ represents a hydrogen atom, a halogen atom, a hydroxy group, a $(C_1-C_6)$alkyl group or a $(C_1-C_6)$alkoxy group; $R^3$, $R^4$, $R^5$ and $R^6$ each independently rpresents a hydrogen atom, a $(C_1-C_6)$alkyl, or a halogen atom; $R^7$ represents a hydrogen atom, a halogen atom, a hydroxy group, a $(C_1-C_6)$alkyl group optionally substituted with a piperidino group, a $(C_1-C_6)$alkoxy group optionally substituted with a 3–7 membered cycloalkyl ring, a hydroxy$(C_1-C_6)$alkoxy group, a $(C_1-C_6)$alkoxy-$(C_1-C_6)$alkyl group, a $(C_1-C_6)$alkoxy-$(C_1-C_6)$alkoxy group, a halo $(C_1-C_6)$alkyl group, a $(C_1-C_6)$alkylthio group, a $(C_1-C_6)$alkylsulfinyl group or a $(C_1-C_6)$alkylsulfonyl group; $R^8$ represents a $(C_1-C_6)$alkyl group, a halo$(C_1-C_6)$alkyl group, a $(C_1-C_6)$alkoxy group, a hydroxy $(C_1-C_6)$alkoxy group, a $(C_1-C_6)$alkoxy-$(C_1-C_6)$alkyl group or a $(C_1-C_6)$alkoxy-$(C_1-C_6)$alkoxy group; or $R^7$ and $R^8$, when adjacent to each other, taken together with the carbon atoms to which they are attached form a 5–8 membered carbocyclic or heterocyclic ring, wherein the carbocyclic ring or the heterocyclic ring is unsubstituted or substituted with one or more substituents selected from the group consisting of a hydroxy group, a $(C_1-C_6)$alkyl group, a $(C_1-C_6)$alkoxy group and a hydroxy$(C_1-C_6)$alkyl group; and $R^9$ represents a hydrogen atom or a halogen atom; or a pharmaceutically acceptable salt or solvate thereof.

2. A compound according to claim 1, wherein $R^1$ represents a methyl group; $R^2$ represents a hydrogen atom, a halogen atom, a $(C_1-C_6)$alkyl group or a $(C_1-C_6)$alkoxy group; $R^7$ represents a hydrogen atom, a halogen atom, a hydroxy group, a $(C_1-C_6)$alkyl group substituted with a piperidino group or a $(C_1-C_6)$alkoxy group substituted with a 3–7 membered carbocyclic ring; and $R^8$ represents a $(C_1-C_6)$ alkyl group or a halo $(C_1-C_6)$alkyl group; or $R^7$ and $R^8$, when adjacent to each other, taken together with the carbon atoms to which they are attached form a 5–6 membered carbocyclic or heterocyclic ring, wherein the carbocyclic ring or the heterocyclic ring is unsubstituted or substituted with one or more $(C_1-C_6)$ alkyl groups.

3. A compound according to claim 2, wherein $R^2$ represents a hydrogen atom, a halogen atom, a $(C_1-C_3)$alkyl group or a $(C_1-C_3)$alkoxy group; $R^3$ represents a hydrogen atom or a methyl group; $R^4$ represents a hydrogen atom; $R^5$ and $R^6$ each independently represents a hydrogen atom or a halogen atom; and $R^8$ represents a $(C_4-C_5)$alkyl group or a halo$(C_1-C_4)$alkyl group; or $R^7$ and $R^8$, when adjacent to each other, taken together with the carbon atoms to which they are attached form a 5–6 membered carbocyclic ring or a 6 membered heterocyclic ring containing an oxygen atom, wherein the carbocyclic ring or the heterocyclic ring is substituted with one or more $(C_1-C_6)$alkyl groups.

4. A compound according to claim 3, wherein $R^2$ represents a hydrogen atom, a chloro atom, a fluoro atom or a methyl group; $R^7$ represents a hydrogen atom, a chloro atom, a fluoro atom, a hydroxy group, a $(C_1-C_6)$alkyl group substituted with a piperidino group or a $(C_1-C_6)$alkoxy group substituted with a 3–7 membered carbocyclic ring; and $R^8$ represents a tert-butyl group, a trifluoromethyl group or a 2,2,2-trifluoro-1,1-dimethylethyl group; or $R^7$ and $R^8$, when adjacent to each other, taken together with the carbon atoms to which they are attached form 3,4-dihydro-2H-pyran or cyclopentane substituted with one or more methyl groups.

5. A compound according to claim 4, wherein
$R^2$ represents a hydrogen atom, a fluoro atom or a methyl group; $R^4$, $R^5$ and $R^6$ each represents a hydrogen atom; $R^9$ represents a hydrogen atom; and
$R^7$ represents a hydrogen atom, a fluoro atom, a chloro atom or a piperidinomethyl group, and $R^8$ represents a tert-butyl group;
$R^7$ represents a hydrogen atom and $R^8$ represents a 2,2,2-trifluoro-1,1-dimethylethyl group;
$R^7$ represents a chloro atom and $R^8$ represents a trifluoromethyl group;
or $R^7$ and $R^8$, when adjacent to each other, taken together with the carbon atoms to which they are attached form 1,1-dimethylcyclopentane.

6. A compound according to claim 5 selected from
2-(4-tert-Butyl-3-chlorophenoxy) -N-3-fluoro-4-[(methylsulfonyl)amino]benzyl}acetamide;
2-(4-tert-Butyl-3-chlorophenoxy)-N-((1R)-1-{4-[(methylsulfonyl)amino]phenyl}ethyl)acetamide;
2-(4-tert-Butyl-3-chlorophenoxy)-N-((1R)-1-{3-fluoro-4-[(methylsulfonyl)amino]phenyl}ethyl)acetamide;
2-(4-tert-Butyl-3-chlorophenoxy)-N-((1R)-1-{3-methyl-4-[(methylsulfonyl)amino]phenyl}ethyl)acetamide;
2-(4-tert-Butyl-3-fluorophenoxy)-N-((1R)-1-{4-[(methylsulfonyl)amino]phenyl}ethyl)acetamide;
2-(4-tert-Butyl-3-fluorophenoxy)-N-((1R)-1-{3-fluoro-4-[(methylsulfonyl)amino]phenyl}ethyl)acetamide;
2-(4-tert-Butyl-3-fluorophenoxy)-N-{3-methyl-4-[(methylsulfonyl)amino]benzyl}acetamide;
2-(4-tert-Butyl-3-fluorophenoxy)-N-((1R)-1-{3-methyl-4-[(methylsulfonyl)amino]phenyl}ethyl)acetamide;
2-[(1,1-Dimethyl-2,3-dihydro-1H-inden-5-yl)oxy]-N-{3-fluoro-4-[(methylsulfonyl)amino]benzyl}acetamide;
2-(4-tert-Butylphenoxy)-N-{3-methyl-4-[(methylsulfonyl)amino]benzyl}acetamide;
2-[4-tert-Butyl-2-(piperidin-1-ylmethyl)phenoxy]-N-((1R)-1-{3-methyl-4-[(methylsulfonyl)amino]phenyl}ethyl)acetamide;
2-(4-tert-Butylphenoxy)-N-((1R)-1-{3-methyl-4-[(methylsulfonyl)amino]phenyl}ethyl)acetamide;
N-((1R)-1 -{3-Methyl-4-[(methylsulfonyl)amino]phenyl}ethyl)-2-[4-(2,2,2-trifluoro-1,1-dimethylethyl)phenoxy]acetamide;
2-(4-tert-Butylphenoxy)-N-((1R)-1-{4-[(methylsulfonyl)amino]phenyl}ethyl)acetamide;
2-[3-Chloro-4-(trifluoromethyl)phenoxy]-N-{3-methyl-4-[(methylsulfonyl)amino]benzyl}acetamide; and
2-(4-tert-Butyl-3-hydroxyphenoxy)-N-((1R)-1-{3-methyl-4-[(methylsulfonyl)amino]phenyl}ethyl)acetamide; or a pharmaceutically acceptable salt or solvate thereof.

7. A compound according to claim 3, wherein $R^2$ represents a fluoro atom; $R^3$, $R^4$, $R^5$ and $R^6$ each represents a hydrogen atom; $R^7$ represents a fluoro atom and $R^8$ represents a tert-butyl group; or $R^7$ and $R^8$, when adjacent to each other, taken together with the carbon atoms to which they are attached form cyclohexane substituted with one or more methyl groups; and $R^9$ represents a hydrogen atom.

8. A compound according to claim 7 selected from
2-(4-tert-Butyl-3-fluorophenoxy)-N-3-fluoro-4-[(methyl-sulfonyl)amino]benzyl;acetamide; and
2-[(5,5-Dimethyl-5,6,7,8-tetrahydronaphthalen-2-yl) oxy]-N-{3-fluoro-4-[(methylsulfonyl)amino] benzyl}acetamide; or a pharmaceutically acceptable salt or solvate thereof.

9. A pharmaceutical composition including a compound of formula (I) or a pharmaceutically acceptable salt or solvate thereof, as defined in claim 1 together with a pharmaceutically acceptable excipient.

10. A compound or a pharmaceutically acceptable salt or solvate thereof as defined in claim 1 for use as a medicament.

* * * * *